US006759516B2

(12) United States Patent
Moore et al.

(10) Patent No.: US 6,759,516 B2
(45) Date of Patent: Jul. 6, 2004

(54) METHODS OF IDENTIFYING ANTIGEN GENE SEQUENCES

(75) Inventors: Robert John Moore, Ascot Vale (AU); Timothy James Doran, Ocean Grove (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/861,451

(22) Filed: May 21, 2001

(65) Prior Publication Data

US 2002/0068289 A1 Jun. 6, 2002

Related U.S. Application Data

(63) Continuation of application No. PCT/AU99/01035, filed on Nov. 19, 1999.

(30) Foreign Application Priority Data

Nov. 20, 1998 (AU) .............................................. PP7273

(51) Int. Cl.[7] .......................... C07K 1/00; C07K 14/00; C07K 17/00; A01N 37/18; A61K 38/00

(52) U.S. Cl. ....................... 530/350; 530/820; 530/825; 514/2

(58) Field of Search ................................. 530/350, 820, 530/825; 514/2; 435/6; 536/23.1

(56) References Cited

FOREIGN PATENT DOCUMENTS

WO WO 93/03157 2/1993

OTHER PUBLICATIONS

Colman, P. M., "Effects of amino acid sequence changes on antibody–antigen interactions", Res. Immunol., vol. 145, pp. 33–6 (1994).*

Current Protocols In Molecular Biology (1998), Chapter 10.15.1–10.15.9, "Purification of recombinant proteins and study of protein interaction by epitope tagging", Contributed by Ning Zhang and Jin–Long Chen, published by John Wiley & Sons, Inc.

Gene (1996) vol. 181, pp. 167–171 by Ikeda M et al., "A fusion protein library: an improved method for rapid screening and characterisation of DNA binding or interacting proteins".

Gene (1996) vol. 169, pp. 53–58 by Wang LF et al., "BTag: a novel six–residue epitope tag for surveillance and purification of recombinant proteins".

Gene (1995) vol. 152, pp. 187–189 by Sells MA and Chernoff J, "Epitope–tag vectors for eukaryotic protein production".

Trends in Biotechnology (1990) vol. 8, pp. 88–93 by Sassenfeld HM, "Engineering proteins for purification".

* cited by examiner

*Primary Examiner*—Jeffrey Fredman
*Assistant Examiner*—Teresa Strzelecka
(74) *Attorney, Agent, or Firm*—Bacon & Thomas

(57) ABSTRACT

The present invention relates to method of identifying gene sequences of potential vaccine antigens. Also included are gene sequences and the polypeptides encoded by the gene sequences as well as the use of such sequences to induce a protective immune response in animals. Particularly, the invention relates to identifying potential antigen gene sequences of Mycoplasma, preferably *Mycoplasma hyopneumoniae*. In one aspect of the present invention there is provided a method of identifying expression proteins translated from a nucleotide sequence in an expression vector, said method comprising the use of a marker co-expressed with a protein translated from the nucleotide sequence. In a further aspect of the present invention there is provided a method of identifying a therapeutic antigenic gene sequence encoding a therapeutic antigenic protein of a disease, from a sample of nucleotide sequences. Preferably the marker is a polyHis tag.

6 Claims, 72 Drawing Sheets

FIGURE 1

Sequence 1. Represented by clone pAD612.

```
  1  atg gca aaa caa gat ttt tat aaa att ctg gga gtt gaa aaa tca
      M   A   K   Q   D   F   Y   K   I   L   G   V   E   K   S

 46  gca tca cta aca gaa ata aaa aaa gct tat cga aat tta gta aat
      A   S   L   T   E   I   K   K   A   Y   R   N   L   V   N

 91  att tat cat cct gat aaa aat aca aaa aaa tca gct gaa gaa caa
      I   Y   H   P   D   K   N   T   K   K   S   A   E   E   Q

136  aaa caa gct gag gcc aaa ttt aaa gaa atc cag gaa gcc tac gaa
      K   Q   A   E   A   K   F   K   E   I   Q   E   A   Y   E

181  att tta tct gat gaa aca aag cga aaa cag tac gat aaa ttc ggt
      I   L   S   D   E   T   K   R   K   Q   Y   D   K   F   G

226  cat gcc gct ttt gat cag caa ttt ggt ggt ggg tct agt ggc ttt
      H   A   A   F   D   Q   Q   F   G   G   G   S   S   G   F

271  tca gga ttt gat ttt ggc gat att ttt tca agt ttt acc tct ggt
      S   G   F   D   F   G   D   I   F   S   S   F   T   S   G

316  ttt ggt ttt ggc ggc tca caa gaa caa aaa tat agt cgt cct tta
      F   G   F   G   G   S   Q   E   Q   K   Y   S   R   P   L

351  aag ggc gaa aat ttt caa gct aaa att tat atc agt ttt atc gag
      K   G   E   N   F   Q   A   K   I   Y   I   S   F   I   E

406  tca att ctc gga aaa gaa atc tcc cag aaa tta aca aaa tac gat
      S   I   L   G   K   E   I   S   Q   K   L   T   K   Y   D

451  caa tgt gat aac tgt aag ggt tca ggc gct aat tct tct tct gat
      Q   C   D   N   C   K   G   S   G   A   N   S   S   S   D

496  att aca act tgc tat aat tgt caa ggt cgg gga atg caa act gag
      I   T   T   C   Y   N   C   Q   G   R   G   M   Q   T   E

541  gtc tta aat atc ccg gga ttt ggt cgg gtt cag aac aaa aca act
      V   L   N   I   P   G   F   G   R   V   Q   N   K   T   T

586  tgt tca gtt tgt tta ggt tcc ggg aaa aac att aca aaa att gca
      C   S   V   C   L   G   S   G   K   N   I   T   K   I   A

631  aag aag tgc cat gga aaa act ata gtt gag aca aaa gag gaa gta
      K   K   C   H   G   K   T   I   V   E   T   K   E   E   V

676  act att aaa att ccg gcc gga atc cag gat gga atg ttt atc cgc
```

```
      T   I   K   I   P   A   G   I   Q   D   G   M   F   I   R

721  gtg gcc gga ttt ggt gga ccg gga cac aaa ggc ggg cct tct gga
      V   A   G   F   G   G   P   G   H   K   G   G   P   S   G

766  gat ctt cat ctt gag att aat gtt cgt cag cat aaa cat ttt act
      D   L   H   L   E   I   N   V   R   Q   H   K   H   F   T

811  aga tcc gga aat gat att cat gtg aat atg cca gtt tca ata att
      R   S   G   N   D   I   H   V   N   M   P   V   S   I   I

856  gat att atc aac caa aat act gtc gaa gtt ccc aac cca acc ggt
      D   I   I   N   Q   N   T   V   E   V   P   N   P   T   G

901  ttg aaa aaa gtt aga ctt tat gat tat tat aaa tcc ggt cca att
      L   K   K   V   R   L   Y   D   Y   Y   K   S   G   P   I

946  gtt aat gtt ctt cct gct ggg gct cct gat cca aaa aat cca aga
      V   N   V   L   P   A   G   A   P   D   P   K   N   P   R

991  att att ggc gat ctc aag gtt cat tta att ttt tat atc ccc gaa
      I   I   G   D   L   K   V   H   L   I   F   Y   I   P   E

1036 ttt agt ccc cgt caa aaa gat gag ctc aac cag gtt ttt gct caa
      F   S   P   R   Q   K   D   E   L   N   Q   V   F   A   Q

1081 atc aat gat aaa aca aag gca aaa tga cta aaa gaa ttt caa
      I   N   D   K   T   K   A   K   W   L   K   E   F   Q
```

FIGURE 2

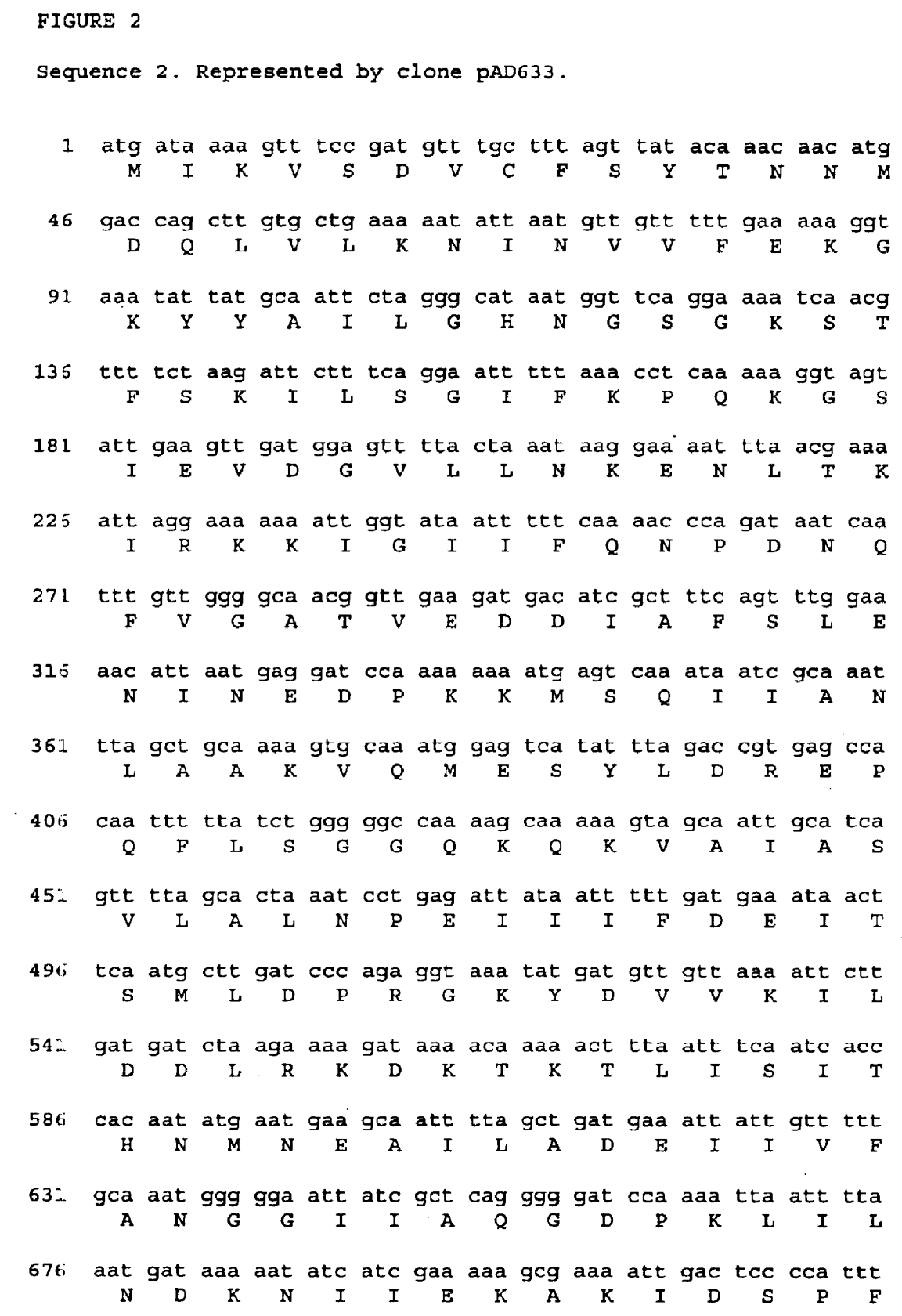

Sequence 2. Represented by clone pAD633.

```
  1  atg ata aaa gtt tcc gat gtt tgc ttt agt tat aca aac aac atg
      M   I   K   V   S   D   V   C   F   S   Y   T   N   N   M

 46  gac cag ctt gtg ctg aaa aat att aat gtt gtt ttt gaa aaa ggt
      D   Q   L   V   L   K   N   I   N   V   V   F   E   K   G

 91  aaa tat tat gca att cta ggg cat aat ggt tca gga aaa tca acg
      K   Y   Y   A   I   L   G   H   N   G   S   G   K   S   T

136  ttt tct aag att ctt tca gga att ttt aaa cct caa aaa ggt agt
      F   S   K   I   L   S   G   I   F   K   P   Q   K   G   S

181  att gaa gtt gat gga gtt tta cta aat aag gaa aat tta acg aaa
      I   E   V   D   G   V   L   L   N   K   E   N   L   T   K

226  att agg aaa aaa att ggt ata att ttt caa aac cca gat aat caa
      I   R   K   K   I   G   I   I   F   Q   N   P   D   N   Q

271  ttt gtt ggg gca acg gtt gaa gat gac atc gct ttc agt ttg gaa
      F   V   G   A   T   V   E   D   D   I   A   F   S   L   E

316  aac att aat gag gat cca aaa aaa atg agt caa ata atc gca aat
      N   I   N   E   D   P   K   K   M   S   Q   I   I   A   N

361  tta gct gca aaa gtg caa atg gag tca tat tta gac cgt gag cca
      L   A   A   K   V   Q   M   E   S   Y   L   D   R   E   P

406  caa ttt tta tct ggg ggc caa aag caa aaa gta gca att gca tca
      Q   F   L   S   G   G   Q   K   Q   K   V   A   I   A   S

451  gtt tta gca cta aat cct gag att ata att ttt gat gaa ata act
      V   L   A   L   N   P   E   I   I   I   F   D   E   I   T

496  tca atg ctt gat ccc aga ggt aaa tat gat gtt gtt aaa att ctt
      S   M   L   D   P   R   G   K   Y   D   V   V   K   I   L

541  gat gat cta aga aaa gat aaa aca aaa act tta att tca atc acc
      D   D   L   R   K   D   K   T   K   T   L   I   S   I   T

586  cac aat atg aat gaa gca att tta gct gat gaa att att gtt ttt
      H   N   M   N   E   A   I   L   A   D   E   I   I   V   F

631  gca aat ggg gga att atc gct cag ggg gat cca aaa tta att tta
      A   N   G   G   I   I   A   Q   G   D   P   K   L   I   L

676  aat gat aaa aat atc atc gaa aaa gcg aaa att gac tcc cca ttt
      N   D   K   N   I   I   E   K   A   K   I   D   S   P   F
```

```
721  atc tat aaa att tcc agc gca ctt aaa tta gtt agt cca act tat
      I   Y   K   I   S   S   A   L   K   L   V   S   P   T   Y

766  gac gaa aat gaa ttg cta gag caa cta tga aaa tta aag caa aaa
      D   E   N   E   L   L   E   Q   L   W   K   L   K   Q   K

811  aca tcg
      T   S
```

FIGURE 3

Sequence 3. Represented by clone pAD639.

```
  1  atg ttt agt caa act att tat aaa tga aaa agc gaa aat ctc gaa
      M   F   S   Q   T   I   Y   K   W   K   S   E   N   L   E

 46  aga gtg gtc gtc cct gaa aaa gga ctt tct tgc gaa tat aac ggt
      R   V   V   V   P   E   K   G   L   S   C   E   Y   N   G

 91  ctt ttt agc ata aga act ggc aaa agt ttg tac ggg ctg cta caa
      L   F   S   I   R   T   G   K   S   L   Y   G   L   L   Q

136  aat tta gat aat gat tat ttt att gct tac cta aga tca agt gtg
      N   L   D   N   D   Y   F   I   A   Y   L   R   S   S   V

181  ctt atc ttt acc tct tcc gca tca tcc gct tta gta aga gca aag
      L   I   F   T   S   S   A   S   S   A   L   V   R   A   K

226  tct tat tgc gaa aac gat ttt tga ttg cat aaa aat aat ttt tta
      S   Y   C   E   N   D   F   W   L   H   K   N   N   F   L

271  gtc ggc ctt atc gtc ttt agt gcc gga att ttt aaa ata atg gat
      V   G   L   I   V   F   S   A   G   I   F   K   I   M   D

316  ggt aga tga gaa aat acc tat ctt gtt aaa tca ggg gat ggt ttt
      G   R   W   E   N   T   Y   L   V   K   S   G   D   G   F

361  aac cgg ttt tta caa gaa cta aaa agc aaa aaa cac tat aaa tta
      N   R   F   L   Q   E   L   K   S   K   K   H   Y   K   L

406  gaa tgt ttt ttg ctt tca aac tta ttt ttt gtc agc ctg agt cta
      E   C   F   L   L   S   N   L   F   F   V   S   L   S   L

451  act aat cat atc aga agt cta gcc cat cca gat tta aat aat tca
```

```
         T   N   H   I   R   S   L   A   H   P   D   L   N   N   S

496     act att tat tta aat gaa tta tgc ctt gat gat ctt agt caa aaa
         T   I   Y   L   N   E   L   C   L   D   D   L   S   Q   K

541     gaa act tta gct cta aaa agt ctt gga aat tat gat ttt gac gat
         E   T   L   A   L   K   S   L   G   N   Y   D   F   D   D

586     caa gaa aag gaa ctt tta gag atc
         Q   E   K   E   L   L   E   I
```

FIGURE 4

Sequence 4. Represented by clone pAD640.

```
  1  gag gta agc acg att ccc gga cga ggc gat att aaa cta aca ggt
      E   V   S   T   I   P   G   R   G   D   I   K   L   T   G

 46  tcg ctt aag gat gta atg caa gaa tca gcc cgg att gcc ctt tct
      S   L   K   D   V   M   Q   E   S   A   R   I   A   L   S

 91  tat gtt cag tca aag gcc aag gat ttt ggg att aat ttt gat ttt
      Y   V   Q   S   K   A   K   D   F   G   I   N   F   D   F

136  gaa aac act tta att cat att cat gta ccc gaa gga gca att cca
      E   N   T   L   I   H   I   H   V   P   E   G   A   I   P

181  aaa gat ggg cca tca gca ggg ata act ttt gca aca gca ata att
      K   D   G   P   S   A   G   I   T   F   A   T   A   I   I

226  tca gcc ctc tcg caa aag ccg gtc tca cat aat att gca atg aca
      S   A   L   S   Q   K   P   V   S   H   N   I   A   M   T

271  ggg gag ata acc ttg cgc ggg aag gtt tta gca atc ggc gga cta
      G   E   I   T   L   R   G   K   V   L   A   I   G   G   L

316  aaa gaa aag acg atg ggg gcc tat tta aat ggg att aaa att att
      K   E   K   T   M   G   A   Y   L   N   G   I   K   I   I

361  ttt att ccc aag gcg aac gag aaa aat tta gtc gat att ccg cag
      F   I   P   K   A   N   E   K   N   L   V   D   I   P   Q

406  gaa gta aaa gac gtt atc cag ttt att ccc gtt gat act tat caa
      E   V   K   D   V   I   Q   F   I   P   V   D   T   Y   Q

451  cca att tat gat ttt att ttt
      P   I   Y   D   F   I   F
```

FIGURE 5

Sequence 5. Represented by clones pAD641 and pAD1033.

```
  1 aaa aaa ctt tta gat act tta ggg gct gaa ttt agt cca aaa gca
     K   K   L   L   D   T   L   G   A   E   F   S   P   K   A

 46 ctt gtt tct tcg ctt tcg atc tca caa aag caa ttt atc gaa atc
     L   V   S   S   L   S   I   S   Q   K   Q   F   I   E   I

 91 gcc aaa gct tta tcc caa aaa ccg gaa att atc att ttt gat gaa
     A   K   A   L   S   Q   K   P   E   I   I   I   F   D   E

136 ccg act tcg gtt cta acc gaa aaa gat acc caa aaa ctt tat ctg
     P   T   S   V   L   T   E   K   D   T   Q   K   L   Y   L

181 ctt gtt gaa aaa ctt aaa aaa caa gga att gca atc gtc tga att
     L   V   E   K   L   K   K   Q   G   I   A   I   V   W   I

226 acc cat aga atg gaa gaa att aag aaa act tgt gaa ttt atc act
     T   H   R   M   E   E   I   K   K   T   C   E   F   I   T

271 gtg att cga aac gga atg tat att gaa agt aag cca ata aat gaa
     V   I   R   N   G   M   Y   I   E   S   K   P   I   N   E

316 ttt aaa aac gaa gat gag att att tct tta atg gtc ggt ttt gat
     F   K   N   E   D   E   I   I   S   L   M   V   G   F   D

361 atc gag cag cgc tat ccc gaa aaa acg ccg gtt aga agt aaa aaa
     I   E   Q   R   Y   P   E   K   T   P   V   R   S   K   K

406 cca tcg ttt tta gtt aga aat tta tca aat gat aaa gtt tct aat
     P   S   F   L   V   R   N   L   S   N   D   K   V   S   N

451 atc agt ttt gaa atc aaa cca ggt gaa att tta gtt ttt tat ggc
     I   S   F   E   I   K   P   G   E   I   L   V   F   Y   G

496 ctt gta agt tca ggt cga act gaa tta gct aga act tta att ggc
     L   V   S   S   G   R   T   E   L   A   R   T   L   I   G

541 gat atg cct tat tta aat ggt cat att gaa cta aat ggt caa gaa
     D   M   P   Y   L   N   G   H   I   E   L   N   G   Q   E

586 ttt cgc cca aaa aat att aag gac agt ctt gat cat gga att tat
     F   R   P   K   N   I   K   D   S   L   D   H   G   I   Y

631 tat ctt tct gaa aat agg aaa caa att ggt cta aat gtt aat tta
     Y   L   S   E   N   R   K   Q   I   G   L   N   V   N   L

676 cca att aat ttt aat atc aca att tct tct ctt ggc tca aat cag
```

```
      P   I   N   F   N   I   T   I   S   S   L   G   S   N   Q

721   att ttt tct ttc ctt cct ttt gtc tca aaa gca aaa ata act aaa
       I   F   S   F   L   P   F   V   S   K   A   K   I   T   K

766   act aca aat cat tat att aaa caa tta aag atc aaa aca act tca
       T   T   N   H   Y   I   K   Q   L   K   I   K   T   T   S

811   caa gat acg cca tta act tct tta tca ggt gga aat caa caa aaa
       Q   D   T   P   L   T   S   L   S   G   G   N   Q   Q   K

856   gtt tca ctt gca aaa ggg ctt gca acc caa ccg caa gtt ttc atc
       V   S   L   A   K   G   L   A   T   Q   P   Q   V   F   I

901   ctc gat gaa cca act cgc gga gtc gat gtt ggc gca aga aag gaa
       L   D   E   P   T   R   G   V   D   V   G   A   R   K   E

946   att tat aat tta att cac caa tta aaa caa gaa aat aaa aca att
       I   Y   N   L   I   H   Q   L   K   Q   E   N   K   T   I

991   atg ata att tct tcg gat atg caa gag gtt atc gga atc gct gat
       M   I   I   S   S   D   M   Q   E   V   I   G   I   A   D

1036  cgg gta att aca atg tat gaa ggc aga att aca agt gaa tta gtt
       R   V   I   T   M   Y   E   G   R   I   T   S   E   L   V

1081  ggc ccg caa att acc gat caa aat ata atg aaa tat tca ctt aat
       G   P   Q   I   T   D   Q   N   I   M   K   Y   S   L   N

1126  tta
       L
```

FIGURE 6

Sequence 6. Represented by clone pAD653.

```
  1  aca gtc gga att aac aaa acc gaa atg gat gca aat acc aaa aga
      T   V   G   I   N   K   T   E   M   D   A   N   T   K   R

 46  atg atg tat aat gcc gat att act tat tcg gtt cat tct gaa tta
      M   M   Y   N   A   D   I   T   Y   S   V   H   S   E   L

 91  ggt ttt gat tat ctc cgg gat aat atg gtt ttt tca gca gct gaa
      G   F   D   Y   L   R   D   N   M   V   F   S   A   A   E

136  aaa gtt caa agg gga cta aat ttt tgc cta atc gat gaa gta gac
      K   V   Q   R   G   L   N   F   C   L   I   D   E   V   D

181  tca att ttg atc gat gaa gcc aaa acc cct ttg att atc agt ggt
      S   I   L   I   D   E   A   K   T   P   L   I   I   S   G

226  ggc aaa act aac ctt cca gcc caa tat tta tcc gcg aac caa ttt
      G   K   T   N   L   P   A   Q   Y   L   S   A   N   Q   F

271  gtt aat act cta att gct gaa gat ttt tat att gat gaa gaa act
      V   N   T   L   I   A   E   D   F   Y   I   D   E   E   T

316  aag gga att aaa tta aat gat aaa gga atc gat aag gca aat gct
      K   G   I   K   L   N   D   K   G   I   D   K   A   N   A

361  ttt ttt ggc ctt cgt aat tta tat gaa att caa aac tca gaa ata
      F   F   G   L   R   N   L   Y   E   I   Q   N   S   E   I

406  gtt cat cga att caa aac gcg ctg aga gcc aat aag gtg atg aaa
      V   H   R   I   Q   N   A   L   R   A   N   K   V   M   K

451  cgc gat gtt gaa tat att gtc cag gac ggc aaa att gcc tta gtt
      R   D   V   E   Y   I   V   Q   D   G   K   I   A   L   V

496  gat caa ttt act ggg cga att atg gct gga aga tct tat tct gaa
      D   Q   F   T   G   R   I   M   A   G   R   S   Y   S   E

541  ggt ctc cag caa gcc ctg caa gca aaa gag ggg ctt gaa att gaa
      G   L   Q   Q   A   L   Q   A   K   E   G   L   E   I   E

586  cct gag aca aaa aca cta gca aca att acc tat caa aat ttt ttt
      P   E   T   K   T   L   A   T   I   T   Y   Q   N   F   F

631  cgc ctt ttt aaa aaa tta tca ggg atg acc ggg act gcc aaa acc
      R   L   F   K   K   L   S   G   M   T   G   T   A   K   T

676  gaa gaa caa gaa ttt atc gat gtt tat aat atg cgc gtg aat gtg
      E   E   Q   E   F   I   D   V   Y   N   M   R   V   N   V
```

```
721  att ccg aca aac aaa ccg atg att cgt aag gat gaa aaa gat gaa
      I   P   T   N   K   P   M   I   R   K   D   E   K   D   E

766  att ttt gcc act agt cac gaa aaa aat caa gct ata att tcc gaa
      I   F   A   T   S   H   E   K   N   Q   A   I   I   S   E

811  gtt gaa cgt gtt cat aaa atg ggg cag cca att tta att gga acc
      V   E   R   V   H   K   M   G   Q   P   I   L   I   G   T

856  tca caa gtt gtt gac tct gaa acg ctt tcg gag atg cta aac caa
      S   Q   V   V   D   S   E   T   L   S   E   M   L   N   Q

901  aaa gga ctt tat cat aca gta tta aat gca aaa caa aac caa ctt
      K   G   L   Y   H   T   V   L   N   A   K   Q   N   Q   L

946  gaa gcc gaa att att gcc cag gca gga cga aaa aat gcg att acc
      E   A   E   I   I   A   Q   A   G   R   K   N   A   I   T

991  atc gcg aca aat atg gct gga aga aga act gat ata att tta gag
      I   A   T   N   M   A   G   R   R   T   D   I   I   L   E

1036 cct ggt gtg act gaa ctt ggg cgg ctt tat att ctt gga acc gat
      P   G   V   T   E   L   G   R   L   Y   I   L   G   T   D

1081 aaa gcc gaa act aga aga atc gat aac caa cta cga ggt cgc tct
      K   A   E   T   R   R   I   D   N   Q   L   R   G   R   S

1126 gga cga caa ggt gat gtg gga att tcg cga ttt ttt atc tca ctt
      G   R   Q   G   D   V   G   I   S   R   F   F   I   S   L

1171 cag gac caa ctt ttt cgg cgt ttt acc aat ttt gat caa att ttt
      Q   D   Q   L   F   R   R   F   T   N   F   D   Q   I   F

1216 ggc gct tat gga caa aca aat ggg gca att aaa gga aaa tat att
      G   A   Y   G   Q   T   N   G   A   I   K   G   K   Y   I

1261 cat gcg gtt tta ctt gca gcc caa aag aaa atc gaa ggc ttt aac
      H   A   V   L   L   A   A   Q   K   K   I   E   G   F   N

1306 ttc gat atg cgc aaa act gtg ctt agt tat gat gat gtt att cgt
      F   D   M   R   K   T   V   L   S   Y   D   D   V   I   R

1351 caa cag cgt gat tta att tat gcc caa aga gat att ttg ctt cag
      Q   Q   R   D   L   I   Y   A   Q   R   D   I   L   L   Q

1396 att gaa aat ttt gac cat tat atc cag aag atg att att cgg gct
      I   E   N   F   D   H   Y   I   Q   K   M   I   I   R   A

1441 gtt gat atc att tta agc tat gat ttt ata att tta cca aat caa
      V   D   I   I   L   S   Y   D   F   I   I   L   P   N   Q
```

```
1486 gaa att cac tat aaa aat tta ata aat ttt ctt aat gat aat tta
      E   I   H   Y   K   N   L   I   N   F   L   N   D   N   L

1531 tca aga att act cat ttt aac ttt ggg caa att gga att gaa aat
      S   R   I   T   H   F   N   F   G   Q   I   G   I   E   N

1576 tat ccc att gaa caa ctt aat gaa ttt tta atc aaa caa tta gaa
      Y   P   I   E   Q   L   N   E   F   L   I   K   Q   L   E

1621 act att tat ttt aaa caa atc caa tca gtt tta aag gaa aat ctt
      T   I   Y   F   K   Q   I   Q   S   V   L   K   E   N   L

1666 gga aaa acc tac ttt gaa tca gaa cgt tat att att tta tca aca
      G   K   T   Y   F   E   S   E   R   Y   I   I   L   S   T

1711 ctt gat agt cag tga caa aat cat att gac acc att gac aaa tta
      L   D   S   Q   W   Q   N   H   I   D   T   I   D   K   L

1756 aga tct tct gct aat tta gtt cag tat tcc cag aaa aat cct tat
      R   S   S   A   N   L   V   Q   Y   S   Q   K   N   P   Y

1801 caa att ttt acc gag gaa gca aca aaa aaa ttc aac att tta gta
      Q   I   F   T   E   E   A   T   K   K   F   N   I   L   V

1846 gca gaa tcc gct tat cag gca ata gtt tct tta ttt aat aat tca
      A   E   S   A   Y   Q   A   I   V   S   L   F   N   N   S

1891 aat gct gaa aaa ata gaa tat atc aaa gca att ttg tct gat gga
      N   A   E   K   I   E   Y   I   K   A   I   L   S   D   G

1936 acc gca att tct tat ccg gca gat agc cct caa gaa ata att gat
      T   A   I   S   Y   P   A   D   S   P   Q   E   I   I   D

1981 caa ata atc gcc tct aac gag gag aga atc gcg gct gca aga aaa
      Q   I   I   A   S   N   E   E   R   I   A   A   A   R   K

2026 gca aaa gaa gaa aaa cag cct gaa ttt att gaa aaa caa ctt gct
      A   K   E   E   K   Q   P   E   F   I   E   K   Q   L   A

2071 aaa cta aaa att gaa aag gtt gaa tca gga gag gaa ttt gaa ctt
      K   L   K   I   E   K   V   E   S   G   E   E   F   E   L

2116 tga aaa atc gga gat agc aaa cta gtt aac cta aaa aag gaa atg
      W   K   I   G   D   S   K   L   V   N   L   K   K   E   M

2161 cct ctt gat gaa aaa caa aat att tta gta aaa atg cag cag gaa
      P   L   D   E   K   Q   N   I   L   V   K   M   Q   Q   E

2206 caa ctt gaa atg atg agc gag gaa gaa aaa aac cta ata caa gaa
      Q   L   E   M   M   S   E   E   E   K   N   L   I   Q   E

2251 caa aat tta gag att gta gag att gaa gaa ata gag gaa gaa att
```

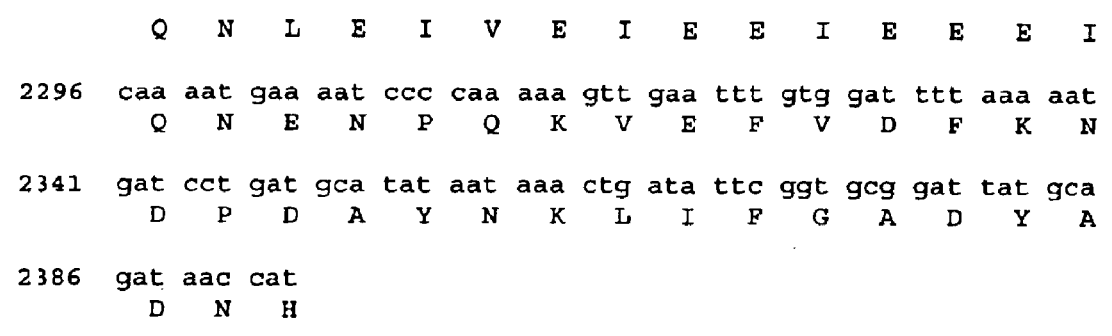

```
        Q   N   L   E   I   V   E   I   E   E   I   E   E   E   I

2296   caa aat gaa aat ccc caa aaa gtt gaa ttt gtg gat ttt aaa aat
        Q   N   E   N   P   Q   K   V   E   F   V   D   F   K   N

2341   gat cct gat gca tat aat aaa ctg ata ttc ggt gcg gat tat gca
        D   P   D   A   Y   N   K   L   I   F   G   A   D   Y   A

2386   gat aac cat
        D   N   H
```

FIGURE 7

Sequence 7. Represented by clones pAD657 and pAD964.

```
  1  atg att tcg tat ttt tat tca aaa tca gca ccg cag tgt ctt aaa
      M   I   S   Y   F   Y   S   K   S   A   P   Q   C   L   K

 46  act gaa aat ccc aga ttt tgt tat aaa cta aat aaa aat tta gta
      T   E   N   P   R   F   C   Y   K   L   N   K   N   L   V

 91  aaa ttt caa aaa gaa tta gat cta tta aaa cag aaa aaa ctt gca
      K   F   Q   K   E   L   D   L   L   K   Q   K   K   L   A

136  cca aaa gaa tat gaa agc cag ttt agt gat cta aaa gaa aaa ttt
      P   K   E   Y   E   S   Q   F   S   D   L   K   E   K   F

181  tta gct tat gaa gtt aat ata aaa aaa cat tat cag gca aaa aaa
      L   A   Y   E   V   N   I   K   K   H   Y   Q   A   K   K

226  tcc tat aaa tta cgt gct att tga gat cgg att caa aaa tat tga
      S   Y   K   L   R   A   I   W   D   R   I   Q   K   Y   W

271  cat aca agc ttt aac aga tcc cat ttt gat ttt gaa gca ttt tct
      H   T   S   F   N   R   S   H   F   D   F   E   A   F   S

316  aaa aat gtt gaa tat aaa caa ata gga aat aaa cgt cat aaa att
      K   N   V   E   Y   K   Q   I   G   N   K   R   H   K   I

361  gtt gcc cgg atc aaa aat tta aac ctt tcc ttt gtc aat cca gca
      V   A   R   I   K   N   L   N   L   S   F   V   N   P   A

406  aat ccc gag att aga aat atc gtg att cgt aat gcc tca att gat
      N   P   E   I   R   N   I   V   I   R   N   A   S   I   D

451  ttt tat gaa ggc gaa att cat gcc tta att ggc gag tct ggt tca
      F   Y   E   G   E   I   H   A   L   I   G   E   S   G   S

496  gga aaa tca gta att act tct tgt ctt tat ggt ctt gtc ggt caa
      G   K   S   V   I   T   S   C   L   Y   G   L   V   G   Q

541  aac ggg gta att gaa tca ggt gaa atc aaa ctt ttt aac aat cca
      N   G   V   I   E   S   G   E   I   K   L   F   N   N   P

586  gtg caa aat ttt gat ttt cgt gct tga gaa ctt tca aat tat cgg
      V   Q   N   F   D   F   R   A   W   E   L   S   N   Y   R

631  gga aaa gtt att tca gct gtc ttc cag aat ccg atg tca act tta
      G   K   V   I   S   A   V   F   Q   N   P   M   S   T   L

676  aat cca aca aaa aaa ata ggc atc caa att atg gaa gga atg tta
      N   P   T   K   K   I   G   I   Q   I   M   E   G   M   L
```

```
721  tta aac aag att gtt aaa acg aaa aaa gaa gcc tat gaa aaa gca
      L   N   K   I   V   K   T   K   K   E   A   Y   E   K   A

766  ctt tta tat ctt aga atg acc aaa att gct aac ccg gaa atg gtt
      L   L   Y   L   R   M   T   K   I   A   N   P   E   M   V

811  atg aaa tta tat ccc cat gag ctt tca gga ggt atg att caa aga
      M   K   L   Y   P   H   E   L   S   G   G   M   I   Q   R

856  att gtg atc tca gca att tta tca ctt gaa cct aaa att atc gtt
      I   V   I   S   A   I   L   S   L   E   P   K   I   I   V

901  atg gat gaa cca aca aca gct ttg gat aca acc gtg caa gct tta
      M   D   E   P   T   T   A   L   D   T   T   V   Q   A   L

946  gtt ctt gat att atc cgc gat ctc caa aaa aga cta aaa att aca
      V   L   D   I   I   R   D   L   Q   K   R   L   K   I   T

991  att att ttc att act cac gac ctt gga gtt gtc gct tct ctt gca
      I   I   F   I   T   H   D   L   G   V   V   A   S   L   A

1036 act tat atc tca atc atg tat gct ggt caa gtt gtc gag gaa ggt
      T   Y   I   S   I   M   Y   A   G   Q   V   V   E   E   G

1081 aca aga gat gaa att ctt tta aat cca aga cat cca tat act tga
      T   R   D   E   I   L   L   N   P   R   H   P   Y   T   W

1126 ggg cta att act tca atg cct gat gtc aat aaa ggc gaa cga ctt
      G   L   I   T   S   M   P   D   V   N   K   G   E   R   L

1171 cag tca att cgc ggg gtt gtt cct tct tct tta aat tca att gtt
      Q   S   I   R   G   V   V   P   S   S   L   N   S   I   V

1216 ggc gat gct ttt gca gtt aga aac gat tat gcc tta gaa caa gat
      G   D   A   F   A   V   R   N   D   Y   A   L   E   Q   D

1261 ttt ttt att gaa cct aaa ttt tac aga ata agt cca act cac cga
      F   F   I   E   P   K   F   Y   R   I   S   P   T   H   R

1306 gtc aaa tca gct tta ctt gat cca aaa gca cca aaa gtt gtc cca
      V   K   S   A   L   L   D   P   K   A   P   K   V   V   P

1351 cca aaa att att tac caa aaa tga ctg caa ttt gca aag atg agg
      P   K   I   I   Y   Q   K   W   L   Q   F   A   K   M   R

1396 caa gaa aat gga aga
      Q   E   N   G   R
```

FIGURE 8

Sequence 8. Represented by clones pAD659 and pAD910.

```
  1  atg aaa aat att gaa aaa agt gaa ata att atc tcc ctt gtt gat
      M   K   N   I   E   K   S   E   I   I   I   S   L   V   D

 46  gtt gat aaa gaa ttt ggt gat aaa aaa gtt tta gat caa ata aat
      V   D   K   E   F   G   D   K   K   V   L   D   Q   I   N

 91  ttg gac att aaa cga gga gat ttt gtc aca ctt tta ggg ccc tca
      L   D   I   K   R   G   D   F   V   T   L   L   G   P   S

136  ggg tcc ggg aag aca aca att tta cgt tta att ggt ggt ttt gaa
      G   S   G   K   T   T   I   L   R   L   I   G   G   F   E

181  tga act act cgc ggc gaa atc aaa ttt aat ggc atc gat ata aaa
      W   T   T   R   G   E   I   K   F   N   G   I   D   I   K

226  gac gtt ccg gca cat aaa cgt gat aca gct aca att ttt caa gat
      D   V   P   A   H   K   R   D   T   A   T   I   F   Q   D

271  tat gca ctt ttt cca cat tta tca gtt cgt gga aat att gaa ttt
      Y   A   L   F   P   H   L   S   V   R   G   N   I   E   F

316  ggt ctt aaa tta aaa aga att aaa aaa aag gca gaa gaa att ccg
      G   L   K   L   K   R   I   K   K   K   A   E   E   I   P

361  gat gta gtc tgg aaa aaa ttt gag cac tta aag aaa aaa tga cag
      D   V   V   W   K   K   F   E   H   L   K   K   K   W   Q

406  gat aag caa aag cga aag att aaa gag tta aaa att tta cag gct
      D   K   Q   K   R   K   I   K   E   L   K   I   L   Q   A

451  cat tta gaa aaa ctg ctt gaa aat cca cag tta gat att aaa aaa
      H   L   E   K   L   L   E   N   P   Q   L   D   I   K   K

496  cgt aaa aaa tta cag gat aaa tta gat gat tct gat ttt aga tat
      R   K   K   L   Q   D   K   L   D   D   S   D   F   R   Y

541  tca aat tga gaa aat tat cta aca tcc aaa tca gaa agt ttt aaa
      S   N   W   E   N   Y   L   T   S   K   S   E   S   F   K

586  aaa aaa tac cta acc cga aag atc aca aaa cag gaa att aat aaa
      K   K   Y   L   T   R   K   I   T   K   Q   E   I   N   K

631  gaa att acc gat att att gac ctt gtt ggt cta act gga aat gaa
      E   I   T   D   I   I   D   L   V   G   L   T   G   N   E

676  aat cga gca att tcg gaa tta tca gga gga atg aaa caa cgc gta
      N   R   A   I   S   E   L   S   G   G   M   K   Q   R   V
```

```
721   gca ctt gca aga tcg ctt gta att gag cct gaa att gtc cta ctt
       A   L   A   R   S   L   V   I   E   P   E   I   V   L   L

766   gat gaa cct tta tca gct tta gat aca aaa att agg caa aaa atg
       D   E   P   L   S   A   L   D   T   K   I   R   Q   K   M

811   caa gtt ttt cta aaa aaa att caa caa aaa ctt ggc cta act ttt
       Q   V   F   L   K   K   I   Q   Q   K   L   G   L   T   F

856   att ttt gtt act cat gat caa gat gaa gcc ttg caa tta tca gat
       I   F   V   T   H   D   Q   D   E   A   L   Q   L   S   D

901   aaa atc gcc ata atc cgt aat gga aaa atc gcc caa tac gat gaa
       K   I   A   I   I   R   N   G   K   I   A   Q   Y   D   E

946   cca aaa caa att tat gac tat cca gtt aat aaa tgg gtg gct aat
       P   K   Q   I   Y   D   Y   P   V   N   K   W   V   A   N

991   ttt att ggt gat tct aat ttt ttt cag gca aaa tac att aaa aaa
       F   I   G   D   S   N   F   F   Q   A   K   Y   I   K   K

1036  aat cag gtc gaa att ctt ggt ctt aaa tta tat aca att cat gat
       N   Q   V   E   I   L   G   L   K   L   Y   T   I   H   D

1081  gag ttt atc cca ggc caa aaa tta gat tgc ctg att cgt cca gaa
       E   F   I   P   G   Q   K   L   D   C   L   I   R   P   E

1126  gat atc gat att gac cta aat tca ggc tat ttt aaa gga aaa gtt
       D   I   D   I   D   L   N   S   G   Y   F   K   G   K   V

1171  atc caa aat att tat aaa ggt tca tac tat tca ctt gat atc aaa
       I   Q   N   I   Y   K   G   S   Y   Y   S   L   D   I   K

1216  gta gaa aat aca ata att aat gtc gaa act aac gat ttt tat gac
       V   E   N   T   I   I   N   V   E   T   N   D   F   Y   D

1261  ctc gag act caa gtt ttt cta aaa tga gat gat gat gct att cat
       L   E   T   Q   V   F   L   K   W   D   D   D   A   I   H

1306  tta atg gag atg gaa aat gct gaa att
       L   M   E   M   E   N   A   E   I
```

FIGURE 9

Sequence 9. Represented by clone pAD662.

```
  1  gat att aaa ttg aaa aaa act aat att cta tca cta aaa aaa ata
      D   I   K   L   K   K   T   N   I   L   S   L   K   K   I

 46  aaa aaa gtt tat ggt cct gta att gct ctt tct gat gtg act ttt
      K   K   V   Y   G   P   V   I   A   L   S   D   V   T   F

 91  gtt gtt cca aaa ggg gaa ata act agc cta gtt ggt gaa aat ggc
      V   V   P   K   G   E   I   T   S   L   V   G   E   N   G

136  gcg gga aaa tcg aca ctt tta aaa att tta tca gga gtg att cct
      A   G   K   S   T   L   L   K   I   L   S   G   V   I   P

181  gct gga caa tat gaa ggt gat cta att ttt gaa gat aaa att atg
      A   G   Q   Y   E   G   D   L   I   F   E   D   K   I   M

226  gct ttt gca aat aca aaa gcc tcc gaa cgt gtc gga att gca ata
      A   F   A   N   T   K   A   S   E   R   V   G   I   A   I

271  att cat caa gaa ctt tca att tca cct tat tta tca att tgc gag
      I   H   Q   E   L   S   I   S   P   Y   L   S   I   C   E

316  aac atg tat atc ggt aat tat ccg act aaa ttt ggc aaa gtt aac
      N   M   Y   I   G   N   Y   P   T   K   F   G   K   V   N

361  tga aat aag atg att tcc gaa tgc aaa aaa tat cta gaa atg gtc
      W   N   K   M   I   S   E   C   K   K   Y   L   E   M   V

406  ggt ctt gat gaa gat cca aca aca att gct ggc tct ctt tcg att
      G   L   D   E   D   P   T   T   I   A   G   S   L   S   I

451  gca aaa cag caa atg gtt gag atc gca aaa gca ctt tca aaa aat
      A   K   Q   Q   M   V   E   I   A   K   A   L   S   K   N

496  gca aaa cta cta att tta gat gaa ccg act tcc tct tta aat gat
      A   K   L   L   I   L   D   E   P   T   S   S   L   N   D

541  gaa aat gct ttt cgc tta ctt gat att atg aaa agt tta aaa agt
      E   N   A   F   R   L   L   D   I   M   K   S   L   K   S

586  aaa gga att act tcg att ttt gtc tcc cat aaa tta aat gaa gtc
      K   G   I   T   S   I   F   V   S   H   K   L   N   E   V

631  aaa tat gtc tct gat aat att gtt gta atc cgc gat ggt aaa ttc
      K   Y   V   S   D   N   I   V   V   I   R   D   G   K   F

676  att tcc cag tat aat aaa aat gaa gaa ata att gat gaa aac cgg
      I   S   Q   Y   N   K   N   E   E   I   I   D   E   N   R
```

```
 721  cta att cag gac att gtt ggc cgg cct tta aag tcc aaa ttt cct
       L   I   Q   D   I   V   G   R   P   L   K   S   K   F   P

 766  cct agg gat tta gat cga aaa atc ggg gaa att att ttt gag atc
       P   R   D   L   D   R   K   I   G   E   I   I   F   E   I

 811  aaa gat ata gtt att cct cat gct agt att gca aat tat aat gtt
       K   D   I   V   I   P   H   A   S   I   A   N   Y   N   V

 856  gtc aaa aat gct tcc ctt gat gtt aaa caa ggc gaa att gtc gga
       V   K   N   A   S   L   D   V   K   Q   G   E   I   V   G

 901  att tcc gga ctt gtt gga tcg ggt cga acc gaa tta atg ctt tca
       I   S   G   L   V   G   S   G   R   T   E   L   M   L   S

 946  ctt ttt ggg cag tat tat aac aaa cct tca agt ggc aaa gtt ttc
       L   F   G   Q   Y   Y   N   K   P   S   S   G   K   V   F

 991  tat aaa ggt aaa gaa gta aaa ttt act aac aca aaa cag gca atc
       Y   K   G   K   E   V   K   F   T   N   T   K   Q   A   I

1036  aaa tcg gga att atg tat gct tcc gaa gat cga aaa aat gtt ggt
       K   S   G   I   M   Y   A   S   E   D   R   K   N   V   G

1081  cta atc caa att ttt tcg att caa aat aat atc act tcc gcc gct
       L   I   Q   I   F   S   I   Q   N   N   I   T   S   A   A

1126  ttg cat tta ttt tca aaa tga gga att cta aat aaa aat aag gaa
       L   H   L   F   S   K   W   G   I   L   N   K   N   K   E

1171  ata att aat gcc caa aaa cta aaa aaa gat gta agt att aaa aca
       I   I   N   A   Q   K   L   K   K   D   V   S   I   K   T

1216  aaa aat att cta aat aat gtc gaa tcc ctt tct ggg gga aat cag
       K   N   I   L   N   N   V   E   S   L   S   G   G   N   Q

1261  caa aaa gtt gta att gcc aaa gct tta agc acc aaa ttt gac ctt
       Q   K   V   V   I   A   K   A   L   S   T   K   F   D   L

1306  cta att atc gat gag cca aca aaa ggt att gat gtt ggc tca aaa
       L   I   I   D   E   P   T   K   G   I   D   V   G   S   K

1351  tac gaa att tat aaa att tta cta gac ctt tca tca caa ggt aaa
       Y   E   I   Y   K   I   L   L   D   L   S   S   Q   G   K

1396  aca att att gta atc tct tcg gaa att gaa gaa ctt tta gga atc
       T   I   I   V   I   S   S   E   I   E   E   L   L   G   I

1441  acc gat cac ctt tat ttt gtg act gga aaa ctt ttt ggt caa aat
       T   D   H   L   Y   F   V   T   G   K   L   F   G   Q   N
```

```
1486  caa gac tga ctt tcc cag ttt ttg cat ctt ttt tat aac ttt ttt
       Q   D   W   L   S   Q   F   L   H   L   F   Y   N   F   F

1531  gac caa aag gat tac cat aag gac ttc caa att ttg aga cat aat
       D   Q   K   D   Y   H   K   D   F   Q   I   L   R   H   N

1576  ctt ggt gaa gcg agt
       L   G   E   A   S
```

FIGURE 10

Sequence 10. Represented by clone pAD681.

```
  1  atc gaa acc atc aaa att gag ctg ggt gag cag ctc gaa ttt ttt
      I   E   T   I   K   I   E   L   G   E   Q   L   E   F   F

 46  gaa aaa aat aat aaa tta gtc gaa aaa caa cga cta aaa gac cga
      E   K   N   N   K   L   V   E   K   Q   R   L   K   D   R

 91  gtc aat aat gat att gac tcg ctt tct gaa ttc gga att tgt tca
      V   N   N   D   I   D   S   L   S   E   F   G   I   C   S

136  gga att gag aat tat gcc cgc cat att gac gga cgc caa aaa ggc
      G   I   E   N   Y   A   R   H   I   D   G   R   Q   K   G

181  gaa aaa cca ttt agt tta cta gat tat tta ccc caa gac ggc cta
      E   K   P   F   S   L   L   D   Y   L   P   Q   D   G   L

226  att ttt att gat gaa tcc cat att atg atc agc caa att aag ggc
      I   F   I   D   E   S   H   I   M   I   S   Q   I   K   G

271  atg tat gaa ggt gat cga agc cga aaa caa acc ttg gtt gac tat
      M   Y   E   G   D   R   S   R   K   Q   T   L   V   D   Y

316  ggt tat cga cta cct tca gct ctt gat aat cgg ccc tta aaa ctc
      G   Y   R   L   P   S   A   L   D   N   R   P   L   K   L

361  agt gaa ttt gag aaa tat caa cag gca aaa att tat gtt tca gcc
      S   E   F   E   K   Y   Q   Q   A   K   I   Y   V   S   A

406  aca ccg gcc agc tat gaa att gat aaa aca aat ggc gaa att gtc
      T   P   A   S   Y   E   I   D   K   T   N   G   E   I   V

451  tcg caa att atc aga cca act gga cta att gat cca gaa ata gta
      S   Q   I   I   R   P   T   G   L   I   D   P   E   I   V

496  att gaa tct acc aaa aat caa atg gag aaa att ttt cag tat ttg
      I   E   S   T   K   N   Q   M   E   K   I   F   Q   Y   L

541  cta aaa cag aag gaa aaa aaa gaa aga agt ctc att tta act acc
      L   K   Q   K   E   K   K   E   R   S   L   I   L   T   T

586  aca aaa cga ctg gcc gaa gaa atc agc aag tat ctc cag gaa gaa
      T   K   R   L   A   E   E   I   S   K   Y   L   Q   E   E

631  aaa tta caa aat gtc tat tat ttg cac tca gaa atg acg act ttt
      K   L   Q   N   V   Y   Y   L   H   S   E   M   T   T   F

676  gag cgc gat gaa atc ata att aag ctt cga aaa gga att tat gat
      E   R   D   E   I   I   I   K   L   R   K   G   I   Y   D
```

```
721  gca att gtc ggg ata aat tta ctt cgt gaa ggc gtt gat atc ccg
      A   I   V   G   I   N   L   L   R   E   G   V   D   I   P

766  gaa gtt tct ttg att ttt gtt ctt gaa gcc ggt ctt gtt tct ttt
      E   V   S   L   I   F   V   L   E   A   G   L   V   S   F

811  ttg cga tcc gca tgc gag ctc ggt acc ccg ggt cga cct gca
      L   R   S   A   C   E   L   G   T   P   G   R   P   A
```

FIGURE 11

Sequence 11. Represented by clone pAD700.

```
  1  atg ccc aaa tta aac cga ctt aga gcc cga ttt gtc cag att caa
      M   P   K   L   N   R   L   R   A   R   F   V   Q   I   Q

 46  aac att gaa aaa atg aca aat gta atg gaa atg att gcg aat gca
      N   I   E   K   M   T   N   V   M   E   M   I   A   N   A

 91  aaa att cca aaa ata aaa aac aag ttt aaa att gtt caa gaa tat
      K   I   P   K   I   K   N   K   F   K   I   V   Q   E   Y

136  ttt gaa aat tta gat tat att ttt caa aat att ctt gca aat tta
      F   E   N   L   D   Y   I   F   Q   N   I   L   A   N   L

181  tct aag aag gtt gag gaa tta act aat gct gat tcc aaa aaa aat
      S   K   K   V   E   E   L   T   N   A   D   S   K   K   N

226  ctt tat att att ttt gga tca aat tta ggt ttt tgt ggt gcc ctt
      L   Y   I   I   F   G   S   N   L   G   F   C   G   A   L

271  aat aat tta atc tta aaa aat gtt gtc cca caa ctt cag aaa aat
      N   N   L   I   L   K   N   V   V   P   Q   L   Q   K   N

316  gat gaa att atc gtc ttt ggt gaa aaa att tat aat ttt ttg tca
      D   E   I   I   V   F   G   E   K   I   Y   N   F   L   S

361  ata aat tac tct aat tta att att aaa ttt ttt cta aat att gaa
      I   N   Y   S   N   L   I   I   K   F   F   L   N   I   E

406  gaa act aat ttt agt gaa cca att tta gaa atc tca aac ttt gta
      E   T   N   F   S   E   P   I   L   E   I   S   N   F   V

451  aat caa tcg att ttt gag aga aaa tat aaa aaa att ttt att tgt
      N   Q   S   I   F   E   R   K   Y   K   K   I   F   I   C

496  tat aac aaa ttt atc agt att ata cat tca agc cca gag atg caa
      Y   N   K   F   I   S   I   I   H   S   S   P   E   M   Q

541  aat tta ttt gat ttc aaa aaa aat act ata aaa tac ggt ggt tac
      N   L   F   D   F   K   K   N   T   I   K   Y   G   G   Y

586  ggg att gag ttt gaa cca aat gct act gag gtt ttt aaa aaa tta
      G   I   E   F   E   P   N   A   T   E   V   F   K   K   L

631  atg ccc ttt tat ata aaa tcc atc ctt gaa aaa ctt ttt atc gaa
      M   P   F   Y   I   K   S   I   L   E   K   L   F   I   E

676  tcc aaa tta gtt gag act tca act aga cga aca tca atg gaa agt
      S   K   L   V   E   T   S   T   R   R   T   S   M   E   S
```

```
721  gca ctg aaa atg cca gtt gaa att ttg cat aag ttt aga aac aga
      A   L   K   M   P   V   E   I   L   H   K   F   R   N   R

766  aat aat tcc agt cgt cca gcc atg att acc cca gaa att att gag
      N   N   S   S   R   P   A   M   I   T   P   E   I   I   E

811  att att agt ggt aaa atg ttg aaa aag tta ggt
      I   I   S   G   K   M   L   K   K   L   G
```

FIGURE 12

Sequence 12. Represented by clone pAD711.

```
  1  tca ggt atg tca aaa aat att aag gaa att tca atc cta ccc ctt
      S   G   M   S   K   N   I   K   E   I   S   I   L   P   L

 46  aaa tta aat cct gct gga att atg cct gta att ttt gcc tta att
      K   L   N   P   A   G   I   M   P   V   I   F   A   L   I

 91  atc gtt tca ctg ccg aca ctt ttt agc gga ttt ctt gat aga aat
      I   V   S   L   P   T   L   F   S   G   F   L   D   R   N

136  acc tca gca gtt cgg aat tga ata gat aat aat atg caa att tat
      T   S   A   V   R   N   W   I   D   N   N   M   Q   I   Y

181  cac cca atc ggt ctt atc att ttt att gtt ttt aat gtc tcc ttt
      H   P   I   G   L   I   I   F   I   V   F   N   V   S   F

226  tca ata ata atg tcc tta caa caa tcc cga gtt gat aaa att gca
      S   I   I   M   S   L   Q   Q   S   R   V   D   K   I   A

271  cag gat ttt gcc aaa aat tca act ttt atc cct ggg att cgc cca
      Q   D   F   A   K   N   S   T   F   I   P   G   I   R   P

316  gga gaa cag act gaa gat tat tta att tca gtg gtt ttg cga ctt
      G   E   Q   T   E   D   Y   L   I   S   V   V   L   R   L

361  tca gtt ttc agt gcg att tat ctt acc ttt tta gga att ctc caa
      S   V   F   S   A   I   Y   L   T   F   L   G   I   L   Q

406  cct gtt gaa att atg tta ggt ctt cct tcg gca atc aca att tca
      P   V   E   I   M   L   G   L   P   S   A   I   T   I   S

451  gga act tcg ata ata att tta gca aca act aca ctt gaa acg att
      G   T   S   I   I   I   L   A   T   T   T   L   E   T   I

496  tcg cag atc aaa gcc cgt tat gat gca caa aaa gtt cta aaa caa
      S   Q   I   K   A   R   Y   D   A   Q   K   V   L   K   Q

541  agt aaa aag atc cgc aaa aat tta caa gtt cga aaa aat tct cct
      S   K   K   I   R   K   N   L   Q   V   R   K   N   S   P

586  tct att gat tca aat cag gat ctt tta tgg
      S   I   D   S   N   Q   D   L   L   W
```

FIGURE 13

Sequence 13. Represented by clone pAD721.

```
1    atc gcc gaa gaa gtt tca agt ttt tct ccg ttt gac cga ctt tta
      I   A   E   E   V   S   S   F   S   P   F   D   R   L   L

46   ttt ttt agg atg tta gat act gca act gca ggt gat att ttc acc
      F   F   R   M   L   D   T   A   T   A   G   D   I   F   T

91   tac ttt tca cca gaa att cag acc aaa tta gta cta agt tta cca
      Y   F   S   P   E   I   Q   T   K   L   V   L   S   L   P

136  aat gag cta atc aat aaa tta ctt gat gaa ctt tat gtt gat gaa
      N   E   L   I   N   K   L   L   D   E   L   Y   V   D   E

181  att gtc gaa ctt ctt gat gaa gtc cct gat aat gtt gcc aaa aga
      I   V   E   L   L   D   E   V   P   D   N   V   A   K   R

226  att ttg cgc aac att gac att gat act cgt aaa caa ata aat caa
      I   L   R   N   I   D   I   D   T   R   K   Q   I   N   Q

271  ctt ttg cag tat acc gac gat caa att ggc gct ttt atg tca gtt
      L   L   Q   Y   T   D   D   Q   I   G   A   F   M   S   V

316  gat atc gtc tat ctt ttt aaa gat tcg act tgt cat caa gca ctt
      D   I   V   Y   L   F   K   D   S   T   C   H   Q   A   L

361  gaa aaa att aga aac tat aaa gat atc tcc gaa tta gtg cat tat
      E   K   I   R   N   Y   K   D   I   S   E   L   V   H   Y

406  tat tat gtc gtt gat caa aac aag aaa ata atc ggg gca act act
      Y   Y   V   V   D   Q   N   K   K   I   I   G   A   T   T

451  tta gaa gat att gtc ttt tct gat cct aat act cag atc aaa gaa
      L   E   D   I   V   F   S   D   P   N   T   Q   I   K   E

496  att gtt ttt caa gtc cct ttt ctt gtt aca ctg ata aaa aag att
      I   V   F   Q   V   P   F   L   V   T   L   I   K   K   I

541  atg ccg ccg aag ttt ttg ccc aaa atg att ttt cca gta ctc ccg
      M   P   P   K   F   L   P   K   M   I   F   P   V   L   P

586  gtt gtt aat acc agc cag aaa cta atc cga atg gtt cca gtt gat
      V   V   N   T   S   Q   K   L   I   R   M   V   P   V   D

631  gat att atc cga tat tgt
      D   I   I   R   Y   C
```

FIGURE 14

Sequence 14. Represented by clone pAD727.

```
  1  tca ttt ggt tca gga ttt aat tta gca att gat ttt agt ggc gga
      S   F   G   S   G   F   N   L   A   I   D   F   S   G   G

 46  act aac ttt tta att gaa agc tca aat tca agt tat gat tta att
      T   N   F   L   I   E   S   S   N   S   S   Y   D   L   I

 91  aca aag gaa aaa gcc gaa aaa ata att agt ttt ctt gat tca caa
      T   K   E   K   A   E   K   I   I   S   F   L   D   S   Q

136  aat ata aac aag tca aat tca aca att ttg ctt aat cca tta aat
      N   I   N   K   S   N   S   T   I   L   L   N   P   L   N

181  gaa aat gga aat att ttt aat ctt gaa att aaa aca aaa ctt gat
      E   N   G   N   I   F   N   L   E   I   K   T   K   L   D

226  cta gca aca aaa att gcc tca tta aat acg gca atc cag aat aat
      L   A   T   K   I   A   S   L   N   T   A   I   Q   N   N

271  ttt tct aat att cga atg aca aat tat tca att tcg aat gaa gaa
      F   S   N   I   R   M   T   N   Y   S   I   S   N   E   E

316  gct caa aaa tta att ttc aat gca att ctt tca gtt gga atc gca
      A   Q   K   L   I   F   N   A   I   L   S   V   G   I   A

361  ctt att ttt gta act att ttt acg cta att agg ttt aaa tgg act
      L   I   F   V   T   I   F   T   L   I   R   F   K   W   T

406  ttt tcg ctt gca ata att ttc tca ctt ctt ttt aat gtt tta atg
      F   S   L   A   I   I   F   S   L   L   F   N   V   L   M

451  gtt ttg cta gca att att att aca cgg atc gaa ata tcg cag aat
      V   L   L   A   I   I   I   T   R   I   E   I   S   Q   N

496  tta gtt gtt gca att ctt act tta att ggt tat aca gta aat gat
      L   V   V   A   I   L   T   L   I   G   Y   T   V   N   D

541  aca atc gtg gtt ttt gat aga gta aaa gca aga ttt tca gaa ata
      T   I   V   V   F   D   R   V   K   A   R   F   S   E   I

586  aat cat gaa aat gtt tat aaa ttt gat aaa att aaa gaa att tcc
      N   H   E   N   V   Y   K   F   D   K   I   K   E   I   S

631  tta caa gca att aga gaa aca gca aaa agg tcg gta tat aca tcc
      L   Q   A   I   R   E   T   A   K   R   S   V   Y   T   S

676  ttg aca acc att tta aca att gtt gtt tta atg att ttt tat gaa
      L   T   T   I   L   T   I   V   V   L   M   I   F   Y   E

721  tca att gat att gtc ttt agc ctg acg atg tta att ggt gtg ata
```

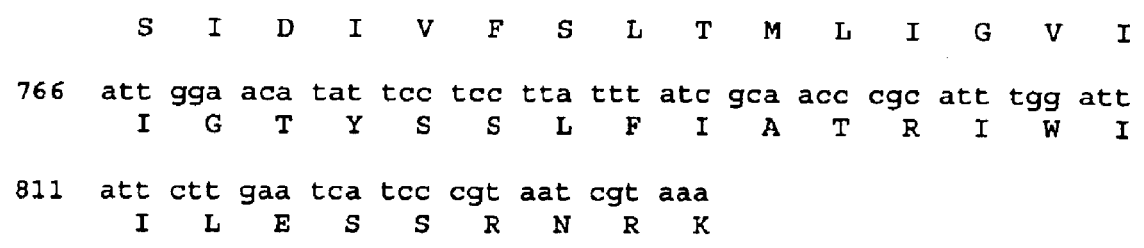

```
         S   I   D   I   V   F   S   L   T   M   L   I   G   V   I

766     att gga aca tat tcc tcc tta ttt atc gca acc cgc att tgg att
         I   G   T   Y   S   S   L   F   I   A   T   R   I   W   I

811     att ctt gaa tca tcc cgt aat cgt aaa
         I   L   E   S   S   R   N   R   K
```

FIGURE 15

Sequence 15. Represented by clone pAD742.

```
  1  atc gca att gaa aaa att gaa atc agg aca aaa gag ctt gaa aaa
      I   A   I   E   K   I   E   I   R   T   K   E   L   E   K

 46  caa gta aaa cag ctt gaa aaa caa gca gaa aat gca aaa att tac
      Q   V   K   Q   L   E   K   Q   A   E   N   A   K   I   Y

 91  ctc gaa aaa tca aag caa tta gaa tct gtt gaa gtc ggc tta att
      L   E   K   S   K   Q   L   E   S   V   E   V   G   L   I

136  gtc tct gat att aaa aag tac caa aca gaa tta gat caa gtc cag
      V   S   D   I   K   K   Y   Q   T   E   L   D   Q   V   Q

181  gaa aaa tta aat gat cta aaa ttt caa gaa cct aaa ttt atc agc
      E   K   L   N   D   L   K   F   Q   E   P   K   F   I   S

226  gaa att gaa gca aat gag aaa ata att att aca aat aca caa aaa
      E   I   E   A   N   E   K   I   I   I   T   N   T   Q   K

271  agg tca gaa att gaa gct gaa atc aac act aaa aac cgc gaa att
      R   S   E   I   E   A   E   I   N   T   K   N   R   E   I

316  cac cgc cta aaa gag caa att aat acc cta aat tta gct tat gca
      H   R   L   K   E   Q   I   N   T   L   N   L   A   Y   A

361  aaa gca act caa ctt caa gaa atg att tta tca agt gaa att agt
      K   A   T   Q   L   Q   E   M   I   L   S   S   E   I   S

406  gta aat ttt gag caa aaa atg gct gct ttg cgc caa aaa tat agt
      V   N   F   E   Q   K   M   A   A   L   R   Q   K   Y   S

451  ctt ata agc gcg caa aaa gac aat ttt gca aaa tta atc agc caa
      L   I   S   A   Q   K   D   N   F   A   K   L   I   S   Q

496  aac aag ctc aaa aaa cta gaa att gaa gaa aaa ctt aat aca ttt
      N   K   L   K   K   L   E   I   E   E   K   L   N   T   F

541  agg aca caa aag ggt gaa att gaa agg aat tta tac agt cta aat
      R   T   Q   K   G   E   I   E   R   N   L   Y   S   L   N

586  tcc gaa aaa att att agt caa act aga atc tcc gag cta aaa aag
      S   E   K   I   I   S   Q   T   R   I   S   E   L   K   K

631  tcc tta gaa tca atg tct ttt ttg cca aag ggg aca aaa atc att
      S   L   E   S   M   S   F   L   P   K   G   T   K   I   I

676  atc gaa aat agc ttt ctt ttt cct gga tat tgt ggg ctt gtc tct
      I   E   N   S   F   L   F   P   G   Y   C   G   L   V   S
```

```
721   gat tta atc aaa att ttc cca aaa tat aca ggc gca att gaa gcc
       D   L   I   K   I   F   P   K   Y   T   G   A   I   E   A

766   gca ttg ggt cca act tta aaa caa att gtt gtt gac caa cct gaa
       A   L   G   P   T   L   K   Q   I   V   V   D   Q   P   E

811   acc gca gtt tca gca att aat ttt cta aag aaa aat tat gca gga
       T   A   V   S   A   I   N   F   L   K   K   N   Y   A   G

856   agc gca aca ttt atc ccc ctt tca aca tta aaa ccg cga ttt att
       S   A   T   F   I   P   L   S   T   L   K   P   R   F   I

901   ccc gat tta tat ctt gaa cat cta aat tca caa aaa ggt ttt ata
       P   D   L   Y   L   E   H   L   N   S   Q   K   G   F   I

946   aat tta gct agc aat tta gtc gat ttt gaa aaa aaa tac aag att
       N   L   A   S   N   L   V   D   F   E   K   K   Y   K   I

991   tta gcg gat ttt tta cta gga ggg att att gtt gct gat aca att
       L   A   D   F   L   L   G   G   I   I   V   A   D   T   I

1036  gat tca gca aat cga atc gca aac ttc ctt aac cac aaa aac atg
       D   S   A   N   R   I   A   N   F   L   N   H   K   N   M

1081  atc gta act tta gac ggc gat gtt att aga act agc ggg ata att
       I   V   T   L   D   G   D   V   I   R   T   S   G   I   I

1126  tct ggg ggt cat aag ata aaa aat gat tct tcc ttt tca att cag
       S   G   G   H   K   I   K   N   D   S   S   F   S   I   Q

1171  tat aaa atc gat gaa cta aca aat aat ttg aat ttt ttt gaa gaa
       Y   K   I   D   E   L   T   N   N   L   N   F   F   E   E

1216  aaa att caa gaa ttt aaa gtt aaa tct aat gaa ttt gaa cag tta
       K   I   Q   E   F   K   V   K   S   N   E   F   E   Q   L

1261  att aca aga gaa tct gta ttt tta cag caa att aat att aat ctt
       I   T   R   E   S   V   F   L   Q   Q   I   N   I   N   L

1306  aat gat tta gag caa aaa ttt agt aat tct gaa aat gaa tta atc
       N   D   L   E   Q   K   F   S   N   S   E   N   E   L   I

1351  gaa att aaa gct caa aat gaa ggt ctt gaa gag agt cta aat caa
       E   I   K   A   Q   N   E   G   L   E   E   S   L   N   Q

1396  aaa gat gac cta aat tta agt cta aat cga act tta aaa gaa aaa
       K   D   D   L   N   L   S   L   N   R   T   L   K   E   K

1441  att gaa ctt gaa aat gtg gtt tta gaa ctt gaa aat caa tgc aaa
       I   E   L   E   N   V   V   L   E   L   E   N   Q   C   K
```

```
1486  att tta aaa act gaa aaa aaa cag ctc gat aat caa att tca gaa
       I   L   K   T   E   K   K   Q   L   D   N   Q   I   S   E

1531  ctt aca gtt tta gtt caa gaa ctt aac caa aaa cag cga aaa atc
       L   T   V   L   V   Q   E   L   N   Q   K   Q   R   K   I

1576  aac gca gat ctt aac caa aat caa aat tac aaa gac aaa tat gaa
       N   A   D   L   N   Q   N   Q   N   Y   K   D   K   Y   E

1621  ttt tta att aca aat tta cga aat aat tta tcc caa aaa tac agt
       F   L   I   T   N   L   R   N   N   L   S   Q   K   Y   S

1666  cta act ttt gaa ggc gca gct caa aaa tat gaa ctt gaa att cca
       L   T   F   E   G   A   A   Q   K   Y   E   L   E   I   P

1711  gaa aaa gat gct cgc gaa ttt gtt aat agt cta aat tta gag att
       E   K   D   A   R   E   F   V   N   S   L   N   L   E   I

1756  aaa gcg ctt gga aat gtt aat tta gat gca att aat gac ttt gaa
       K   A   L   G   N   V   N   L   D   A   I   N   D   F   E

1801  aca acg agt caa aga ctc gaa aaa cta aaa aaa agt caa aat gaa
       T   T   S   Q   R   L   E   K   L   K   K   S   Q   N   E

1846  ctt gaa act gcc agg tca aaa att tta gaa gtt atc tcg gat tta
       L   E   T   A   R   S   K   I   L   E   V   I   S   D   L

1891  gat aaa att atc att gga aaa acc cag gaa att gtc gat cta gtt
       D   K   I   I   I   G   K   T   Q   E   I   V   D   L   V

1936  aat tcc gag ttt aac ctt gtt ttc cag aat atg ttt ggt ggg gga
       N   S   E   F   N   L   V   F   Q   N   M   F   G   G   G

1981  agt gca aaa att tat ttt agt gat aaa aac gat att tta aat tcg
       S   A   K   I   Y   F   S   D   K   N   D   I   L   N   S

2026  ggg att gaa ata agt gcc caa cca cct gga aaa act atc aaa aat
       G   I   E   I   S   A   Q   P   P   G   K   T   I   K   N

2071  att agg ctt ttt tct ggg ggc gaa aag gca att att gca att tca
       I   R   L   F   S   G   G   E   K   A   I   I   A   I   S

2116  ctt ttg ttt tca att att aag gca aga cca att ccg ctt tgc att
       L   L   F   S   I   I   K   A   R   P   I   P   L   C   I

2161  ctt gat gaa gtt gaa gct gcc ctt gat gag tca aat gtg atc aga
       L   D   E   V   E   A   A   L   D   E   S   N   V   I   R

2206  tat gtg gaa ttt cga aag cag tta aaa caa aaa acg cag ttt ttg
       Y   V   E   F   R   K   Q   L   K   Q   K   T   Q   F   L

2251  atc atc acc cat cgg cac gga acg atg tcc cga gtt gat caa ctt
```

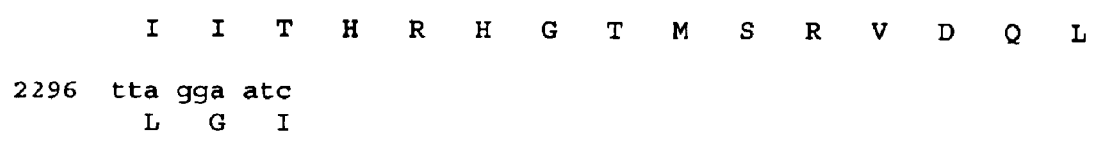

```
      I   I   T   H   R   H   G   T   M   S   R   V   D   Q   L

2296 tta gga atc
      L   G   I
```

FIGURE 16

Sequence 16. Represented by clone pAD760.

```
1    atg aat aga aaa aaa acc gaa aaa tca aaa att agt tca aaa gat
      M   N   R   K   K   T   E   K   S   K   I   S   S   K   D

46   agt aaa aaa tta ata att caa gct atc caa gat gtg gca aaa aat
      S   K   K   L   I   I   Q   A   I   Q   D   V   A   K   N

91   agc gaa tta aat ctg gaa gca gtt att gat att ttt cag gaa gca
      S   E   L   N   L   E   A   V   I   D   I   F   Q   E   A

136  att gaa ttt gta ata aca aag aaa att gac cca gat gcg caa ata
      I   E   F   V   I   T   K   K   I   D   P   D   A   Q   I

181  aaa att gaa gct gat ctt gaa caa ttg agt ttt aaa gtt ttt aat
      K   I   E   A   D   L   E   Q   L   S   F   K   V   F   N

226  aca aac ggg att gtt gtt gaa gaa aat tat ttt gat gat ctt aca
      T   N   G   I   V   V   E   E   N   Y   F   D   D   L   T

271  gat gag gaa aaa gtt aac gat ctt gtt tct ttt att tta cta tca
      D   E   E   K   V   N   D   L   V   S   F   I   L   L   S

316  aag gca aaa gaa act gat cct gag att cag gtt gat gat att ttt
      K   A   K   E   T   D   P   E   I   Q   V   D   D   I   F

361  tca att gaa att aat ctt gaa agt ttt gaa cat tga ctt ttt atg
      S   I   E   I   N   L   E   S   F   E   H   W   L   F   M

406  gca att atg cac gct ttt aag caa aaa att tct gaa att gtc cga
      A   I   M   H   A   F   K   Q   K   I   S   E   I   V   R

451  aat aat gtt tat aac aaa tat tta tcg ctt aaa aat aac gta gtt
      N   N   V   Y   N   K   Y   L   S   L   K   N   N   V   V

496  ttg gcc act gtt act aat aaa att gct gct ggt tat att ttc gaa
      L   A   T   V   T   N   K   I   A   A   G   Y   I   F   E

541  att gac gat gat aaa gtt tct gcc ttt atg cca agc cat tat gca
      I   D   D   D   K   V   S   A   F   M   P   S   H   Y   A

586  agt gga caa aat tta aaa ata ggc act aaa cat gaa gtt gta att
      S   G   Q   N   L   K   I   G   T   K   H   E   V   V   I

631  gaa aat gta tca aaa aat aca aaa cag tcg cag gtt gtg ata tcc
      E   N   V   S   K   N   T   K   Q   S   Q   V   V   I   S

676  tca aaa tca gtt caa ctt gtc aag aaa aaa ata atc gat gca atc
      S   K   S   V   Q   L   V   K   K   K   I   I   D   A   I
```

```
721   cct gaa cta cag tca aaa ttt ctt gaa atc act tca att gca cgg
       P   E   L   Q   S   K   F   L   E   I   T   S   I   A   R

766   att cca ggg gaa aga tgt aaa gtc gca att cgc aga aat gaa gat
       I   P   G   E   R   C   K   V   A   I   R   R   N   E   D

811   gcc gaa gct gat aat att tct gaa atc ggc tca att gta gga gca
       A   E   A   D   N   I   S   E   I   G   S   I   V   G   A

856   act ggc tca aga gtt ctt gca att tct caa gaa ctt caa ggt gaa
       T   G   S   R   V   L   A   I   S   Q   E   L   Q   G   E

901   aaa att gag gtg att aaa tat gat gat aat att gtc aaa ttt att
       K   I   E   V   I   K   Y   D   D   N   I   V   K   F   I

946   gtt aat gcg atg tcg cct tca aaa gtt att tgc gta aaa gag ttc
       V   N   A   M   S   P   S   K   V   I   C   V   K   E   F

991   aaa ata ggt cat aaa tta cgt cgt ttt atc gta gtt gtt cct gat
       K   I   G   H   K   L   R   R   F   I   V   V   V   P   D

1036  ttt caa cat agt tta gcc att gga aaa aac ggt tca aat gtt aaa
       F   Q   H   S   L   A   I   G   K   N   G   S   N   V   K

1081  cta gta gca gat cta aca cgt tgt caa gtg caa att atc ccg tat
       L   V   A   D   L   T   R   C   Q   V   Q   I   I   P   Y

1126  tca agc gcg cta aaa gat caa aat ttt aaa att gaa tga aat gga
       S   S   A   L   K   D   Q   N   F   K   I   E   W   N   G

1171  aat att aaa gac att caa gaa cta aac agt ctt aac aat gag tat
       N   I   K   D   I   Q   E   L   N   S   L   N   N   E   Y

1216  att cat cgc cag cag ggt aga att tat caa aat cat cgg aat tca
       I   H   R   Q   Q   G   R   I   Y   Q   N   H   R   N   S

1261  tat ggt caa ggt aat aat aat ttt gac tta att tta cag caa ttc
       Y   G   Q   G   N   N   N   F   D   L   I   L   Q   Q   F

1306  gaa tct gat att cgc gag tta gaa aaa cct tat ggg att gaa aac
       E   S   D   I   R   E   L   E   K   P   Y   G   I   E   N

1351  gag ttt ata cca aaa aat gag caa aaa cag gta aga agt cac caa
       E   F   I   P   K   N   E   Q   K   Q   V   R   S   H   Q

1396  gaa ttt cca aaa aac aag aat aat cta gca aaa gca gca act aaa
       E   F   P   K   N   K   N   N   L   A   K   A   A   T   K

1441  tcg cgt aat ttt aac aaa agc cag aat atc cgc gaa aat att tca
       S   R   N   F   N   K   S   Q   N   I   R   E   N   I   S
```

```
1486  aaa gat ttt gat tat ggc ttt gaa aac gag aaa gat tct aat tct
       K   D   F   D   Y   G   F   E   N   E   K   D   S   N   S

1531  ttc caa aat att agt caa aga tct ttt ttt gat gca gat tca ctt
       F   Q   N   I   S   Q   R   S   F   F   D   A   D   S   L

1576  ttt gat tcg gct cta aat gag gca att agt gaa aac gag tta atc
       F   D   S   A   L   N   E   A   I   S   E   N   E   L   I

1621  gat aaa att cac caa gaa gag gaa aaa aaa caa gaa tta tta tta
       D   K   I   H   Q   E   E   E   K   K   Q   E   L   L   L

1666  caa gag aag gaa aaa tga gca aaa aat gaa gct
       Q   E   K   E   K   W   A   K   N   E   A
```

FIGURE 17

Sequence 17. Represented by clone pAD774.

```
  1  gaa ttc tac ctt tga tca cct aat gca aat cgg gta cat ttt gca
      E   F   Y   L   W   S   P   N   A   N   R   V   H   F   A

 46  att tat aaa gat ccg gaa gac aaa att ccg gct gaa att att gtg
      I   Y   K   D   P   E   D   K   I   P   A   E   I   I   V

 91  atg tca aaa aat aat gat gtt tgg ttt tgc caa att aat gcc tct
      M   S   K   N   N   D   V   W   F   C   Q   I   N   A   S

136  ttt aat gga tat tcc tat aat tta tta att gag cat cac gat tta
      F   N   G   Y   S   Y   N   L   L   I   E   H   H   D   L

181  aaa ata act gag gca ctt gat cct tat gcc ttt agt att gcg cct
      K   I   T   E   A   L   D   P   Y   A   F   S   I   A   P

226  ttt gat tga aaa aaa aat gaa agt cca aaa gca tat tta att gac
      F   D   W   K   K   N   E   S   P   K   A   Y   L   I   D

271  att ttt tcc gaa aaa act gga aaa aat cct tca aaa tta gaa gga
      I   F   S   E   K   T   G   K   N   P   S   K   L   E   G

316  ttt aac aaa aat ccg caa att gat gct caa att tat cag ctg cac
      F   N   K   N   P   Q   I   D   A   Q   I   Y   Q   L   H

361  att cga gat ttt tca tct att agt aaa aaa aca gaa aat aaa ggt
      I   R   D   F   S   S   I   S   K   K   T   E   N   K   G

406  act ttt atc gga gcg cta gaa aat gat gtt ttt agt tat tta aat
      T   F   I   G   A   L   E   N   D   V   F   S   Y   L   N

451  agc tta aaa ttt aat ttt tta caa tta tta cca atc cac tct tgt
      S   L   K   F   N   F   L   Q   L   L   P   I   H   S   C

496  tat aat ttc agc caa aaa aac gct agc atc ctc cac aaa ggg gat
      Y   N   F   S   Q   K   N   A   S   I   L   H   K   G   D

541  gga aac ggt cat ttt agc act tat aat tgg ggt tat gac cca att
      G   N   G   H   F   S   T   Y   N   W   G   Y   D   P   I

586  ggt tac ttt tcg ata aat tca agt tat tca aca gat cca atg gat
      G   Y   F   S   I   N   S   S   Y   S   T   D   P   M   D

631  cca tat ctg cga att ttt gag ttt aaa aaa ttt gtt gac tcc gcc
      P   Y   L   R   I   F   E   F   K   K   F   V   D   S   A

676  cat aaa aat aag atc gga att gtt ctt gat gtt gat ttt agt cac
```

```
      H   K   N   K   I   G   I   V   L   D   V   D   F   S   H

 721 acc ttt aaa aat tca att ctt gag gat gta gct cac ggg cat ttt
      T   F   K   N   S   I   L   E   D   V   A   H   G   H   F

 766 tac cgg gat gaa gca gct gtt tta cct gcc gga ttt ccg cca ctt
      Y   R   D   E   A   A   V   L   P   A   G   F   P   P   L

 811 gat aca cga aaa cca atg gca ttt agg cta att ttg gat tcc tta
      D   T   R   K   P   M   A   F   R   L   I   L   D   S   L

 856 att ttt ttt act aaa tat tat aaa gtt gat gga ttt cgc ttt aat
      I   F   F   T   K   Y   Y   K   V   D   G   F   R   F   N

 901 tta gca tct ttt tta gat aaa aaa gca att aca gtt att gcc agt
      L   A   S   F   L   D   K   K   A   I   T   V   I   A   S

 946 gaa cta aaa aaa gtt aat cca aat att ctt tta tat ggt gat ttt
      E   L   K   K   V   N   P   N   I   L   L   Y   G   D   F

 991 tca aat cct agt gac cta cca agc aga aat cga ctt gaa aaa ggg
      S   N   P   S   D   L   P   S   R   N   R   L   E   K   G

1036 aaa aca gga aat agt ttt aac ttt gga tat tta aac gat aca atc
      K   T   G   N   S   F   N   F   G   Y   L   N   D   T   I

1081 caa aca gca att atc ggg agc gga aat ccg cgt gat aaa ggt tta
      Q   T   A   I   I   G   S   G   N   P   R   D   K   G   L

1126 att tta tca aaa act agt aaa aaa ttc gct gct tat gtt tct tca
      I   L   S   K   T   S   K   K   F   A   A   Y   V   S   S

1171 att ccg ggg aac att gca aat ttt gac ttc caa aat ttg cca tat
      I   P   G   N   I   A   N   F   D   F   Q   N   L   P   Y

1216 tca aaa aaa aaa tac gac ctt ttt gca aac gat atc agc cta aat
      S   K   K   K   Y   D   L   F   A   N   D   I   S   L   N

1261 ctt gcc tat ctt act tgt tat aat ggc ccg act tta gcc gat aaa
      L   A   Y   L   T   C   Y   N   G   P   T   L   A   D   K

1306 att ctt agt gcg aca acg cga att gga aaa aga gaa ttt ctt gaa
      I   L   S   A   T   T   R   I   G   K   R   E   F   L   E

1351 atc tac cgg caa gcc tta atg atg gtc aat ttt gtc caa gga aaa
      I   Y   R   Q   A   L   M   M   V   N   F   V   Q   G   K

1396 att tca ctt agt gct ggg act gaa ttt gct ttt tca aga att tgt
      I   S   L   S   A   G   T   E   F   A   F   S   R   I   C

1441 gat ttt tct ggg ggc agt tat caa aat tgc tat cct aat tta aac
      D   F   S   G   G   S   Y   Q   N   C   Y   P   N   L   N
```

```
1486  ata aaa aga ccg cct ttt tcg ttt tta gcg ggc aaa tat ctt gat
       I   K   R   P   P   F   S   F   L   A   G   K   Y   L   D

1531  ttt cat tct gat aaa acc aca gat ttc aca aat gga ttg aat ttt
       F   H   S   D   K   T   T   D   F   T   N   G   L   N   F

1576  gaa att ctt aaa aac aat gaa atc aaa gag aaa atc ttt gat ttt
       E   I   L   K   N   N   E   I   K   E   K   I   F   D   F

1621  ctt gcc gaa att aat caa ttt cgc caa aat tct cca ttt ttt cgg
       L   A   E   I   N   Q   F   R   Q   N   S   P   F   F   R

1666  ctt gat aca aac caa aaa atc aaa aaa cag cta aaa ttt gaa act
       L   D   T   N   Q   K   I   K   K   Q   L   K   F   E   T

1711  gtt gat aac aat aaa gga tta att atc ttt aaa att ctg cta aaa
       V   D   N   N   K   G   L   I   I   F   K   I   L   L   K

1756  ata aag tga tta aag tta ttc ata att ttt cac atc ttt ctt atg
       I   K   W   L   K   L   F   I   I   F   H   I   F   L   M

1801  aat atg att tta aaa att tta ata ttc ttt tta gct caa aga tta
       N   M   I   L   K   I   L   I   F   F   L   A   Q   R   L

1846  aag tta ttc cta att
       K   L   F   L   I
```

FIGURE 18

Sequence 18. Represented by clone pAD784.

```
  1 gct ttt ttg ttt gtt gat ggt cgg tat att gaa aaa gct gaa aaa
     A   F   L   F   V   D   G   R   Y   I   E   K   A   E   K

 46 gat gct aaa aat tgt cag gtt ttt tta cct acc aag caa atc ttg
     D   A   K   N   C   Q   V   F   L   P   T   K   Q   I   L

 91 aag att ttt tca aga aaa ccc gta tca aaa aat cgg cat tga tct
     K   I   F   S   R   K   P   V   S   K   N   R   H   W   S

136 gaa tat tta act att gac caa ttt gat aaa ata aga agt tga ttt
     E   Y   L   T   I   D   Q   F   D   K   I   R   S   W   F

181 cca aat gcc gat ttt gtt aag tta caa gcc caa ctt ttt cga att
     P   N   A   D   F   V   K   L   Q   A   Q   L   F   R   I

226 ata aaa aca gaa gaa gaa atc aaa aat atc gaa aaa gct gtt gaa
     I   K   T   E   E   E   I   K   N   I   E   K   A   V   E

271 atc tca ctc gcg gct tat aat aaa ata ttt cca aaa atc aaa ccg
     I   S   L   A   A   Y   N   K   I   F   P   K   I   K   P

316 gga atg acg gag aaa agt atc gat gtc aac cta aat tat caa atg
     G   M   T   E   K   S   I   D   V   N   L   N   Y   Q   M

361 aag ctt tta gga gcc gaa aaa gaa tcc ttt gat tca ata att gca
     K   L   L   G   A   E   K   E   S   F   D   S   I   I   A

406 act ggt tct aat tcg gca atg ccg cat tga agg gcg agt gaa acc
     T   G   S   N   S   A   M   P   H   W   R   A   S   E   T

451 gaa att tta gat aat gat ctt tta aaa att gat ttt ggt gcg ctt
     E   I   L   D   N   D   L   L   K   I   D   F   G   A   L

496 ttt aac ggt tat tgc gct gat att aca aga act tct tat ctt gga
     F   N   G   Y   C   A   D   I   T   R   T   S   Y   L   G

541 cag att agt gaa aaa aaa tta gaa att ttg gaa ata gta aaa aaa
     Q   I   S   E   K   K   L   E   I   L   E   I   V   K   K

586 gct gct gaa att ggt aga aaa aaa gtt gct cct ggg gtt aaa gcc
     A   A   E   I   G   R   K   K   V   A   P   G   V   K   A

631 agc gaa att gac ctt gct tgc cgg aat ttt atc acc gaa caa ggc
     S   E   I   D   L   A   C   R   N   F   I   T   E   Q   G

676 tat gga aaa tat ttt att cac tca act ggc cac ggg gtt ggt att
     Y   G   K   Y   F   I   H   S   T   G   H   G   V   G   I
```

```
721  gat atc cat gaa ttg cca gtt gtt agt tca act agc cag aca att
      D   I   H   E   L   P   V   V   S   S   T   S   Q   T   I

766  tta gag ccc gga atg gta ata act gtt gaa ccc gga att tat atc
      L   E   P   G   M   V   I   T   V   E   P   G   I   Y   I

811  cct gga ctt gga ggc gca aga att gag gat gtt gtt tta gta act
      P   G   L   G   G   A   R   I   E   D   V   V   L   V   T

856  gaa agt ggt ttt cgt acc ttg tca cga aaa ggt gaa aga att
      E   S   G   F   R   T   L   S   R   K   G   E   R   I
```

FIGURE 19

Sequence 19. Represented by clone pAD789.

```
  1  gat ctt gta ttt aaa gta gaa aat tct gaa aat caa tta caa gat
      D   L   V   F   K   V   E   N   S   E   N   Q   L   Q   D

 46  tta gat gga act ttt tct tta att agt att aaa aat tta aac tat
      L   D   G   T   F   S   L   I   S   I   K   N   L   N   Y

 91  aaa ttg gaa gat aga gtt tta ttt aat aat tta aat tta gaa gtt
      K   L   E   D   R   V   L   F   N   N   L   N   L   E   V

136  caa aaa ggt aaa aaa tat tta cta aaa gga gct aac ggg tct gga
      Q   K   G   K   K   Y   L   L   K   G   A   N   G   S   G

181  aag tcc aca ttt tca agg att tta tta ggc att gag aag gaa ttt
      K   S   T   F   S   R   I   L   L   G   I   E   K   E   F

226  gaa ggt caa att tta ata aat aac aaa tac gat ata aaa aaa ata
      E   G   Q   I   L   I   N   N   K   Y   D   I   K   K   I

271  aat cct gat tct ata aat aac cat att aat tat gta tac aac aat
      N   P   D   S   I   N   N   H   I   N   Y   V   Y   N   N

316  tca gac tta att aat gca tca act cta gaa aat att tcg ctt ttg
      S   D   L   I   N   A   S   T   L   E   N   I   S   L   L

361  gaa ccg aaa aca aaa gat gag att agg ccg tta tta gaa aag gta
      E   P   K   T   K   D   E   I   R   P   L   L   E   K   V

406  aat ttt gaa aac ctt gat tta gac aag aaa att gat tct gat gtt
      N   F   E   N   L   D   L   D   K   K   I   D   S   D   V

451  tga tta ttt ttc cac tgg gca aat cca aaa aat ccc ctt gca cgc
      W   L   F   F   H   W   A   N   P   K   N   P   L   A   R

496  tca ctt tat tct cca aaa gaa att tta ata att gac gaa ggt ctt
      S   L   Y   S   P   K   E   I   L   I   I   D   E   G   L

541  tcc aac tta gac caa gaa agt tat gtt aaa atc ata tct gaa ctt
      S   N   L   D   Q   E   S   Y   V   K   I   I   S   E   L

586  att gcg gat aaa aat tta aca tta att ttc att acc cct cac ttt
      I   A   D   K   N   L   T   L   I   F   I   T   P   H   F

631  gat
      D
```

FIGURE 20

Sequence 20. Represented by clones pAD908, pAD981, pAD1013, and pAD1049.

```
  1  ctt gaa ata atc aaa tat gga tca aaa gaa tct cta aat tac tga
      L   E   I   I   K   Y   G   S   K   E   S   L   N   Y   W

 46  cta att tct gaa agc ggg aaa aga tat gac tat ttt cga cca att
      L   I   S   E   S   G   K   R   Y   D   Y   F   R   P   I

 91  gaa gga att ctt aat aaa att cag aga aaa ttt tgg gag aca tca
      E   G   I   L   N   K   I   Q   R   K   F   W   E   T   S

136  agc gaa gat tta cga ctt tga ttt aag aaa atg atg tca gaa ttt
      S   E   D   L   R   L   W   F   K   K   M   M   S   E   F

181  cct tgt agt agt tgc aaa gga gcc cgg ctt aac aag tat gcg ctt
      P   C   S   S   C   K   G   A   R   L   N   K   Y   A   L

226  gcc gtt ttc att gaa aag tat aat atc ttt caa tta tcc caa ctt
      A   V   F   I   E   K   Y   N   I   F   Q   L   S   Q   L

271  tca att aaa gat tta ata act ttt ttt aga aat tta aaa tta act
      S   I   K   D   L   I   T   F   F   R   N   L   K   L   T

316  gaa ttt gac gga aaa att tct act tta att ctc gat gaa att aaa
      E   F   D   G   K   I   S   T   L   I   L   D   E   I   K

361  tca cga ctg tca ttt tta gca aat gtt ggt ctt gaa tat tta act
      S   R   L   S   F   L   A   N   V   G   L   E   Y   L   T

406  tta aat aga tca acg gca acc tta tca gga ggc gaa tcc caa cga
      L   N   R   S   T   A   T   L   S   G   G   E   S   Q   R

451  att agg ctt gca agc cag gtt gga tat caa cta acc gga att ctt
      I   R   L   A   S   Q   V   G   Y   Q   L   T   G   I   L

496  tat gtt ctt gat gaa cct tca att ggc cta cat caa aaa gat aat
      Y   V   L   D   E   P   S   I   G   L   H   Q   K   D   N

541  gac aaa tta att gcg aca ctg aaa aaa atg gtt gaa att ggt aat
      D   K   L   I   A   T   L   K   K   M   V   E   I   G   N

586  agt tta att gta gtc gag cat gat ttt gag aca att tta gct gct
      S   L   I   V   V   E   H   D   F   E   T   I   L   A   A

631  gat tat att gtt gat atc ggg cca aaa gct ggt gaa aac ggt ggt
      D   Y   I   V   D   I   G   P   K   A   G   E   N   G   G
```

```
676   ttt ttg gtt gct gca gga tca att aag gat att gaa aat gaa cca
       F   L   V   A   A   G   S   I   K   D   I   E   N   E   P

721   aaa tca ctt acc ggc caa ttt tta act gga aaa ttg gaa att cca
       K   S   L   T   G   Q   F   L   T   G   K   L   E   I   P

766   gta cca aaa aaa cga cgg gct ggc aat ggc aaa ttt ata att att
       V   P   K   K   R   R   A   G   N   G   K   F   I   I   I

811   gaa aaa gct gct gaa aat aat tta aaa aaa att aat gtc aac att
       E   K   A   A   E   N   N   L   K   K   I   N   V   N   I

856   cct cta ggc aaa ttt gtt gtt gtc act ggt gtt tct gga tct gga
       P   L   G   K   F   V   V   V   T   G   V   S   G   S   G

901   aag tcg aca tta gtt aat caa att atc gta aat gcg att gcc aaa
       K   S   T   L   V   N   Q   I   I   V   N   A   I   A   K

946   aat ctt gga aca act aat att cgc att ggg aaa aat gtg agg aaa
       N   L   G   T   T   N   I   R   I   G   K   N   V   R   K

991   tta aag ggc ttt tta ata ttg ata agt tga ttg caa tca atc aaa
       L   K   G   F   L   I   L   I   S   W   L   Q   S   I   K

1036  gtc aat cgg acg aac cct aga tca aat ccc gca act tat acc tct
       V   N   R   T   N   P   R   S   N   P   A   T   Y   T   S

1081  gtt ttt gat gat atc cgt gag gtt ttt gcc aat act gag cag gca
       V   F   D   D   I   R   E   V   F   A   N   T   E   Q   A

1126  aga gcg ctt ggt ttt tca aag tca aaa ttt tcc ttt aat ctg caa
       R   A   L   G   F   S   K   S   K   F   S   F   N   L   Q

1171  act ggg cgg tgt gat aaa tgc caa gga gac ggg caa att aaa att
       T   G   R   C   D   K   C   Q   G   D   G   Q   I   K   I

1216  gaa atg tat ttt atg cct gat att tat gtt tta tgt gat cac tgc
       E   M   Y   F   M   P   D   I   Y   V   L   C   D   H   C

1261  caa gga aaa aga tac aag ccg gat gtc cta caa att cgt ttt tat
       Q   G   K   R   Y   K   P   D   V   L   Q   I   R   F   Y

1306  gga aaa aca atc gcg gat att ctt gat tta aca gtt tca gaa gca
       G   K   T   I   A   D   I   L   D   L   T   V   S   E   A

1351  ctt gaa ttt ttc cat aat tgg cct aaa ata atc gca aaa tta caa
       L   E   F   F   H   N   W   P   K   I   I   A   K   L   Q

1396  acc cta gct gat gtt ggt ctt ggt tat ata aaa ctt ggc caa tca
       T   L   A   D   V   G   L   G   Y   I   K   L   G   Q   S

1441  gca ata act tta tca gga gga gaa gct caa cga att aaa tta gcc
```

```
      A   I   T   L   S   G   G   E   A   Q   R   I   K   L   A

1486 act ttt tta caa aaa aaa cct aaa gga aaa tca ctt ttt gta ctt
      T   F   L   Q   K   K   P   K   G   K   S   L   F   V   L

1531 gac gag cca aca act gga ctc cat aat tat gat gtt gct aat tta
      D   E   P   T   T   G   L   H   N   Y   D   V   A   N   L

1576 att aaa gtg cta aat cga ata gtc gat aac ggt gat agc ata att
      I   K   V   L   N   R   I   V   D   N   G   D   S   I   I

1621 gta atc gag cat aat tta gag gta att aaa gtt gct gac tat att
      V   I   E   H   N   L   E   V   I   K   V   A   D   Y   I

1666 att gat tta ggc cca aac ggc ggg gat aac ggg ggc caa ata gtt
      I   D   L   G   P   N   G   G   D   N   G   G   Q   I   V

1711 gca aaa gga aca cca gaa gct gta gca aaa gtt agt gaa tca tat
      A   K   G   T   P   E   A   V   A   K   V   S   E   S   Y

1756 act ggc gct tat tta aaa aca att tta aat ata aaa
      T   G   A   Y   L   K   T   I   L   N   I   K
```

FIGURE 21

Sequence 21. Represented by clone pAD913.

```
  1  atg aaa att aaa gca aaa acc atc gta aaa att tat gat caa aaa
      M   K   I   K   A   K   T   I   V   K   I   Y   D   Q   K

 46  tta cca tca gaa tta aaa gcc ctt gat aaa gta act act gaa ata
      L   P   S   E   L   K   A   L   D   K   V   T   T   E   I

 91  aat cag ggc gag ttt att gca ata att ggc caa act ggt tca gga
      N   Q   G   E   F   I   A   I   I   G   Q   T   G   S   G

136  aaa aca act ttt att cag cat atg aat gca ctt ttg cta cca gat
      K   T   T   F   I   Q   H   M   N   A   L   L   L   P   D

181  caa ggc gaa att gag tat ctc tat ttt gat tca aaa aat caa gaa
      Q   G   E   I   E   Y   L   Y   F   D   S   K   N   Q   E

226  aaa aaa tta gtt gtt caa aaa ccg cgt ttt ttt aga aaa aaa cta
      K   K   L   V   V   Q   K   P   R   F   F   R   K   K   L

271  aaa ttt att aat gaa att cgt cgg cgt gtg ggc gtc gtt ttt cag
      K   F   I   N   E   I   R   R   R   V   G   V   V   F   Q

316  ttt gct gaa tat cag ctt ttt gag caa aca att gaa aaa gac atc
      F   A   E   Y   Q   L   F   E   Q   T   I   E   K   D   I

361  ata ttt ggg gct gtt tca atg gga act cca aaa aat gag gca aaa
      I   F   G   A   V   S   M   G   T   P   K   N   E   A   K

406  aaa att gcc gca gaa ata att gaa tta gtt ggt ctt gat caa agt
      K   I   A   A   E   I   I   E   L   V   G   L   D   Q   S

451  ttt tta caa aaa tca cct ttt gaa ctt tca ggt ggc cag aaa cgc
      F   L   Q   K   S   P   F   E   L   S   G   G   Q   K   R

496  cga gtt gca att gcc gga att tta gca atg gat cct gat att att
      R   V   A   I   A   G   I   L   A   M   D   P   D   I   I

541  ttt ttt gat gaa ccc acg gcc gga ctt gat ccc caa gga acg cta
      F   F   D   E   P   T   A   G   L   D   P   Q   G   T   L

586  aaa atg ctt gaa att ctt gat act tta tat aaa aag ggc aag aca
      K   M   L   E   I   L   D   T   L   Y   K   K   G   K   T

631  atc att ctg gca act cat gat ctt gat agt gtt tta gaa tga aca
      I   I   L   A   T   H   D   L   D   S   V   L   E   W   T

676  aaa cgt tgt att ttt ttt aaa gat ggt aga att att tat gat ggt
      K   R   C   I   F   F   K   D   G   R   I   I   Y   D   G
```

```
721  gat act tat tca att tta gca aat aat aaa ttt tta att gaa aat
      D   T   Y   S   I   L   A   N   N   K   F   L   I   E   N

766  aag atg tta cca act aat tta ctc aat ttt cgc gaa aaa tta atc
      K   M   L   P   T   N   L   L   N   F   R   E   K   L   I

811  aaa att ggt tat cca att tct aat gtt aga tca gta tct gag tta
      K   I   G   Y   P   I   S   N   V   R   S   V   S   E   L

856  atc agt gaa att aat atg cta att caa aag gaa aca aat gca gat
      I   S   E   I   N   M   L   I   Q   K   E   T   N   A   D
```

FIGURE 22

Sequence 22. Represented by clone pAD920.

```
  1  tta aaa tcc cgt ttt tat caa aaa gta aat tcg cag ata gac gtt
      L   K   S   R   F   Y   Q   K   V   N   S   Q   I   D   V

 46  aaa aaa aac aca gat caa gaa aaa gat aaa aaa act gag ccc gaa
      K   K   N   T   D   Q   E   K   D   K   K   T   E   P   E

 91  aaa att aat ttt tat act ctg aaa aaa gta att ttt cct gaa agt
      K   I   N   F   Y   T   L   K   K   V   I   F   P   E   S

136  ttg ctt gag att gat gat tat gcc ttt tat gtc gat agt gca aat
      L   L   E   I   D   D   Y   A   F   Y   V   D   S   A   N

181  tta gat caa aat gaa aaa att caa gaa ctt gat ttt tca aaa gca
      L   D   Q   N   E   K   I   Q   E   L   D   F   S   K   A

226  atg aaa tta agg agg att ggg agt ttc gct ttt caa gga aac aat
      M   K   L   R   R   I   G   S   F   A   F   Q   G   N   N

271  ata aaa acg ctc gtt tta ccc cct tct att aca tca att gga aaa
      I   K   T   L   V   L   P   P   S   I   T   S   I   G   K

316  caa gct ttt gca aaa aac agt tta gaa aca gta gat ttt tcc cag
      Q   A   F   A   K   N   S   L   E   T   V   D   F   S   Q

361  gca aca aaa cta gaa aca att gaa cct ggt gcc ttt ttt gat aat
      A   T   K   L   E   T   I   E   P   G   A   F   F   D   N

406  aaa atc acc gaa ctt gat ttg tca aaa aat ttg att tta gcc gaa
      K   I   T   E   L   D   L   S   K   N   L   I   L   A   E

451  att ttc agg gta gtt ttg aga caa atc aaa tta tca agt
      I   F   R   V   V   L   R   Q   I   K   L   S   S
```

FIGURE 23

Sequence 23. Represented by clone pAD922.

```
  1  act gat cag atc tta att ttc cat ttg gcc aaa act tta gac caa
      T   D   Q   I   L   I   F   H   L   A   K   T   L   D   Q

 46  aaa tat ctt gaa att gac ctt gaa atg ctc gaa aaa ggt aac ttt
      K   Y   L   E   I   D   L   E   M   L   E   K   G   N   F

 91  gaa ttt caa gat ttc att aat ttc tgg caa tct cgg att gaa aaa
      E   F   Q   D   F   I   N   F   W   Q   S   R   I   E   K

136  ata gaa gaa aat tta gcg caa att tct acc gat aaa atc aca gag
      I   E   E   N   L   A   Q   I   S   T   D   K   I   T   E

181  gca aaa atc aac gaa ttt ttt aat tct tat ttg ctt tat ttt gaa
      A   K   I   N   E   F   F   N   S   Y   L   L   Y   F   E

226  aaa tta caa aaa tta ttt agc tca tca tat aat ctt ggc tat gaa
      K   L   Q   K   L   F   S   S   S   Y   N   L   G   Y   E

271  aat gtg gcc aaa tta tat gat tat ttc tat gaa gtc caa aaa att
      N   V   A   K   L   Y   D   Y   F   Y   E   V   Q   K   I

316  tac cga caa aaa cag caa gca aaa gtc gaa ttt gac tac cgc agt
      Y   R   Q   K   Q   Q   A   K   V   E   F   D   Y   R   S

361  gct aaa aaa gat tat gaa gac cag cta aaa aaa ata aag caa gaa
      A   K   K   D   Y   E   D   Q   L   K   K   I   K   Q   E

406  aaa gct ttt ttc att aaa aca tta aat gta aaa gcg ctt aat tta
      K   A   F   F   I   K   T   L   N   V   K   A   L   N   L

451  aaa aaa gag gcc caa ctc gag att gac aaa ttc acc gct caa aac
      K   K   E   A   Q   L   E   I   D   K   F   T   A   Q   N

496  aat ttg ttg act tcc tat att gac gaa ttt aat tat gaa tat aaa
      N   L   L   T   S   Y   I   D   E   F   N   Y   E   Y   K

541  att gca aat aac aaa gcg cta gta aca aca gat cta aaa aat tat
      I   A   N   N   K   A   L   V   T   T   D   L   K   N   Y

586  tca ttt ttt aaa aaa caa gca ata atc aat aag gaa att gcc aaa
      S   F   F   K   K   Q   A   I   I   N   K   E   I   A   K

631  ttt ctt gat agg aga aat att ttg tta ctt gaa aaa aac ctt ttt
      F   L   D   R   R   N   I   L   L   L   E   K   N   L   F

676  tcc ttt ctt aat att tct gag att gaa aaa tta ttt gaa att atg
      S   F   L   N   I   S   E   I   E   K   L   F   E   I   M
```

```
721   aat aat ttc aaa aaa agt caa att gaa aag tat aaa agt ttg act
       N   N   F   K   K   S   Q   I   E   K   Y   K   S   L   T

766   ttc gat aaa aaa gat gaa aaa aat tat aca aat aca aaa tta ttt
       F   D   K   K   D   E   K   N   Y   T   N   T   K   L   F

811   agt caa tta atc cgt acc gaa att atc att ttg gat att caa ggt
       S   Q   L   I   R   T   E   I   I   I   L   D   I   Q   G

856   tta aaa gaa att gcc caa aat cgt aaa aaa act tat caa gaa aaa
       L   K   E   I   A   Q   N   R   K   K   T   Y   Q   E   K

901   gta aat ttt caa aca aaa ttt ctc caa ttt aaa aat aaa tat tca
       V   N   F   Q   T   K   F   L   Q   F   K   N   K   Y   S

946   tat aat aaa aaa aga agt agt ccg caa gcc gaa aat cta gaa aaa
       Y   N   K   K   R   S   S   P   Q   A   E   N   L   E   K

991   ctc aat gaa tta aaa gaa aaa ctg gcc caa aaa gaa gca att tat
       L   N   E   L   K   E   K   L   A   Q   K   E   A   I   Y

1036  gaa gaa gaa aaa gac ctt ttt att aga aaa tat acc tct tgg aaa
       E   E   E   K   D   L   F   I   R   K   Y   T   S   W   K

1081  aca aaa cca gag caa aaa aat
       T   K   P   E   Q   K   N
```

FIGURE 24

Sequence 24. Represented by clones pAD923 and pAD925.

```
  1  tat aat tta aaa aaa gaa act aat ttg agg aaa ttt tta atg tca
      Y   N   L   K   K   E   T   N   L   R   K   F   L   M   S

 46  aaa aaa tct aaa aat tca agc att gaa ttt gat gct att gtt gtc
      K   K   S   K   N   S   S   I   E   F   D   A   I   V   V

 91  ggt ggc ggc cat gct ggg atc gaa gca gtt tat gca tta tta aaa
      G   G   G   H   A   G   I   E   A   V   Y   A   L   L   K

136  aaa aag tta aaa gtt gtt cta ata act ctt gat aag aaa aaa tta
      K   K   L   K   V   V   L   I   T   L   D   K   K   K   L

181  gct tca atg cct tgt aat ccc gca att ggt ggg cca gca aaa gga
      A   S   M   P   C   N   P   A   I   G   G   P   A   K   G

226  att ata act cgc gag atc gat gcc ctt gga gga gtt cag gga aaa
      I   I   T   R   E   I   D   A   L   G   G   V   Q   G   K

271  ttt tca gat tta gca atg atc caa att aaa tat tta aat gaa tca
      F   S   D   L   A   M   I   Q   I   K   Y   L   N   E   S

316  aaa ggt cct gcc gtt tta gca att aga gcc caa att gat aag gaa
      K   G   P   A   V   L   A   I   R   A   Q   I   D   K   E

361  aaa tat tca aaa tta ata tta aag gat ttg aaa aaa cag gaa aat
      K   Y   S   K   L   I   L   K   D   L   K   K   Q   E   N

405  tta tta att atc gag gat ttg gtt agt gaa ctc
      L   L   I   I   E   D   L   V   S   E   L
```

FIGURE 25

Sequence 25. Represented by clone pAD950.

```
  1  caa att gta caa tca gaa cca gaa att tta aat caa aaa ttt ttt
      Q   I   V   Q   S   E   P   E   I   L   N   Q   K   F   F

 46  tta tgt aaa aaa ata cta cag gaa caa aaa tta att agt ttt tgc
      L   C   K   K   I   L   Q   E   Q   K   L   I   S   F   C

 91  gaa caa aaa tta gaa aaa gca aag aaa aat aac caa ttt gaa ctc
      E   Q   K   L   E   K   A   K   K   N   N   Q   F   E   L

136  gcc aac gaa tat cac aaa gcg ctt att gca ctg aaa aaa act aaa
      A   N   E   Y   H   K   A   L   I   A   L   K   K   T   K

181  att gaa caa caa aat att gag ctt aac aac cta aaa aat att gat
      I   E   Q   Q   N   I   E   L   N   N   L   K   N   I   D

226  ttt ctt tat tat agt gaa att ggc gag aat aat tta gta att agt
      F   L   Y   Y   S   E   I   G   E   N   N   L   V   I   S

271  ttt gct ttt tat cgc aat ggt gtt ttt tta tct aat aaa aat ttt
      F   A   F   Y   R   N   G   V   F   L   S   N   K   N   F

316  att att gat att ata ctt aat tat aca gaa gtt tta att aat ttt
      I   I   D   I   I   L   N   Y   T   E   V   L   I   N   F

361  tta aat aat tat tat aaa att aat att tat ccc gat gag tta gta
      L   N   N   Y   Y   K   I   N   I   Y   P   D   E   L   V

406  gtt aaa aat ttt tgg cct aaa aat gct gaa ttt tta gac cca aaa
      V   K   N   F   W   P   K   N   A   E   F   L   D   P   K

451  att aat atc aaa att gga aaa agc tta aaa tat aag cat att tta
      I   N   I   K   I   G   K   S   L   K   Y   K   H   I   L

496  aac act tta gca aaa aat cac caa gat ttt atc agc cat aat ttt
      N   T   L   A   K   N   H   Q   D   F   I   S   H   N   F

541  gac caa gaa att aag aaa aaa att aaa aat cag aaa att tta gaa
      D   Q   E   I   K   K   K   I   K   N   Q   K   I   L   E

586  cta gtt aaa acc agt tta aaa att gaa aat gtt gaa aaa att atg
      L   V   K   T   S   L   K   I   E   N   V   E   K   I   M

631  gca att gac tgc tca aat tta gag tca aac tac ccc aca act gga
      A   I   D   C   S   N   L   E   S   N   Y   P   T   T   G

676  att att ttc tat ata aac gga ata tat gag cga aat tac aat aga
      I   I   F   Y   I   N   G   I   Y   E   R   N   Y   N   R
```

```
721   ttt ttc aat tat agg gga aca aaa aaa ggt gat aca aat tat atg
       F   F   N   Y   R   G   T   K   K   G   D   T   N   Y   M

766   aga cag ggt ttt gaa aaa tat att aaa aat cca aaa ttt cta aaa
       R   Q   G   F   E   K   Y   I   K   N   P   K   F   L   K

811   cct gat ttg att tta gta gat gga gga att caa caa att aat tta
       P   D   L   I   L   V   D   G   G   I   Q   Q   I   N   L

856   att ata gaa att tta aga aaa aat cac ttt gaa att ccg att ttt
       I   I   E   I   L   R   K   N   H   F   E   I   P   I   F

901   gga atg gta aaa aat aaa agg cat aaa act gaa aaa att att gac
       G   M   V   K   N   K   R   H   K   T   E   K   I   I   D

946   tta aat ggt aaa aaa att aac cta gct caa gaa gtt ctt aat ttc
       L   N   G   K   K   I   N   L   A   Q   E   V   L   N   F

991   ttt gct tta att caa gaa aat gtc gat tta ttt gtt aag gaa aaa
       F   A   L   I   Q   E   N   V   D   L   F   V   K   E   K

1036  atg aag aaa aaa caa ata aaa agt tta ttt tct aag gaa
       M   K   K   K   Q   I   K   S   L   F   S   K   E
```

FIGURE 26

Sequence 26. Represented by clone pAD951.

```
  1  tcg aat ata act gac aaa aca gga aaa ctt tta aaa att tct aac
      S   N   I   T   D   K   T   G   K   L   L   K   I   S   N

 46  aat aaa aat act tta att ttt aaa gtt gtt gga gtt ttt gat cct
      N   K   N   T   L   I   F   K   V   V   G   V   F   D   P

 91  gaa aaa gat gac gaa aat att gct att ttt aac aat aat att gaa
      E   K   D   D   E   N   I   A   I   F   N   N   N   I   E

136  aaa tat tct agt gaa tta ctt cca ata gct gct gtg gtt tat ttt
      K   Y   S   S   E   L   L   P   I   A   A   V   V   Y   F

181  gat cat gat aat tta tat aat aat att aat gaa ttt tta aat aaa
      D   H   D   N   L   Y   N   N   I   N   E   F   L   N   K

226  tat agc aaa ccg ggc gtt agt cgt tat tac tcg aca aat ggc ggc
      Y   S   K   P   G   V   S   R   Y   Y   S   T   N   G   G

271  cgg atc aaa ttc
      R   I   K   F
```

FIGURE 27

Sequence 27. Represented by clone pAD977.

```
  1  att tta att aat aat tca att gaa tat aag gaa tta gac cca aac
      I   L   I   N   N   S   I   E   Y   K   E   L   D   P   N

 46  cag tta aga aaa cat att gca cta aca aca aat gaa aac ata att
      Q   L   R   K   H   I   A   L   T   T   N   E   N   I   I

 91  ttc gaa gac act ttg gca aac aac ata act tta tga gat aaa aat
      F   E   D   T   L   A   N   N   I   T   L   W   D   K   N

136  ccc gat tta gat ttg cta aat tct tta ata aaa aag tat aaa att
      P   D   L   D   L   L   N   S   L   I   K   K   Y   K   I

181  gat aat ttt tca aaa cca gaa act gaa att agc tca aaa aat tta
      D   N   F   S   K   P   E   T   E   I   S   S   K   N   L

226  tct gag ggc gaa aaa caa aaa gtt gca ttg gcc aga tta gag tac
      S   E   G   E   K   Q   K   V   A   L   A   R   L   E   Y

271  aaa aat tta gat att tga tgt tta gat gaa gct ctt gat aac att
      K   N   L   D   I   W   C   L   D   E   A   L   D   N   I

316  ttc aag gaa gat gct ttt gaa att tac agt gat tta ctt tca aaa
      F   K   E   D   A   F   E   I   Y   S   D   L   L   S   K

361  ccg aat aaa aca att ttt atc gca agt cac cac att cct gaa aaa
      P   N   K   T   I   F   I   A   S   H   H   I   P   E   K

406  ata aaa ccg atg ttt gac caa ata att gaa att
      I   K   P   M   F   D   Q   I   I   E   I
```

FIGURE 28

Sequence 28. Represented by clone pAD983.

```
  1  tca acg ggc tgc caa att gaa cct gac aaa ccg ctg gta aaa aaa
      S   T   G   C   Q   I   E   P   D   K   P   L   V   K   K

 46  tgg gtt atg ggt gtt tta ttt aat tat agc ttt tat tat tca gga
      W   V   M   G   V   L   F   N   Y   S   F   Y   Y   S   G

 91  att cta agc ata gtt tta gga ttt ttt tct tct gaa ata aca att
      I   L   S   I   V   L   G   F   F   S   S   E   I   T   I

136  ttc ttt ctt caa aca gca ggg gct gat att aat gtt cca gtt tga
      F   F   L   Q   T   A   G   A   D   I   N   V   P   V   W

181  ggc cat cta ata att ggg aca gtt ttt tgt att ttt ttc act agc
      G   H   L   I   I   G   T   V   F   C   I   F   F   T   S

226  ctt aat tat att tca ata aaa aca tca gga tga att gcg ctt gca
      L   N   Y   I   S   I   K   T   S   G   W   I   A   L   A

271  tca aca att tta aaa ttt att cct tta gta ttt gca gtt ttt gca
      S   T   I   L   K   F   I   P   L   V   F   A   V   F   A

316  gga att cta ttt cca aaa act tat aat gcc ggc ggt tct aat gcc
      G   I   L   F   P   K   T   Y   N   A   G   G   S   N   A

361  ttt gtt caa aca gct caa ata gtt tta att ttg caa aat t
      F   V   Q   T   A   Q   I   V   L   I   L   Q   N
```

FIGURE 29

Sequence 29. Represented by clone pAD984.

```
1    tta aaa agt gaa aac caa aaa gaa aca gca aat tta aat act act
      L   K   S   E   N   Q   K   E   T   A   N   L   N   T   T

46   ttt act caa aca att agt aaa aaa gat atc gaa ata acc aat tta
      F   T   Q   T   I   S   K   K   D   I   E   I   T   N   L

91   aga aat gaa att ggc aaa ttt ctt gat gaa aaa gat aaa atg cga
      R   N   E   I   G   K   F   L   D   E   K   D   K   M   R

136  agt gac att ctt gca aat gat gat gag ata aag gcg atg agg agt
      S   D   I   L   A   N   D   D   E   I   K   A   M   R   S

181  gaa att tct caa cta aaa gaa gca aat gcc aac cta caa aat gtc
      E   I   S   Q   L   K   E   A   N   A   N   L   Q   N   V

226  aag tta gaa gaa att tca aat tta aaa cta gaa cat aag gac gaa
      K   L   E   E   I   S   N   L   K   L   E   H   K   D   E

271  att aat gaa aaa gac cgt aaa att agt tat tta gag aat aaa ttt
      I   N   E   K   D   R   K   I   S   Y   L   E   N   K   F

316  aac gac ttg gaa gaa gaa aaa aat aat tca att caa aat gct gta
      N   D   L   E   E   E   K   N   N   S   I   Q   N   A   V

361  agt caa aaa aca cga gaa ata aag gaa aaa att gaa aaa gag cta
      S   Q   K   T   R   E   I   K   E   K   I   E   K   E   L

406  gaa att aaa tgg gga aga aaa aat aaa aca gga aaa atc aga ttt
      E   I   K   W   G   R   K   N   K   T   G   K   I   R   F

451  aag agg aaa att tta agg agc aaa tta ata aac cag gag aaa aaa
      K   R   K   I   L   R   S   K   L   I   N   Q   E   K   K

496  ttc aag att aga aga aga att aaa tta
      F   K   I   R   R   R   I   K   L
```

FIGURE 30

Sequence 30. Represented by clone pAD994.

```
  1  att aaa cac ttt ttt aaa aga ttt gaa atg tat aaa cga tta gtt
      I   K   H   F   F   K   R   F   E   M   Y   K   R   L   V

 46  cag gaa ttc ttt cct aaa tta gat ttt gaa aat tta gaa aaa tac
      Q   E   F   F   P   K   L   D   F   E   N   L   E   K   Y

 91  gta aat tta att gaa ttt agt aat aaa aac ttt aat tta acc gct
      V   N   L   I   E   F   S   N   K   N   F   N   L   T   A

136  ttt tct ggt gat att ctt tga aaa gag gga att ttt gag tca att
      F   S   G   D   I   L   W   K   E   G   I   F   E   S   I

181  ttt aca atg aat ttc att gtt ggt tta gta aat aat aaa gaa aat
      F   T   M   N   F   I   V   G   L   V   N   N   K   E   N

226  aaa aaa tta aaa att ttg gat att ggg gct gga tca ggt ttt cct
      K   K   L   K   I   L   D   I   G   A   G   S   G   F   P

271  tca att cct ttt ttg att aca aac cca gaa att gag cta aca att
      S   I   P   F   L   I   T   N   P   E   I   E   L   T   I

316  tct gag tca atg caa aaa aga tgc cag ttt tta aag gat gtt tct
      S   E   S   M   Q   K   R   C   Q   F   L   K   D   V   S

361  gaa aaa tta gat ttg aaa ttc aat tta att tgc aaa cca gtt caa
      E   K   L   D   L   K   F   N   L   I   C   K   P   V   Q

406  gaa att aat cca caa aaa ttt gat ata ata act gcc aga gca gtg
      E   I   N   P   Q   K   F   D   I   I   T   A   R   A   V

451  gca aat ttg gaa aag ctt gag aaa att aca aaa aaa att cat ttt
      A   N   L   E   K   L   E   K   I   T   K   K   I   H   F

496  cca aaa acg ctt tta gct ttt att aaa ggg ccc aaa gtt ttt aat
      P   K   T   L   L   A   F   I   K   G   P   K   V   F   N

541  gaa gtt caa aat tgt aaa aat tgt aat tat aaa atc att aaa gtt
      E   V   Q   N   C   K   N   C   N   Y   K   I   I   K   V

586  aat aat aat ata aat aaa aaa att ttt atc gca ttt aaa caa gtt
      N   N   N   I   N   K   K   I   F   I   A   F   K   Q   V

631  tct
      S
```

FIGURE 31

Sequence 31. Represented by clone pAD1005.

```
1    atg aaa aaa tta tta gtt att ttg ctt gat aaa ttc cag gat att
      M   K   K   L   L   V   I   L   L   D   K   F   Q   D   I

46   gaa ctt aca act ttt att tcc ctg att aaa aaa gca gaa att ttt
      E   L   T   T   F   I   S   L   I   K   K   A   E   I   F

91   aca gat att gaa ttt ttt aac cct aaa aat aat aaa tta gta ata
      T   D   I   E   F   F   N   P   K   N   N   K   L   V   I

136  ggt caa ttc gga gtt gta tca att caa gca cat aat cac tgg aaa
      G   Q   F   G   V   V   S   I   Q   A   H   N   H   W   K

181  tca gat gac ttt gat gct gtt ttt att ccg ggg ggt ttt gcg gcc
      S   D   D   F   D   A   V   F   I   P   G   G   F   A   A

226  caa tta ttc cgc aag gat tca aaa tca att caa ctt gtg agc gag
      Q   L   F   R   K   D   S   K   S   I   Q   L   V   S   E

271  ttt ttt gcg caa aac aaa cat att ttt gcc att tgt gat gca cca
      F   F   A   Q   N   K   H   I   F   A   I   C   D   A   P

316  aat gca att ttt gaa cta aaa tta gca gaa aat tat caa ttt agt
      N   A   I   F   E   L   K   L   A   E   N   Y   Q   F   S

361  tca tat cca aac caa cat aat tcc aaa att aga cta aga caa gat
      S   Y   P   N   Q   H   N   S   K   I   R   L   R   Q   D

406  tcg tta gta act att gac cgc aat tat att tcg gca aga aat gca
      S   L   V   T   I   D   R   N   Y   I   S   A   R   N   A

451  gca agt tcg gca gat ttt gct ttc gtt gta att gaa aag ctg gga
      A   S   S   A   D   F   A   F   V   V   I   E   K   L   G

496  tca aaa gag tta gct caa aaa att aga aat gga ttt tat ctt
      S   K   E   L   A   Q   K   I   R   N   G   F   Y   L
```

FIGURE 32

Sequence 32. Represented by clone pAD1016.

```
  1  tta atc gtt ttt gct tat atg atg ttg gtt gta atg aat tga ggt
      L   I   V   F   A   Y   M   M   L   V   V   M   N   W   G

 46  ttt gcc tct gcc gga ctt aac ggt aaa gcg gga ata agt ggt tat
      F   A   S   A   G   L   N   G   K   A   G   I   S   G   Y

 91  tta ggt cac ttt ttt cca aat gct aat gaa gcc cca gga acc gtt
      L   G   H   F   F   P   N   A   N   E   A   P   G   T   V

136  gta aat caa gca gtt aac tgg ggt atc aca att ggt cgt gga att
      V   N   Q   A   V   N   W   G   I   T   I   G   R   G   I

181  gga tca gtt ctt gtt ggt tga tta att gtg aaa att tcg cat aaa
      G   S   V   L   V   G   W   L   I   V   K   I   S   H   K

226  tat aca gta att ttg tct tta ttt ttt atg ctt ttt gga att att
      Y   T   V   I   L   S   L   F   F   M   L   F   G   I   I

271  gcc cct tat tca cca act tat gcc ggg ttt ata att ctt aga aca
      A   P   Y   S   P   T   Y   A   G   F   I   I   L   R   T

316  att ttt gca att ggc gga aca atg cag att att tta att caa cca
      I   F   A   I   G   G   T   M   Q   I   I   L   I   Q   P

361  gtt gtc tca aat tat tta aat caa agg caa aaa gct gtt att tca
      V   V   S   N   Y   L   N   Q   R   Q   K   A   V   I   S

406  caa gtt ttc ccc ttt ttt tta tcc aat tgg aac aat aat tac gct
      Q   V   F   P   F   F   L   S   N   W   N   N   N   Y   A

451  tat tcc ttt tgc agg aat tat ttg gtc aag agc tca
      Y   S   F   C   R   N   Y   L   V   K   S   S
```

FIGURE 33

Sequence 33. Represented by clone pAD1020.

```
1    tct gat cgt ttt cca gtt aca agt tta gaa aaa tta ttt caa ttt
      S   D   R   F   P   V   T   S   L   E   K   L   F   Q   F

46   gtc gct aat tca gcg cct att ttt gaa aaa ttc aaa aaa gca aaa
      V   A   N   S   A   P   I   F   E   K   F   K   K   A   K

91   gaa aaa ttt tat caa gca aaa ttt ggg act aag atg aat agt tga
      E   K   F   Y   Q   A   K   F   G   T   K   M   N   S   W

136  gac cgt tta gtt cca tta gtt gag aca aaa aat aat tat tct gtt
      D   R   L   V   P   L   V   E   T   K   N   N   Y   S   V

181  gaa gat gca caa aaa ata gtg ctt ggg gca atc aaa cca tta ggt
      E   D   A   Q   K   I   V   L   G   A   I   K   P   L   G

226  caa gaa tat aaa gat gtt gta gaa aaa gca ttt agc caa aga tga
      Q   E   Y   K   D   V   V   E   K   A   F   S   Q   R   W

271  att gac tat cat tat gtt gat tca aaa aga tct ggt gct tat tca
      I   D   Y   H   Y   V   D   S   K   R   S   G   A   Y   S

316  att ggg ggt tca tat ggg ctt gaa aaa aaa tat att tta atg aat
      I   G   G   S   Y   G   L   E   K   K   Y   I   L   M   N

361  tat gac ttt act ata aac gca gtt cat act tta gca cat gaa tta
      Y   D   F   T   I   N   A   V   H   T   L   A   H   E   L

406  ggt cat tcg ctc cat tct tat tat tct gat aaa aac cag aat tat
      G   H   S   L   H   S   Y   Y   S   D   K   N   Q   N   Y

451  cat aat
      H   N
```

FIGURE 34

Sequence 34. Represented by clone pAD1027.

```
1    gaa tta att agg gaa aat tta tca ctt gca aaa tca ttt tat gtt
      E   L   I   R   E   N   L   S   L   A   K   S   F   Y   V

46   gat aaa aat aat aat cct tgg ata tca aca aca aaa aat ttt gaa
      D   K   N   N   N   P   W   I   S   T   T   K   N   F   E

91   aac tta ttt gat tat gta caa agc gag cat cta att aat act aat
      N   L   F   D   Y   V   Q   S   E   H   L   I   N   T   N

136  aaa ata aaa aat tat atc aca aac ata aat ttt aaa atc aaa aaa
      K   I   K   N   Y   I   T   N   I   N   F   K   I   K   K

181  aat agt gaa ata cct gct tta gaa ctt aat aat ttg cta aaa gat
      N   S   E   I   P   A   L   E   L   N   N   L   L   K   D

226  gat aaa att cgg ctt gaa ata aat gtt gat atc tca aag tga gtc
      D   K   I   R   L   E   I   N   V   D   I   S   K   W   V

271  caa caa aaa cta att aaa att tta agt ttt aag ttt gat tgg gac
      Q   Q   K   L   I   K   I   L   S   F   K   F   D   W   D

316  cta aaa cca gac ctg aat cag tat gcc cgg att ttt gca caa aat
      L   K   P   D   L   N   Q   Y   A   R   I   F   A   Q   N

361  cta ccc gag cca aaa tct gag gta ttc tta cta aga aaa gat gaa
      L   P   E   P   K   S   E   V   F   L   L   R   K   D   E

406  aat tca gca gcg tga act agt aaa aaa cta gta aat ata ata aat
      N   S   A   A   W   T   S   K   K   L   V   N   I   I   N

451  aaa att aag gga ttt aac aat gga tta gac cca gaa aat cct gat
      K   I   K   G   F   N   N   G   L   D   P   E   N   P   D

496  tta agg tta gtt agc caa ctt tat tta ctt gat ttt ggc aaa att
      L   R   L   V   S   Q   L   Y   L   L   D   F   G   K   I

541  ggt gat gaa aat gct ata gaa aat ttt aaa ggg att
      G   D   E   N   A   I   E   N   F   K   G   I
```

FIGURE 35

Sequence 35. Represented by clone pAD1037.

```
  1  cat atg tta att gaa gtt tta ata att cac tac cgt caa gtt cag
      H   M   L   I   E   V   L   I   I   H   Y   R   Q   V   Q

 46  tat ggc caa agt att aaa aaa tca gta att tat aac tta ata aca
      Y   G   Q   S   I   K   K   S   V   I   Y   N   L   I   T

 91  acc ctg att tta gtg ccg att att aca gtt ggc gcc ttt ttg aac
      T   L   I   L   V   P   I   I   T   V   G   A   F   L   N

136  cgt ttt ttt att aaa aca ggc tga cta ata cca ttt ttt aat gtt
      R   F   F   I   K   T   G   W   L   I   P   F   F   N   V

181  tct ggc ggg gca att tta agt ttt gtt gtc ata att gag tta gtt
      S   G   G   A   I   L   S   F   V   V   I   I   E   L   V

226  cca gaa ttt atc cat tta aga aat aac cct tct ttt cag tga cat
      P   E   F   I   H   L   R   N   N   P   S   F   Q   W   H

271  ttt tct ctt ttt ttg ttt gct tta gga att att tta gcc tta att
      F   S   L   F   L   F   A   L   G   I   I   L   A   L   I

316  att tta att tac atg aac att aag cgc cgt aga tcc
      I   L   I   Y   M   N   I   K   R   R   R   S
```

FIGURE 36

Sequence 36. Represented by clone pAD1038.

```
  1  gaa ttc gaa aaa cga att aag gca att ttg caa gaa att gag caa
      E   F   E   K   R   I   K   A   I   L   Q   E   I   E   Q

 46  aat tcc gat caa gtt att att ttt att gat gaa att cac ctt cta
      N   S   D   Q   V   I   I   F   I   D   E   I   H   L   L

 91  att gga aca gga tct tct ggg act gat tca atg gat ttt gcc aat
      I   G   T   G   S   S   G   T   D   S   M   D   F   A   N

136  atc cta aaa cca att atg gct cgc gga cag att aaa tta atc ggg
      I   L   K   P   I   M   A   R   G   Q   I   K   L   I   G

181  gct acc aca aat tcc gaa tat cgc tta tat atc gaa aaa gat ggc
      A   T   T   N   S   E   Y   R   L   Y   I   E   K   D   G

226  gcc ctt gaa aga aga atg caa aaa gta gaa att tta gag cct tca
      A   L   E   R   R   M   Q   K   V   E   I   L   E   P   S

271  gtt att gat aca att aat att tta cgg gga att aag gaa agg cta
      V   I   D   T   I   N   I   L   R   G   I   K   E   R   L

316  gaa aat ttc cat caa gta aaa att aag gat tct gct ctt gtt ttt
      E   N   F   H   Q   V   K   I   K   D   S   A   L   V   F

361  gct aca aaa gcg gca aat cgt tac att ttt gac cgc ttt cta cct
      A   T   K   A   A   N   R   Y   I   F   D   R   F   L   P

406  gat aaa gct atc gat tta gtc gat gaa gct gct gct tct tta aaa
      D   K   A   I   D   L   V   D   E   A   A   A   S   L   K

451  gtt gaa atc aac tac caa cca gaa aaa ctt gaa aaa gca aag cgc
      V   E   I   N   Y   Q   P   E   K   L   E   K   A   K   R

496  gag cta att tat tta aaa atg gaa gaa att aac tcg caa aaa caa
      E   L   I   Y   L   K   M   E   E   I   N   S   Q   K   Q

541  gat aat tca gaa tta aaa tcc aaa att gaa aat ctt gaa aat gaa
      D   N   S   E   L   K   S   K   I   E   N   L   E   N   E

586  gta aaa aaa tta caa gat caa tgg gat caa tca aaa aaa tca gcc
      V   K   K   L   Q   D   Q   W   D   Q   S   K   K   S   A

631  tct gaa atc gct agc tta tcc cag gaa ctt gaa aaa cta aaa tat
      S   E   I   A   S   L   S   Q   E   L   E   K   L   K   Y

676  caa caa aat tac tta atg gaa caa gga gac tac caa aaa gcc gcc
      Q   Q   N   Y   L   M   E   Q   G   D   Y   Q   K   A   A
```

```
721   gag att aaa tac gga aaa att ccc aaa ata agt aaa aaa tta ggc
       E   I   K   Y   G   K   I   P   K   I   S   K   K   L   G

766   gaa att aaa gca aga agg cag gaa att tcc aat gtt cta gac gaa
       E   I   K   A   R   R   Q   E   I   S   N   V   L   D   E

811   agt cag atc gca aag gtt gtc tct aat tga aca aaa att ccg att
       S   Q   I   A   K   V   V   S   N   W   T   K   I   P   I

856   gaa aaa ctt tta gaa tca gaa att caa aaa tat ttg aat tta gaa
       E   K   L   L   E   S   E   I   Q   K   Y   L   N   L   E

901   aaa aat tta gca aaa tcg ctt aag ggt caa aat cag gca att aag
       K   N   L   A   K   S   L   K   G   Q   N   Q   A   I   K

946   gct gtt tca gat gcg att ttg cgg ttt aaa gct aaa att aat gat
       A   V   S   D   A   I   L   R   F   K   A   K   I   N   D

991   gaa tcc cgc cca att tca tca ttt ttc ttt atg gga cca act ggg
       E   S   R   P   I   S   S   F   F   F   M   G   P   T   G

1036  gtg gga aaa act gaa ctt gct aga gct tta gct ctt aat tta ttt
       V   G   K   T   E   L   A   R   A   L   A   L   N   L   F

1081  aat aat aaa aac caa ata atc cgt ctt gat atg tca gaa tat atg
       N   N   K   N   Q   I   I   R   L   D   M   S   E   Y   M

1126  gaa aaa cat agt gtt tca aag cta att ggg gct cct ccg ggt tat
       E   K   H   S   V   S   K   L   I   G   A   P   P   G   Y

1171  att ggt ttt gaa caa ggt ggt aat cta aca aat aaa gta aga cta
       I   G   F   E   Q   G   G   N   L   T   N   K   V   R   L

1216  aat cct tat tcg att att ttg ctt gat gaa att gaa aaa gct cat
       N   P   Y   S   I   I   L   L   D   E   I   E   K   A   H

1261  ccg gaa gta atc aac att ttt tta caa att ctt gat aat ggt gaa
       P   E   V   I   N   I   F   L   Q   I   L   D   N   G   E

1306  att gtt gat agt aag tca caa aaa gta aat ttt cgc aat aca att
       I   V   D   S   K   S   Q   K   V   N   F   R   N   T   I

1351  ata att atg acc tca aat atc ggt gct aat aaa att ctt gag ggt
       I   I   M   T   S   N   I   G   A   N   K   I   L   E   G

1396  aaa aag atg aat gaa att gag gca aaa aag gaa ctt tta aga tat
       K   K   M   N   E   I   E   A   K   K   E   L   L   R   Y

1441  tta aag cca gaa ttt ctc aac cga att gat gaa att atc gta ttt
       L   K   P   E   F   L   N   R   I   D   E   I   I   V   F
```

```
1486  aat cct tta aat tat gat ata att ttt gaa att att gaa ctt gaa
       N   P   L   N   Y   D   I   I   F   E   I   I   E   L   E

1531  cta aag gat ttg caa aat cgt cta aag gaa aat aat ttt gag att
       L   K   D   L   Q   N   R   L   K   E   N   N   F   E   I

1576  gaa ttt gaa aaa tca gtc aaa aat tga att tta gag ttt gga tat
       E   F   E   K   S   V   K   N   W   I   L   E   F   G   Y

1621  gat aaa aat ttt ggt gcc agg cca att aag cgc ttt att aag aaa
       D   K   N   F   G   A   R   P   I   K   R   F   I   K   K

1666  gaa att gaa aat ttt gtt gcc aaa aaa ata gtg gcc gaa gaa att
       E   I   E   N   F   V   A   K   K   I   V   A   E   E   I

1711  tta aaa gat aaa aaa tac aat tta tct ttt aaa aat gat aaa ttg
       L   K   D   K   K   Y   N   L   S   F   K   N   D   K   L

1756  cat ctt aat gaa agc gaa aat
       H   L   N   E   S   E   N
```

FIGURE 37

Sequence 37. Represented by clone pAD1040

```
  1  atg gta aaa tct aca aaa cat ttc aaa ttt atc ctt tga aat tga
      M   V   K   S   T   K   H   F   K   F   I   L   W   N   W

 46  tta tat ttg att ttt acg att ttt ttt aaa att tat ctc att gtt
      L   Y   L   I   F   T   I   F   F   K   I   Y   L   I   V

 91  gct cct tat ttt att ttt act ttt att cta aat gaa aat tta act
      A   P   Y   F   I   F   T   F   I   L   N   E   N   L   T

136  ttt ttt tgg gta gcc aca aca tct ttt tta ggg gtt aga att ttt
      F   F   W   V   A   T   T   S   F   L   G   V   R   I   F

181  aat atc ttt tta gat ttt atg aat caa gca tat ttt aaa ggg ttt
      N   I   F   L   D   F   M   N   Q   A   Y   F   K   G   F

226  ttg atc ttt cat aag atg aaa ctt gcc gaa aaa ata aca aat ttt
      L   I   F   H   K   M   K   L   A   E   K   I   T   N   F

271  ttg gaa aaa acg act tac aaa aaa tat aac gaa aat tca agt ggg
      L   E   K   T   T   Y   K   K   Y   N   E   N   S   S   G

316  ttt tac tat tcg gaa att gaa aat aca ata gaa aaa agc gtt tca
      F   Y   Y   S   E   I   E   N   T   I   E   K   S   V   S

361  caa ttt tat gca aat tta ttg tcc ttt ttg caa act ctt tcc ata
      Q   F   Y   A   N   L   L   S   F   L   Q   T   L   S   I

406  att ttg atg act tta ggt tta ttt ttt tat ata aac tgg att tta
      I   L   M   T   L   G   L   F   F   Y   I   N   W   I   L

451  gcg tta att att gtc ggt gtt ata acc ttt ttt gta att aca act
      A   L   I   I   V   G   V   I   T   F   F   V   I   T   T

496  tct tta cta tct aaa aaa tta acc aaa ctt caa tcc gca aaa ttg
      S   L   L   S   K   K   L   T   K   L   Q   S   A   K   L

541  caa gca att tcg gat ttt aac aat tct tta agc act tat ctt tta
      Q   A   I   S   D   F   N   N   S   L   S   T   Y   L   L

586  act ttg ccg caa tta aaa acc tta aat tct gat gat aaa ttc gaa
      T   L   P   Q   L   K   T   L   N   S   D   D   K   F   E

631  ttt ata att aat aaa aga aac aag aaa aat tga ata act aga gaa
      F   I   I   N   K   R   N   K   K   N   W   I   T   R   E

676  aaa tat ggt ata ttt tcc gac tta att tca ttt ttt aat gaa tat
      K   Y   G   I   F   S   D   L   I   S   F   F   N   E   Y
```

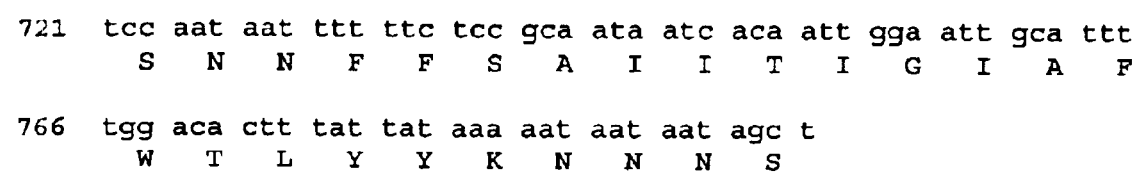

```
721  tcc aat aat ttt ttc tcc gca ata atc aca att gga att gca ttt
      S   N   N   F   F   S   A   I   I   T   I   G   I   A   F

766  tgg aca ctt tat tat aaa aat aat aat agc t
      W   T   L   Y   Y   K   N   N   N   S
```

Figure 38

Sequence 38. Represented by clone pAD702.

```
  1  tct tat gag aaa aaa tat tta cct ttg cta ata gtc cct gga att
      S   Y   E   K   K   Y   L   P   L   L   I   V   P   G   I

 46  ttt ggc gct att tta ttt ttt ctt ttt att aaa aca ctt tta gac
      F   G   A   I   L   F   F   L   F   I   K   T   L   L   D

 91  tat aaa gca atc aaa aaa tct gtt att tat ttt cgt tcc cag ttg
      Y   K   A   I   K   K   S   V   I   Y   F   R   S   Q   L

136  caa aat aat gca aat cga ctt gaa atg cca cca atg att cca tga
      Q   N   N   A   N   R   L   E   M   P   P   M   I   P   W

181  ctt gta aaa aaa gtg aat caa aaa gag gta aat gct atc tga ctt
      L   V   K   K   V   N   Q   K   E   V   N   A   I   W   L

226  agc ggc ttt act ttg ttt gca aca att atg atg ggc tta act tac
      S   G   F   T   L   F   A   T   I   M   M   G   L   T   Y

271  tga gtg tta tta aaa tat tat ccg gag aaa aat att caa aat tct
      W   V   L   L   K   Y   Y   P   E   K   N   I   Q   N   S

316  gcc gaa tat ata act gca atg gca gta aat ggc gct ttg ttt ata
      A   E   Y   I   T   A   M   A   V   N   G   A   L   F   I

361  gtt atg cta att tat gat tta atg ctt cgt cgg cgt ttg gga aat
      V   M   L   I   Y   D   L   M   L   R   R   R   L   G   N

406  att gaa gca att ttt ggt ccc att tat cat aaa agt ttt gat ata
      I   E   A   I   F   G   P   I   Y   H   K   S   F   D   I

451  ggt
      G
```

Figure 39

Sequence 39. Represented by clone pAD763.

```
1   gat ctt tgt gtt att ttt gtt aat aaa acc aag ttt aaa agt cat
     D   L   C   V   I   F   V   N   K   T   K   F   K   S   H

46  ttc ccc tgg ttt gtc agt ggt ttt aac atc ata ata ata gac aaa
     F   P   W   F   V   S   G   F   N   I   I   I   I   D   K

91  ata att ctt
     I   I   L
```

Figure 40

Sequence 40. Represented by clone pAD766.

```
1   gat caa caa aaa cca caa cca aaa gaa gaa aaa gaa gaa aaa caa
     D   Q   Q   K   P   Q   P   K   E   E   K   E   E   K   Q

46  gaa aaa gaa gaa aaa aaa ccg ccg ata gtt caa ggt cct agt cca
     E   K   E   E   K   K   P   P   I   V   Q   G   P   S   P

91  aaa cca caa aag att gaa aat atc ggt ctt gtt aat gat ttt tat
     K   P   Q   K   I   E   N   I   G   L   V   N   D   F   Y

136 aaa tac aag ttt aac gat aaa att cat aaa ttt gaa ccg act gag
     K   Y   K   F   N   D   K   I   H   K   F   E   P   T   E

181 tat tat aaa aat aca gca aat ttt tct cag ggt ggc ctt tat agt
     Y   Y   K   N   T   A   N   F   S   Q   G   G   L   Y   S

226 gca aat ttg ctc gaa tta gaa aag gaa ata aag aaa caa gat ccg
     A   N   L   L   E   L   E   K   E   I   K   K   Q   D   P

271 gat aat cct aaa ata ttt tat gtt caa aga cga att gat att ggt
     D   N   P   K   I   F   Y   V   Q   R   R   I   D   I   G

316 ggt ttt cta aca aaa ggc aca ctt tta cca ttt caa ccc gca aat
     G   F   L   T   K   G   T   L   L   P   F   Q   P   A   N

361 ctt gag aat aat tta tca agc ctt tcg ctt ttt gat aga tat tcc
     L   E   N   N   L   S   S   L   S   L   F   D   R   Y   S

406 caa ttt ctg agg agc ggc aga ttc gat aac aat tat tat ata att
     Q   F   L   R   S   G   R   F   D   N   N   Y   Y   I   I

451 gga tcc gat aag gtt gag gaa ttt gat agg ttg aaa aga
     G   S   D   K   V   E   E   F   D   R   L   K   R
```

Figure 41

Sequence 41. Represented by clone pAD957.

```
  1  agc tat ttt agt att ata agc cct ttg ttt ttg gct gtt tct tgc
      S   Y   F   S   I   I   S   P   L   F   L   A   V   S   C

 46  aca aac att ata att agc aaa tct gaa tta tca aaa ata gaa agt
      T   N   I   I   I   S   K   S   E   L   S   K   I   E   S

 91  aat att ttt aat ttt ata ata aac gaa aat gaa aaa aat tta act
      N   I   F   N   F   I   I   N   E   N   E   K   N   L   T

136  aga ttt acc gca act tta gta aaa aaa act aat aat aac ttg act
      R   F   T   A   T   L   V   K   K   T   N   N   N   L   T

181  ttt gtc agt act ttt cat tcg cta aat tca ata aaa aac aat ata
      F   V   S   T   F   H   S   L   N   S   I   K   N   N   I

226  cag caa caa gtt ttt gat att ttt tta caa caa ttt agt gtg aaa
      Q   Q   Q   V   F   D   I   F   L   Q   Q   F   S   V   K

271  aat tta gaa act aaa tta aaa tca aaa att aga gtt gaa tat gaa
      N   L   E   T   K   L   K   S   K   I   R   V   E   Y   E

316  aat aaa gaa aaa gat atc ata gtt ttt tcg cta gat ata aag gaa
      N   K   E   K   D   I   I   V   F   S   L   D   I   K   E

361  ccc tta ttg ttg aga att tcg gat tct att gat ttt cag gtt cta
      P   L   L   L   R   I   S   D   S   I   D   F   Q   V   L

406  gag gat ttt aca aac aca aaa aat agc cta ttt agc tta agg ttt
      E   D   F   T   N   T   K   N   S   L   F   S   L   R   F

451  ctc acg gat ctt aaa cga aga ttt
      L   T   D   L   K   R   R   F
```

Figure 42

Sequence 42. Represented by clone pAD996.

```
 1  agc tat cta tta att atg atg ccg cag ggg gaa cct atc aca cta
     S   Y   L   L   I   M   M   P   Q   G   E   P   I   T   L

46  ctg gtt aag gtc att acg cta gcg gtt atg cac tca gat gaa aat
     L   V   K   V   I   T   L   A   V   M   H   S   D   E   N

91  gct gaa agg tac ata aac tct gat gat ccg atc
     A   E   R   Y   I   N   S   D   D   P   I
```

LEGEND TO FIGURES

The letters used to denote amino acids are as follows.

| | |
|---|---|
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The Mycoplasma genetic code varies from the universal genetic code in that UGA (TGA) codes for tryptophan rather than the usual stop signal. In the hypothetical translations presented in Figures 1 - 42 TGA has been assumed to code for a tryptophan residue.

SEQUENCE LISTING

<160> NUMBER OF SEQ ID NOS: 84

<210> SEQ ID NO 1
<211> LENGTH: 1125
<212> TYPE: DNA
<213> ORGANISM: Artificial Sequence
<220> FEATURE:
<223> OTHER INFORMATION: Description of Artificial Sequence:Clone pAD612

<400> SEQUENCE: 1

```
atggcaaaac aagattttta taaaattctg ggagttgaaa aatcagcatc actaacagaa     60

ataaaaaaag cttatcgaaa tttagtaaat atttatcatc ctgataaaaa tacaaaaaaa    120

tcagctgaag aacaaaaaca agctgaggcc aaatttaaag aaatccagga agcctacgaa    180

attttatctg atgaaacaaa gcgaaaacag tacgataaat tcggtcatgc cgcttttgat    240

cagcaatttg gtggtgggtc tagtggcttt tcaggatttg attttggcga tattttttca    300

agttttacct ctggttttgg ttttggcggc tcacaagaac aaaaatatag tcgtccttta    360

aagggcgaaa attttcaagc taaaatttat atcagtttta tcgagtcaat tctcggaaaa    420

gaaatctccc agaaattaac aaaatacgat caatgtgata actgtaaggg ttcaggcgct    480

aattcttctt ctgatattac aacttgctat aattgtcaag gtcggggaat gcaaactgag    540

gtcttaaata tcccgggatt tggtcgggtt cagaacaaaa caacttgttc agtttgttta    600

ggttccggga aaaacattac aaaaattgca aagaagtgcc atggaaaaac tatagttgag    660

acaaaagagg aagtaactat taaaattccg gccggaatcc aggatggaat gtttatccgc    720

gtggccggat ttggtggacc gggacacaaa ggcgggcctt ctggagatct tcatcttgag    780

attaatgttc gtcagcataa acattttact agatccggaa atgatattca tgtgaatatg    840

ccagtttcaa taattgatat tatcaaccaa aatactgtcg aagttcccaa cccaaccggt    900

ttgaaaaaag ttagacttta tgattattat aaatccggtc caattgttaa tgttcttcct    960

gctggggctc ctgatccaaa aaatccaaga attattggcg atctcaaggt tcatttaatt   1020

ttttatatcc ccgaatttag tccccgtcaa aaagatgagc tcaaccaggt tttgctcaa   1080

atcaatgata aaacaaaggc aaaatgacta aaagaatttc aataa                  1125
```

<210> SEQ ID NO 2
<211> LENGTH: 368
<212> TYPE: PRT
<213> ORGANISM: Artificial Sequence
<220> FEATURE:
<223> OTHER INFORMATION: Description of Artificial Sequence:Deduced protein sequence from clone pAD612

<400> SEQUENCE: 2

```
Met Ala Lys Gln Asp Phe Tyr Lys Ile Leu Gly Val Glu Lys Ser Ala
  1               5                  10                  15

Ser Leu Thr Glu Ile Lys Lys Ala Tyr Arg Asn Leu Val Asn Ile Tyr
             20                  25                  30

His Pro Asp Lys Asn Thr Lys Lys Ser Ala Glu Glu Gln Lys Gln Ala
         35                  40                  45

Glu Ala Lys Phe Lys Glu Ile Gln Glu Ala Tyr Glu Ile Leu Ser Asp
     50                  55                  60

Glu Thr Lys Arg Lys Gln Tyr Asp Lys Phe Gly His Ala Ala Phe Asp
 65                  70                  75                  80

Gln Gln Phe Gly Gly Gly Ser Ser Gly Phe Ser Gly Phe Asp Phe Gly
```

-continued

```
                85                  90                  95

Asp Ile Phe Ser Ser Phe Thr Ser Gly Phe Gly Phe Gly Gly Ser Gln
            100                 105                 110

Glu Gln Lys Tyr Ser Arg Pro Leu Lys Gly Glu Asn Phe Gln Ala Lys
        115                 120                 125

Ile Tyr Ile Ser Phe Ile Glu Ser Ile Leu Gly Lys Glu Ile Ser Gln
    130                 135                 140

Lys Leu Thr Lys Tyr Asp Gln Cys Asp Asn Cys Lys Gly Ser Gly Ala
145                 150                 155                 160

Asn Ser Ser Ser Asp Ile Thr Thr Cys Tyr Asn Cys Gln Gly Arg Gly
                165                 170                 175

Met Gln Thr Glu Val Leu Asn Ile Pro Gly Phe Gly Arg Val Gln Asn
            180                 185                 190

Lys Thr Thr Cys Ser Val Cys Leu Gly Ser Gly Lys Asn Ile Thr Lys
        195                 200                 205

Ile Ala Lys Lys Cys His Gly Lys Thr Ile Val Glu Thr Lys Glu Glu
    210                 215                 220

Val Thr Ile Lys Ile Pro Ala Gly Ile Gln Asp Gly Met Phe Ile Arg
225                 230                 235                 240

Val Ala Gly Phe Gly Gly Pro Gly His Lys Gly Gly Pro Ser Gly Asp
                245                 250                 255

Leu His Leu Glu Ile Asn Val Arg Gln His Lys His Phe Thr Arg Ser
            260                 265                 270

Gly Asn Asp Ile His Val Asn Met Pro Val Ser Ile Ile Asp Ile Ile
        275                 280                 285

Asn Gln Asn Thr Val Glu Val Pro Asn Pro Thr Gly Leu Lys Lys Val
    290                 295                 300

Arg Leu Tyr Asp Tyr Tyr Lys Ser Gly Pro Ile Val Asn Val Leu Pro
305                 310                 315                 320

Ala Gly Ala Pro Asp Pro Lys Asn Pro Arg Ile Ile Gly Asp Leu Lys
                325                 330                 335

Val His Leu Ile Phe Tyr Ile Pro Glu Phe Ser Pro Arg Gln Lys Asp
            340                 345                 350

Glu Leu Asn Gln Val Phe Ala Gln Ile Asn Asp Lys Thr Lys Ala Lys
        355                 360                 365


<210> SEQ ID NO 3
<211> LENGTH: 819
<212> TYPE: DNA
<213> ORGANISM: Artificial Sequence
<220> FEATURE:
<223> OTHER INFORMATION: Description of Artificial Sequence:Clone pAD633

<400> SEQUENCE: 3

atgataaaag tttccgatgt ttgctttagt tatacaaaca acatggacca gcttgtgctg     60

aaaaatatta atgttgtttt tgaaaaaggt aaatattatg caattctagg gcataatggt    120

tcaggaaaat caacgttttc taagattctt tcaggaattt ttaaacctca aaaaggtagt    180

attgaagttg atggagtttt actaaataag gaaaatttaa cgaaaattag gaaaaaaatt    240

ggtataattt ttcaaaaccc agataatcaa tttgttgggg caacggttga agatgacatc    300

gctttcagtt tggaaaacat taatgaggat ccaaaaaaaa tgagtcaaat aatcgcaaat    360

ttagctgcaa aagtgcaaat ggagtcatat ttagaccgtg agccacaatt tttatctggg    420

ggccaaaagc aaaaagtagc aattgcatca gttttagcac taaatcctga gattataatt    480
```

-continued

```
tttgatgaaa taacttcaat gcttgatccc agaggtaaat atgatgttgt taaaattctt    540

gatgatctaa gaaaagataa aacaaaaact ttaatttcaa tcacccacaa tatgaatgaa    600

gcaattttag ctgatgaaat tattgttttt gcaaatgggg gaattatcgc tcagggggat    660

ccaaaattaa ttttaaatga taaaaatatc atcgaaaaag cgaaaattga ctccccattt    720

atctataaaa tttccagcgc acttaaatta gttagtccaa cttatgacga aaatgaattg    780

ctagagcaac tatgaaaatt aaagcaaaaa acatcgtaa                           819
```

```
<210> SEQ ID NO 4
<211> LENGTH: 272
<212> TYPE: PRT
<213> ORGANISM: Artificial Sequence
<220> FEATURE:
<223> OTHER INFORMATION: Description of Artificial Sequence:Deduced
      protein sequence from clone pAD633

<400> SEQUENCE: 4

Met Ile Lys Val Ser Asp Val Cys Phe Ser Tyr Thr Asn Asn Met Asp
  1               5                  10                  15

Gln Leu Val Leu Lys Asn Ile Asn Val Val Phe Glu Lys Gly Lys Tyr
             20                  25                  30

Tyr Ala Ile Leu Gly His Asn Gly Ser Gly Lys Ser Thr Phe Ser Lys
         35                  40                  45

Ile Leu Ser Gly Ile Phe Lys Pro Gln Lys Gly Ser Ile Glu Val Asp
     50                  55                  60

Gly Val Leu Leu Asn Lys Glu Asn Leu Thr Lys Ile Arg Lys Lys Ile
 65                  70                  75                  80

Gly Ile Ile Phe Gln Asn Pro Asp Asn Gln Phe Val Gly Ala Thr Val
                 85                  90                  95

Glu Asp Asp Ile Ala Phe Ser Leu Glu Asn Ile Asn Glu Asp Pro Lys
            100                 105                 110

Lys Met Ser Gln Ile Ile Ala Asn Leu Ala Ala Lys Val Gln Met Glu
        115                 120                 125

Ser Tyr Leu Asp Arg Glu Pro Gln Phe Leu Ser Gly Gly Gln Lys Gln
    130                 135                 140

Lys Val Ala Ile Ala Ser Val Leu Ala Leu Asn Pro Glu Ile Ile Ile
145                 150                 155                 160

Phe Asp Glu Ile Thr Ser Met Leu Asp Pro Arg Gly Lys Tyr Asp Val
                165                 170                 175

Val Lys Ile Leu Asp Asp Leu Arg Lys Asp Lys Thr Lys Thr Leu Ile
            180                 185                 190

Ser Ile Thr His Asn Met Asn Glu Ala Ile Leu Ala Asp Glu Ile Ile
        195                 200                 205

Val Phe Ala Asn Gly Gly Ile Ile Ala Gln Gly Asp Pro Lys Leu Ile
    210                 215                 220

Leu Asn Asp Lys Asn Ile Ile Glu Lys Ala Lys Ile Asp Ser Pro Phe
225                 230                 235                 240

Ile Tyr Lys Ile Ser Ser Ala Leu Lys Leu Val Ser Pro Thr Tyr Asp
                245                 250                 255

Glu Asn Glu Leu Leu Glu Gln Leu Trp Lys Leu Lys Gln Lys Thr Ser
            260                 265                 270
```

```
<210> SEQ ID NO 5
<211> LENGTH: 609
<212> TYPE: DNA
<213> ORGANISM: Artificial Sequence
```

-continued

<220> FEATURE:
<223> OTHER INFORMATION: Description of Artificial Sequence:Clone pAD639

<400> SEQUENCE: 5

```
atgtttagtc aaactattta taaatgaaaa agcgaaaatc tcgaaagagt ggtcgtccct     60

gaaaaaggac tttcttgcga atataacggt ctttttagca taagaactgg caaaagtttg    120

tacgggctgc tacaaaattt agataatgat tattttattg cttacctaag atcaagtgtg    180

cttatcttta cctcttccgc atcatccgct ttagtaagag caaagtctta ttgcgaaaac    240

gatttttgat tgcataaaaa taattttta gtcggcctta tcgtctttag tgccggaatt     300

tttaaaataa tggatggtag atgagaaaat acctatcttg ttaaatcagg ggatggtttt    360

aaccggtttt tacaagaact aaaaagcaaa aaacactata aattagaatg ttttttgctt    420

tcaaacttat tttttgtcag cctgagtcta actaatcata tcagaagtct agcccatcca    480

gatttaaata attcaactat ttatttaaat gaattatgcc ttgatgatct tagtcaaaaa    540

gaaactttag ctctaaaaag tcttggaaat tatgattttg acgatcaaga aaaggaactt    600

ttagagatc                                                            609
```

<210> SEQ ID NO 6
<211> LENGTH: 203
<212> TYPE: PRT
<213> ORGANISM: Artificial Sequence
<220> FEATURE:
<223> OTHER INFORMATION: Description of Artificial Sequence:Deduced protein sequence from clone pAD639

<400> SEQUENCE: 6

```
Met Phe Ser Gln Thr Ile Tyr Lys Trp Lys Ser Glu Asn Leu Glu Arg
  1               5                  10                  15

Val Val Val Pro Glu Lys Gly Leu Ser Cys Glu Tyr Asn Gly Leu Phe
             20                  25                  30

Ser Ile Arg Thr Gly Lys Ser Leu Tyr Gly Leu Leu Gln Asn Leu Asp
         35                  40                  45

Asn Asp Tyr Phe Ile Ala Tyr Leu Arg Ser Ser Val Leu Ile Phe Thr
     50                  55                  60

Ser Ser Ala Ser Ser Ala Leu Val Arg Ala Lys Ser Tyr Cys Glu Asn
 65                  70                  75                  80

Asp Phe Trp Leu His Lys Asn Asn Phe Leu Val Gly Leu Ile Val Phe
                 85                  90                  95

Ser Ala Gly Ile Phe Lys Ile Met Asp Gly Arg Trp Glu Asn Thr Tyr
            100                 105                 110

Leu Val Lys Ser Gly Asp Gly Phe Asn Arg Phe Leu Gln Glu Leu Lys
        115                 120                 125

Ser Lys Lys His Tyr Lys Leu Glu Cys Phe Leu Leu Ser Asn Leu Phe
    130                 135                 140

Phe Val Ser Leu Ser Leu Thr Asn His Ile Arg Ser Leu Ala His Pro
145                 150                 155                 160

Asp Leu Asn Asn Ser Thr Ile Tyr Leu Asn Glu Leu Cys Leu Asp Asp
                165                 170                 175

Leu Ser Gln Lys Glu Thr Leu Ala Leu Lys Ser Leu Gly Asn Tyr Asp
            180                 185                 190

Phe Asp Asp Gln Glu Lys Glu Leu Leu Glu Ile
        195                 200
```

<210> SEQ ID NO 7

-continued

```
<211> LENGTH: 471
<212> TYPE: DNA
<213> ORGANISM: Artificial Sequence
<220> FEATURE:
<223> OTHER INFORMATION: Description of Artificial Sequence:Clone pAD640

<400> SEQUENCE: 7

gaggtaagca cgattcccgg acgaggcgat attaaactaa caggttcgct taaggatgta      60

atgcaagaat cagcccggat tgccctttct tatgttcagt caaaggccaa ggattttggg     120

attaattttg attttgaaaa cactttaatt catattcatg tacccgaagg agcaattcca     180

aaagatgggc catcagcagg gataactttt gcaacagcaa taatttcagc cctctcgcaa     240

aagccggtct cacataatat tgcaatgaca ggggagataa ccttgcgcgg gaaggtttta     300

gcaatcggcg gactaaaaga aaagacgatg gggcctatt taaatgggat taaaattatt     360

tttattccca aggcgaacga gaaaaattta gtcgatattc cgcaggaagt aaaagacgtt     420

atccagttta ttcccgttga tacttatcaa ccaatttatg attttatttt t              471


<210> SEQ ID NO 8
<211> LENGTH: 157
<212> TYPE: PRT
<213> ORGANISM: Artificial Sequence
<220> FEATURE:
<223> OTHER INFORMATION: Description of Artificial Sequence:Deduced
      protein sequence from clone pAD640

<400> SEQUENCE: 8

Glu Val Ser Thr Ile Pro Gly Arg Gly Asp Ile Lys Leu Thr Gly Ser
  1               5                  10                  15

Leu Lys Asp Val Met Gln Glu Ser Ala Arg Ile Ala Leu Ser Tyr Val
             20                  25                  30

Gln Ser Lys Ala Lys Asp Phe Gly Ile Asn Phe Asp Phe Glu Asn Thr
         35                  40                  45

Leu Ile His Ile His Val Pro Glu Gly Ala Ile Pro Lys Asp Gly Pro
     50                  55                  60

Ser Ala Gly Ile Thr Phe Ala Thr Ala Ile Ile Ser Ala Leu Ser Gln
 65                  70                  75                  80

Lys Pro Val Ser His Asn Ile Ala Met Thr Gly Glu Ile Thr Leu Arg
                 85                  90                  95

Gly Lys Val Leu Ala Ile Gly Gly Leu Lys Glu Lys Thr Met Gly Ala
            100                 105                 110

Tyr Leu Asn Gly Ile Lys Ile Ile Phe Ile Pro Lys Ala Asn Glu Lys
        115                 120                 125

Asn Leu Val Asp Ile Pro Gln Glu Val Lys Asp Val Ile Gln Phe Ile
    130                 135                 140

Pro Val Asp Thr Tyr Gln Pro Ile Tyr Asp Phe Ile Phe
145                 150                 155


<210> SEQ ID NO 9
<211> LENGTH: 1128
<212> TYPE: DNA
<213> ORGANISM: Artificial Sequence
<220> FEATURE:
<223> OTHER INFORMATION: Description of Artificial Sequence:Clones
      pAD641 and pAD1033

<400> SEQUENCE: 9

aaaaaacttt tagatacttt aggggctgaa tttagtccaa aagcacttgt ttcttcgctt      60

tcgatctcac aaaagcaatt tatcgaaatc gccaaagctt tatcccaaaa accggaaatt     120
```

-continued

```
atcatttttg atgaaccgac ttcggttcta accgaaaaag atacccaaaa actttatctg    180

cttgttgaaa aacttaaaaa acaaggaatt gcaatcgtct gaattaccca tagaatggaa    240

gaaattaaga aaacttgtga atttatcact gtgattcgaa acggaatgta tattgaaagt    300

aagccaataa atgaatttaa aaacgaagat gagattattt ctttaatggt cggttttgat    360

atcgagcagc gctatcccga aaaaacgccg gttagaagta aaaaaccatc gtttttagtt    420

agaaatttat caaatgataa agtttctaat atcagttttg aaatcaaacc aggtgaaatt    480

ttagtttttt atggccttgt aagttcaggt cgaactgaat tagctagaac tttaattggc    540

gatatgcctt atttaaatgg tcatattgaa ctaaatggtc aagaatttcg cccaaaaaat    600

attaaggaca gtcttgatca tggaatttat tatctttctg aaaataggaa acaaattggt    660

ctaaatgtta atttaccaat taattttaat atcacaattt cttctcttgg ctcaaatcag    720

atttttctt tccttccttt tgtctcaaaa gcaaaaataa ctaaaactac aaatcattat    780

attaaacaat taaagatcaa aacaacttca caagatacgc cattaacttc tttatcaggt    840

ggaaatcaac aaaaagtttc acttgcaaaa gggcttgcaa cccaaccgca agttttcatc    900

ctcgatgaac caactcgcgg agtcgatgtt ggcgcaagaa aggaaattta taatttaatt    960

caccaattaa aacaagaaaa taaaacaatt atgataattt cttcggatat gcaagaggtt   1020

atcggaatcg ctgatcgggt aattacaatg tatgaaggca gaattacaag tgaattagtt   1080

ggcccgcaaa ttaccgatca aaatataatg aaatattcac ttaattta                1128
```

<210> SEQ ID NO 10
<211> LENGTH: 376
<212> TYPE: PRT
<213> ORGANISM: Artificial Sequence
<220> FEATURE:
<223> OTHER INFORMATION: Description of Artificial Sequence:Deduced protein sequence from clones pAD641 and pAD1033

<400> SEQUENCE: 10

```
Lys Lys Leu Leu Asp Thr Leu Gly Ala Glu Phe Ser Pro Lys Ala Leu
  1               5                  10                  15

Val Ser Ser Leu Ser Ile Ser Gln Lys Gln Phe Ile Glu Ile Ala Lys
             20                  25                  30

Ala Leu Ser Gln Lys Pro Glu Ile Ile Ile Phe Asp Glu Pro Thr Ser
         35                  40                  45

Val Leu Thr Glu Lys Asp Thr Gln Lys Leu Tyr Leu Leu Val Glu Lys
     50                  55                  60

Leu Lys Lys Gln Gly Ile Ala Ile Val Trp Ile Thr His Arg Met Glu
 65                  70                  75                  80

Glu Ile Lys Lys Thr Cys Glu Phe Ile Thr Val Ile Arg Asn Gly Met
                 85                  90                  95

Tyr Ile Glu Ser Lys Pro Ile Asn Glu Phe Lys Asn Glu Asp Glu Ile
            100                 105                 110

Ile Ser Leu Met Val Gly Phe Asp Ile Glu Gln Arg Tyr Pro Glu Lys
        115                 120                 125

Thr Pro Val Arg Ser Lys Lys Pro Ser Phe Leu Val Arg Asn Leu Ser
    130                 135                 140

Asn Asp Lys Val Ser Asn Ile Ser Phe Glu Ile Lys Pro Gly Glu Ile
145                 150                 155                 160

Leu Val Phe Tyr Gly Leu Val Ser Ser Gly Arg Thr Glu Leu Ala Arg
                165                 170                 175
```

-continued

```
Thr Leu Ile Gly Asp Met Pro Tyr Leu Asn Gly His Ile Glu Leu Asn
            180                 185                 190

Gly Gln Glu Phe Arg Pro Lys Asn Ile Lys Asp Ser Leu Asp His Gly
        195                 200                 205

Ile Tyr Tyr Leu Ser Glu Asn Arg Lys Gln Ile Gly Leu Asn Val Asn
    210                 215                 220

Leu Pro Ile Asn Phe Asn Ile Thr Ile Ser Ser Leu Gly Ser Asn Gln
225                 230                 235                 240

Ile Phe Ser Phe Leu Pro Phe Val Ser Lys Ala Lys Ile Thr Lys Thr
                245                 250                 255

Thr Asn His Tyr Ile Lys Gln Leu Lys Ile Lys Thr Thr Ser Gln Asp
            260                 265                 270

Thr Pro Leu Thr Ser Leu Ser Gly Gly Asn Gln Gln Lys Val Ser Leu
        275                 280                 285

Ala Lys Gly Leu Ala Thr Gln Pro Gln Val Phe Ile Leu Asp Glu Pro
    290                 295                 300

Thr Arg Gly Val Asp Val Gly Ala Arg Lys Glu Ile Tyr Asn Leu Ile
305                 310                 315                 320

His Gln Leu Lys Gln Glu Asn Lys Thr Ile Met Ile Ile Ser Ser Asp
                325                 330                 335

Met Gln Glu Val Ile Gly Ile Ala Asp Arg Val Ile Thr Met Tyr Glu
            340                 345                 350

Gly Arg Ile Thr Ser Glu Leu Val Gly Pro Gln Ile Thr Asp Gln Asn
        355                 360                 365

Ile Met Lys Tyr Ser Leu Asn Leu
    370                 375
```

<210> SEQ ID NO 11
<211> LENGTH: 2394
<212> TYPE: DNA
<213> ORGANISM: Artificial Sequence
<220> FEATURE:
<223> OTHER INFORMATION: Description of Artificial Sequence:Deduced protein sequence from clone pAD653

<400> SEQUENCE: 11

```
acagtcggaa ttaacaaaac cgaaatggat gcaaatacca aaagaatgat gtataatgcc      60

gatattactt attcggttca ttctgaatta ggttttgatt atctccggga taatatggtt     120

ttttcagcag ctgaaaaagt tcaaagggga ctaaattttt gcctaatcga tgaagtagac     180

tcaattttga tcgatgaagc caaaacccct ttgattatca gtggtggcaa aactaacctt     240

ccagcccaat atttatccgc gaaccaattt gttaatactc taattgctga agatttttat     300

attgatgaag aaactaaggg aattaaatta aatgataaag gaatcgataa ggcaaatgct     360

ttttttggcc ttcgtaattt atatgaaatt caaaactcag aaatagttca tcgaattcaa     420

aacgcgctga gagccaataa ggtgatgaaa cgcgatgttg aatatattgt ccaggacggc     480

aaaattgcct tagttgatca atttactggg cgaattatgg ctggaagatc ttattctgaa     540

ggtctccagc aagccctgca agcaaaagag ggcttgaaa ttgaacctga gacaaaaaca     600

ctagcaacaa ttacctatca aaattttttt cgcctttta aaaaattatc agggatgacc     660

gggactgcca aaaccgaaga acaagaattt atcgatgttt ataatatgcg cgtgaatgtg     720

attccgacaa acaaaccgat gattcgtaag gatgaaaaag atgaaatttt tgccactagt     780

cacgaaaaaa atcaagctat aatttccgaa gttgaacgtg ttcataaaat ggggcagcca     840

attttaattg gaacctcaca agttgttgac tctgaaacgc tttcggagat gctaaaccaa     900
```

-continued

```
aaaggacttt atcatacagt attaaatgca aaacaaaacc aacttgaagc cgaaattatt    960

gcccaggcag gacgaaaaaa tgcgattacc atcgcgacaa atatggctgg aagaagaact   1020

gatataattt tagagcctgg tgtgactgaa cttgggcggc tttatattct tggaaccgat   1080

aaagccgaaa ctagaagaat cgataaccaa ctacgaggtc gctctggacg acaaggtgat   1140

gtgggaattt cgcgattttt tatctcactt caggaccaac tttttcggcg ttttaccaat   1200

tttgatcaaa tttttggcgc ttatggacaa acaaatgggg caattaaagg aaaatatatt   1260

catgcggttt tacttgcagc ccaaaagaaa atcgaaggct ttaacttcga tatgcgcaaa   1320

actgtgctta gttatgatga tgttattcgt caacagcgtg atttaattta tgcccaaaga   1380

gatattttgc ttcagattga aaattttgac cattatatcc agaagatgat tattcgggct   1440

gttgatatca ttttaagcta tgattttata attttaccaa atcaagaaat tcactataaa   1500

aatttaataa attttcttaa tgataattta tcaagaatta ctcattttaa ctttgggcaa   1560

attggaattg aaaattatcc cattgaacaa cttaatgaat tttaatcaa acaattagaa    1620

actatttatt ttaaacaaat ccaatcagtt ttaaaggaaa atcttggaaa aacctacttt   1680

gaatcagaac gttatattat tttatcaaca cttgatagtc agtgacaaaa tcatattgac   1740

accattgaca aattaagatc ttctgctaat ttagttcagt attcccagaa aaatccttat   1800

caaattttta ccgaggaagc aacaaaaaaa ttcaacattt tagtagcaga atccgcttat   1860

caggcaatag tttctttatt taataattca aatgctgaaa aaatagaata tatcaaagca   1920

attttgtctg atggaaccgc aatttcttat ccggcagata gccctcaaga aataattgat   1980

caaataatcg cctctaacga ggagagaatc gcggctgcaa gaaaagcaaa agaagaaaaa   2040

cagcctgaat ttattgaaaa acaacttgct aaactaaaaa ttgaaaaggt tgaatcagga   2100

gaggaatttg aactttgaaa aatcggagat agcaaactag ttaacctaaa aaaggaaatg   2160

cctcttgatg aaaaacaaaa tattttagta aaaatgcagc aggaacaact tgaaatgatg   2220

agcgaggaag aaaaaaacct aatacaagaa caaaatttag agattgtaga gattgaagaa   2280

atagaggaag aaattcaaaa tgaaaatccc caaaaagttg aatttgtgga ttttaaaaat   2340

gatcctgatg catataataa actgatattc ggtgcggatt atgcagataa ccat         2394
```

```
<210> SEQ ID NO 12
<211> LENGTH: 798
<212> TYPE: PRT
<213> ORGANISM: Artificial Sequence
<220> FEATURE:
<223> OTHER INFORMATION: Description of Artificial Sequence:Deduced
      protein sequence from clone pAD653

<400> SEQUENCE: 12

Thr Val Gly Ile Asn Lys Thr Glu Met Asp Ala Asn Thr Lys Arg Met
  1               5                  10                  15

Met Tyr Asn Ala Asp Ile Thr Tyr Ser Val His Ser Glu Leu Gly Phe
             20                  25                  30

Asp Tyr Leu Arg Asp Asn Met Val Phe Ser Ala Ala Glu Lys Val Gln
         35                  40                  45

Arg Gly Leu Asn Phe Cys Leu Ile Asp Glu Val Asp Ser Ile Leu Ile
     50                  55                  60

Asp Glu Ala Lys Thr Pro Leu Ile Ile Ser Gly Gly Lys Thr Asn Leu
 65                  70                  75                  80

Pro Ala Gln Tyr Leu Ser Ala Asn Gln Phe Val Asn Thr Leu Ile Ala
                 85                  90                  95
```

-continued

```
Glu Asp Phe Tyr Ile Asp Glu Glu Thr Lys Gly Ile Lys Leu Asn Asp
            100                 105                 110

Lys Gly Ile Asp Lys Ala Asn Ala Phe Phe Gly Leu Arg Asn Leu Tyr
        115                 120                 125

Glu Ile Gln Asn Ser Glu Ile Val His Arg Ile Gln Asn Ala Leu Arg
    130                 135                 140

Ala Asn Lys Val Met Lys Arg Asp Val Glu Tyr Ile Val Gln Asp Gly
145                 150                 155                 160

Lys Ile Ala Leu Val Asp Gln Phe Thr Gly Arg Ile Met Ala Gly Arg
                165                 170                 175

Ser Tyr Ser Glu Gly Leu Gln Gln Ala Leu Gln Ala Lys Glu Gly Leu
            180                 185                 190

Glu Ile Glu Pro Glu Thr Lys Thr Leu Ala Thr Ile Thr Tyr Gln Asn
        195                 200                 205

Phe Phe Arg Leu Phe Lys Lys Leu Ser Gly Met Thr Gly Thr Ala Lys
    210                 215                 220

Thr Glu Glu Gln Glu Phe Ile Asp Val Tyr Asn Met Arg Val Asn Val
225                 230                 235                 240

Ile Pro Thr Asn Lys Pro Met Ile Arg Lys Asp Glu Lys Asp Glu Ile
                245                 250                 255

Phe Ala Thr Ser His Glu Lys Asn Gln Ala Ile Ile Ser Glu Val Glu
            260                 265                 270

Arg Val His Lys Met Gly Gln Pro Ile Leu Ile Gly Thr Ser Gln Val
        275                 280                 285

Val Asp Ser Glu Thr Leu Ser Glu Met Leu Asn Gln Lys Gly Leu Tyr
    290                 295                 300

His Thr Val Leu Asn Ala Lys Gln Asn Gln Leu Glu Ala Glu Ile Ile
305                 310                 315                 320

Ala Gln Ala Gly Arg Lys Asn Ala Ile Thr Ile Ala Thr Asn Met Ala
                325                 330                 335

Gly Arg Arg Thr Asp Ile Ile Leu Glu Pro Gly Val Thr Glu Leu Gly
            340                 345                 350

Arg Leu Tyr Ile Leu Gly Thr Asp Lys Ala Glu Thr Arg Arg Ile Asp
        355                 360                 365

Asn Gln Leu Arg Gly Arg Ser Gly Arg Gln Gly Asp Val Gly Ile Ser
    370                 375                 380

Arg Phe Phe Ile Ser Leu Gln Asp Gln Leu Phe Arg Arg Phe Thr Asn
385                 390                 395                 400

Phe Asp Gln Ile Phe Gly Ala Tyr Gly Gln Thr Asn Gly Ala Ile Lys
                405                 410                 415

Gly Lys Tyr Ile His Ala Val Leu Leu Ala Ala Gln Lys Lys Ile Glu
            420                 425                 430

Gly Phe Asn Phe Asp Met Arg Lys Thr Val Leu Ser Tyr Asp Asp Val
        435                 440                 445

Ile Arg Gln Gln Arg Asp Leu Ile Tyr Ala Gln Arg Asp Ile Leu Leu
    450                 455                 460

Gln Ile Glu Asn Phe Asp His Tyr Ile Gln Lys Met Ile Ile Arg Ala
465                 470                 475                 480

Val Asp Ile Ile Leu Ser Tyr Asp Phe Ile Ile Leu Pro Asn Gln Glu
                485                 490                 495

Ile His Tyr Lys Asn Leu Ile Asn Phe Leu Asn Asp Asn Leu Ser Arg
            500                 505                 510
```

-continued

```
Ile Thr His Phe Asn Phe Gly Gln Ile Gly Ile Glu Asn Tyr Pro Ile
        515                 520                 525

Glu Gln Leu Asn Glu Phe Leu Ile Lys Gln Leu Glu Thr Ile Tyr Phe
    530                 535                 540

Lys Gln Ile Gln Ser Val Leu Lys Glu Asn Leu Gly Lys Thr Tyr Phe
545                 550                 555                 560

Glu Ser Glu Arg Tyr Ile Ile Leu Ser Thr Leu Asp Ser Gln Trp Gln
                565                 570                 575

Asn His Ile Asp Thr Ile Asp Lys Leu Arg Ser Ser Ala Asn Leu Val
            580                 585                 590

Gln Tyr Ser Gln Lys Asn Pro Tyr Gln Ile Phe Thr Glu Glu Ala Thr
        595                 600                 605

Lys Lys Phe Asn Ile Leu Val Ala Glu Ser Ala Tyr Gln Ala Ile Val
    610                 615                 620

Ser Leu Phe Asn Asn Ser Asn Ala Glu Lys Ile Glu Tyr Ile Lys Ala
625                 630                 635                 640

Ile Leu Ser Asp Gly Thr Ala Ile Ser Tyr Pro Ala Asp Ser Pro Gln
                645                 650                 655

Glu Ile Ile Asp Gln Ile Ile Ala Ser Asn Glu Glu Arg Ile Ala Ala
            660                 665                 670

Ala Arg Lys Ala Lys Glu Glu Lys Gln Pro Glu Phe Ile Glu Lys Gln
        675                 680                 685

Leu Ala Lys Leu Lys Ile Glu Lys Val Glu Ser Gly Glu Glu Phe Glu
    690                 695                 700

Leu Trp Lys Ile Gly Asp Ser Lys Leu Val Asn Leu Lys Lys Glu Met
705                 710                 715                 720

Pro Leu Asp Glu Lys Gln Asn Ile Leu Val Lys Met Gln Gln Glu Gln
                725                 730                 735

Leu Glu Met Met Ser Glu Glu Glu Lys Asn Leu Ile Gln Glu Gln Asn
            740                 745                 750

Leu Glu Ile Val Glu Ile Glu Glu Ile Glu Glu Glu Ile Gln Asn Glu
        755                 760                 765

Asn Pro Gln Lys Val Glu Phe Val Asp Phe Lys Asn Asp Pro Asp Ala
    770                 775                 780

Tyr Asn Lys Leu Ile Phe Gly Ala Asp Tyr Ala Asp Asn His
785                 790                 795
```

<210> SEQ ID NO 13
<211> LENGTH: 1410
<212> TYPE: DNA
<213> ORGANISM: Artificial Sequence
<220> FEATURE:
<223> OTHER INFORMATION: Description of Artificial Sequence:Clones pAD657 and pAD964

<400> SEQUENCE: 13

```
atgatttcgt atttttattc aaaatcagca ccgcagtgtc ttaaaactga aaatcccaga     60

ttttgttata aactaaataa aaatttagta aaatttcaaa aagaattaga tctattaaaa    120

cagaaaaaac ttgcaccaaa agaatatgaa agccagttta gtgatctaaa agaaaaattt    180

ttagcttatg aagttaatat aaaaaaacat tatcaggcaa aaaaatccta taaattacgt    240

gctatttgag atcggattca aaaatattga catacaagct ttaacagatc ccattttgat    300

tttgaagcat tttctaaaaa tgttgaatat aaacaaatag gaaataaacg tcataaaatt    360

gttgcccgga tcaaaaattt aaacctttcc tttgtcaatc cagcaaatcc cgagattaga    420
```

-continued

```
aatatcgtga ttcgtaatgc ctcaattgat ttttatgaag gcgaaattca tgccttaatt    480

ggcgagtctg gttcaggaaa atcagtaatt acttcttgtc tttatggtct tgtcggtcaa    540

aacggggtaa ttgaatcagg tgaaatcaaa ctttttaaca atccagtgca aaattttgat    600

tttcgtgctt gagaactttc aaattatcgg ggaaaagtta tttcagctgt cttccagaat    660

ccgatgtcaa ctttaaatcc aacaaaaaaa ataggcatcc aaattatgga aggaatgtta    720

ttaaacaaga ttgttaaaac gaaaaaagaa gcctatgaaa aagcactttt atatcttaga    780

atgaccaaaa ttgctaaccc ggaaatggtt atgaaattat atccccatga gctttcagga    840

ggtatgattc aaagaattgt gatctcagca attttatcac ttgaacctaa aattatcgtt    900

atggatgaac caacaacagc tttggataca accgtgcaag ctttagttct tgatattatc    960

cgcgatctcc aaaaaagact aaaaattaca attattttca ttactcacga ccttggagtt   1020

gtcgcttctc ttgcaactta tatctcaatc atgtatgctg gtcaagttgt cgaggaaggt   1080

acaagagatg aaattctttt aaatccaaga catccatata cttgagggct aattacttca   1140

atgcctgatg tcaataaagg cgaacgactt cagtcaattc gcggggttgt tccttcttct   1200

ttaaattcaa ttgttggcga tgcttttgca gttagaaacg attatgcctt agaacaagat   1260

ttttttattg aacctaaatt ttacagaata agtccaactc accgagtcaa atcagcttta   1320

cttgatccaa aagcaccaaa agttgtccca ccaaaaatta tttaccaaaa atgactgcaa   1380

tttgcaaaga tgaggcaaga aaatggaaga                                    1410
```

```
<210> SEQ ID NO 14
<211> LENGTH: 470
<212> TYPE: PRT
<213> ORGANISM: Artificial Sequence
<220> FEATURE:
<223> OTHER INFORMATION: Description of Artificial Sequence:Deduced
      protein sequence from clones pAD657 and pAD964

<400> SEQUENCE: 14

Met Ile Ser Tyr Phe Tyr Ser Lys Ser Ala Pro Gln Cys Leu Lys Thr
  1               5                  10                  15

Glu Asn Pro Arg Phe Cys Tyr Lys Leu Asn Lys Asn Leu Val Lys Phe
             20                  25                  30

Gln Lys Glu Leu Asp Leu Leu Lys Gln Lys Lys Leu Ala Pro Lys Glu
         35                  40                  45

Tyr Glu Ser Gln Phe Ser Asp Leu Lys Glu Lys Phe Leu Ala Tyr Glu
     50                  55                  60

Val Asn Ile Lys Lys His Tyr Gln Ala Lys Lys Ser Tyr Lys Leu Arg
 65                  70                  75                  80

Ala Ile Trp Asp Arg Ile Gln Lys Tyr Trp His Thr Ser Phe Asn Arg
                 85                  90                  95

Ser His Phe Asp Phe Glu Ala Phe Ser Lys Asn Val Glu Tyr Lys Gln
            100                 105                 110

Ile Gly Asn Lys Arg His Lys Ile Val Ala Arg Ile Lys Asn Leu Asn
        115                 120                 125

Leu Ser Phe Val Asn Pro Ala Asn Pro Glu Ile Arg Asn Ile Val Ile
    130                 135                 140

Arg Asn Ala Ser Ile Asp Phe Tyr Glu Gly Glu Ile His Ala Leu Ile
145                 150                 155                 160

Gly Glu Ser Gly Ser Gly Lys Ser Val Ile Thr Ser Cys Leu Tyr Gly
                165                 170                 175

Leu Val Gly Gln Asn Gly Val Ile Glu Ser Gly Glu Ile Lys Leu Phe
```

-continued

```
            180                 185                 190

Asn Asn Pro Val Gln Asn Phe Asp Phe Arg Ala Trp Glu Leu Ser Asn
        195                 200                 205

Tyr Arg Gly Lys Val Ile Ser Ala Val Phe Gln Asn Pro Met Ser Thr
    210                 215                 220

Leu Asn Pro Thr Lys Lys Ile Gly Ile Gln Ile Met Glu Gly Met Leu
225                 230                 235                 240

Leu Asn Lys Ile Val Lys Thr Lys Lys Glu Ala Tyr Glu Lys Ala Leu
                245                 250                 255

Leu Tyr Leu Arg Met Thr Lys Ile Ala Asn Pro Glu Met Val Met Lys
            260                 265                 270

Leu Tyr Pro His Glu Leu Ser Gly Gly Met Ile Gln Arg Ile Val Ile
        275                 280                 285

Ser Ala Ile Leu Ser Leu Glu Pro Lys Ile Ile Val Met Asp Glu Pro
    290                 295                 300

Thr Thr Ala Leu Asp Thr Thr Val Gln Ala Leu Val Leu Asp Ile Ile
305                 310                 315                 320

Arg Asp Leu Gln Lys Arg Leu Lys Ile Thr Ile Ile Phe Ile Thr His
                325                 330                 335

Asp Leu Gly Val Val Ala Ser Leu Ala Thr Tyr Ile Ser Ile Met Tyr
            340                 345                 350

Ala Gly Gln Val Val Glu Glu Gly Thr Arg Asp Glu Ile Leu Leu Asn
        355                 360                 365

Pro Arg His Pro Tyr Thr Trp Gly Leu Ile Thr Ser Met Pro Asp Val
    370                 375                 380

Asn Lys Gly Glu Arg Leu Gln Ser Ile Arg Gly Val Val Pro Ser Ser
385                 390                 395                 400

Leu Asn Ser Ile Val Gly Asp Ala Phe Ala Val Arg Asn Asp Tyr Ala
                405                 410                 415

Leu Glu Gln Asp Phe Phe Ile Glu Pro Lys Phe Tyr Arg Ile Ser Pro
            420                 425                 430

Thr His Arg Val Lys Ser Ala Leu Leu Asp Pro Lys Ala Pro Lys Val
        435                 440                 445

Val Pro Pro Lys Ile Ile Tyr Gln Lys Trp Leu Gln Phe Ala Lys Met
    450                 455                 460

Arg Gln Glu Asn Gly Arg
465                 470
```

<210> SEQ ID NO 15
<211> LENGTH: 1332
<212> TYPE: DNA
<213> ORGANISM: Artificial Sequence
<220> FEATURE:
<223> OTHER INFORMATION: Description of Artificial Sequence:Clones pAD659 and pAD910

<400> SEQUENCE: 15

```
atgaaaaata ttgaaaaaag tgaaataatt atctcccttg ttgatgttga taaagaattt     60

ggtgataaaa aagttttaga tcaaataaat ttggacatta aacgaggaga ttttgtcaca    120

cttttagggc cctcagggtc cgggaagaca acaattttac gtttaattgg tggttttgaa    180

tgaactactc gcggcgaaat caaatttaat ggcatcgata taaaagacgt tccggcacat    240

aaacgtgata cagctacaat ttttcaagat tatgcacttt ttccacattt atcagttcgt    300

ggaaatattg aatttggtct taaattaaaa agaattaaaa aaaaggcaga agaaattccg    360
```

-continued

```
gatgtagtct ggaaaaaatt tgagcactta aagaaaaaat gacaggataa gcaaaagcga    420

aagattaaag agttaaaaat tttacaggct catttagaaa aactgcttga aaatccacag    480

ttagatatta aaaaacgtaa aaaattacag gataaattag atgattctga ttttagatat    540

tcaaattgag aaaattatct aacatccaaa tcagaaagtt ttaaaaaaaa atacctaacc    600

cgaaagatca caaaacagga aattaataaa gaaattaccg atattattga ccttgttggt    660

ctaactggaa atgaaaatcg agcaatttcg gaattatcag gaggaatgaa acaacgcgta    720

gcacttgcaa gatcgcttgt aattgagcct gaaattgtcc tacttgatga acctttatca    780

gctttagata caaaaattag gcaaaaaatg caagtttttc taaaaaaaat tcaacaaaaa    840

cttggcctaa cttttatttt tgttactcat gatcaagatg aagccttgca attatcagat    900

aaaatcgcca taatccgtaa tggaaaaatc gcccaatacg atgaaccaaa acaaatttat    960

gactatccag ttaataaatg ggtggctaat tttattggtg attctaattt ttttcaggca   1020

aaatacatta aaaaaaatca ggtcgaaatt cttggtctta aattatatac aattcatgat   1080

gagtttatcc caggccaaaa attagattgc ctgattcgtc cagaagatat cgatattgac   1140

ctaaattcag gctattttaa aggaaaagtt atccaaaata tttataaagg ttcatactat   1200

tcacttgata tcaaagtaga aaatacaata attaatgtcg aaactaacga tttttatgac   1260

ctcgagactc aagtttttct aaaatgagat gatgatgcta ttcatttaat ggagatggaa   1320

aatgctgaaa tt                                                       1332
```

```
<210> SEQ ID NO 16
<211> LENGTH: 444
<212> TYPE: PRT
<213> ORGANISM: Artificial Sequence
<220> FEATURE:
<223> OTHER INFORMATION: Description of Artificial Sequence:Deduced
      protein sequence from clones pAD659 and pAD910

<400> SEQUENCE: 16

Met Lys Asn Ile Glu Lys Ser Glu Ile Ile Ile Ser Leu Val Asp Val
  1               5                  10                  15

Asp Lys Glu Phe Gly Asp Lys Lys Val Leu Asp Gln Ile Asn Leu Asp
             20                  25                  30

Ile Lys Arg Gly Asp Phe Val Thr Leu Leu Gly Pro Ser Gly Ser Gly
         35                  40                  45

Lys Thr Thr Ile Leu Arg Leu Ile Gly Gly Phe Glu Trp Thr Thr Arg
     50                  55                  60

Gly Glu Ile Lys Phe Asn Gly Ile Asp Ile Lys Asp Val Pro Ala His
 65                  70                  75                  80

Lys Arg Asp Thr Ala Thr Ile Phe Gln Asp Tyr Ala Leu Phe Pro His
                 85                  90                  95

Leu Ser Val Arg Gly Asn Ile Glu Phe Gly Leu Lys Leu Lys Arg Ile
            100                 105                 110

Lys Lys Lys Ala Glu Glu Ile Pro Asp Val Val Trp Lys Lys Phe Glu
        115                 120                 125

His Leu Lys Lys Lys Trp Gln Asp Lys Gln Lys Arg Lys Ile Lys Glu
    130                 135                 140

Leu Lys Ile Leu Gln Ala His Leu Glu Lys Leu Leu Glu Asn Pro Gln
145                 150                 155                 160

Leu Asp Ile Lys Lys Arg Lys Lys Leu Gln Asp Lys Leu Asp Asp Ser
                165                 170                 175

Asp Phe Arg Tyr Ser Asn Trp Glu Asn Tyr Leu Thr Ser Lys Ser Glu
```

-continued

```
            180                 185                 190

Ser Phe Lys Lys Lys Tyr Leu Thr Arg Lys Ile Thr Lys Gln Glu Ile
        195                 200                 205

Asn Lys Glu Ile Thr Asp Ile Ile Asp Leu Val Gly Leu Thr Gly Asn
    210                 215                 220

Glu Asn Arg Ala Ile Ser Glu Leu Ser Gly Gly Met Lys Gln Arg Val
225                 230                 235                 240

Ala Leu Ala Arg Ser Leu Val Ile Glu Pro Glu Ile Val Leu Leu Asp
                245                 250                 255

Glu Pro Leu Ser Ala Leu Asp Thr Lys Ile Arg Gln Lys Met Gln Val
            260                 265                 270

Phe Leu Lys Lys Ile Gln Gln Lys Leu Gly Leu Thr Phe Ile Phe Val
        275                 280                 285

Thr His Asp Gln Asp Glu Ala Leu Gln Leu Ser Asp Lys Ile Ala Ile
    290                 295                 300

Ile Arg Asn Gly Lys Ile Ala Gln Tyr Asp Glu Pro Lys Gln Ile Tyr
305                 310                 315                 320

Asp Tyr Pro Val Asn Lys Trp Val Ala Asn Phe Ile Gly Asp Ser Asn
                325                 330                 335

Phe Phe Gln Ala Lys Tyr Ile Lys Lys Asn Gln Val Glu Ile Leu Gly
            340                 345                 350

Leu Lys Leu Tyr Thr Ile His Asp Glu Phe Ile Pro Gly Gln Lys Leu
        355                 360                 365

Asp Cys Leu Ile Arg Pro Glu Asp Ile Asp Ile Asp Leu Asn Ser Gly
    370                 375                 380

Tyr Phe Lys Gly Lys Val Ile Gln Asn Ile Tyr Lys Gly Ser Tyr Tyr
385                 390                 395                 400

Ser Leu Asp Ile Lys Val Glu Asn Thr Ile Ile Asn Val Glu Thr Asn
                405                 410                 415

Asp Phe Tyr Asp Leu Glu Thr Gln Val Phe Leu Lys Trp Asp Asp Asp
            420                 425                 430

Ala Ile His Leu Met Glu Met Glu Asn Ala Glu Ile
        435                 440


<210> SEQ ID NO 17
<211> LENGTH: 1590
<212> TYPE: DNA
<213> ORGANISM: Artificial Sequence
<220> FEATURE:
<223> OTHER INFORMATION: Description of Artificial Sequence:Deduced
      protein sequence from pAD662

<400> SEQUENCE: 17

gatattaaat tgaaaaaaac taatattcta tcactaaaaa aaataaaaaa agtttatggt     60

cctgtaattg ctctttctga tgtgactttt gttgttccaa aaggggaaat aactagccta    120

gttggtgaaa atggcgcggg aaaatcgaca cttttaaaaa ttttatcagg agtgattcct    180

gctggacaat atgaaggtga tctaattttt gaagataaaa ttatggcttt tgcaaataca    240

aaagcctccg aacgtgtcgg aattgcaata attcatcaag aactttcaat ttcaccttat    300

ttatcaattt gcgagaacat gtatatcggt aattatccga ctaaatttgg caaagttaac    360

tgaaataaga tgatttccga atgcaaaaaa tatctagaaa tggtcggtct tgatgaagat    420

ccaacaacaa ttgctggctc tctttcgatt gcaaaacagc aaatggttga gatcgcaaaa    480

gcactttcaa aaaatgcaaa actactaatt ttagatgaac cgacttcctc tttaaatgat    540
```

-continued

```
gaaaatgctt ttcgcttact tgatattatg aaaagtttaa aaagtaaagg aattacttcg    600

atttttgtct cccataaatt aaatgaagtc aaatatgtct ctgataatat tgttgtaatc    660

cgcgatggta aattcatttc ccagtataat aaaaatgaag aaataattga tgaaaaccgg    720

ctaattcagg acattgttgg ccggccttta aagtccaaat ttcctcctag ggatttagat    780

cgaaaaatcg ggaaattat ttttgagatc aaagatatag ttattcctca tgctagtatt    840

gcaaattata atgttgtcaa aaatgcttcc cttgatgtta aacaaggcga aattgtcgga    900

atttccggac ttgttggatc gggtcgaacc gaattaatgc tttcactttt tgggcagtat    960

tataacaaac cttcaagtgg caaagttttc tataaaggta aagaagtaaa atttactaac   1020

acaaaacagg caatcaaatc gggaattatg tatgcttccg aagatcgaaa aaatgttggt   1080

ctaatccaaa ttttttcgat tcaaaataat atcacttccg ccgctttgca tttattttca   1140

aaatgaggaa ttctaaataa aaataaggaa ataattaatg cccaaaaact aaaaaaagat   1200

gtaagtatta aaacaaaaaa tattctaaat aatgtcgaat ccctttctgg gggaaatcag   1260

caaaaagttg taattgccaa agctttaagc accaaatttg accttctaat tatcgatgag   1320

ccaacaaaag gtattgatgt tggctcaaaa tacgaaattt ataaaatttt actagacctt   1380

tcatcacaag gtaaaacaat tattgtaatc tcttcggaaa ttgaagaact tttaggaatc   1440

accgatcacc tttattttgt gactggaaaa ctttttggtc aaaatcaaga ctgactttcc   1500

cagtttttgc atctttttta taactttttt gaccaaaagg attaccataa ggacttccaa   1560

attttgagac ataatcttgg tgaagcgagt                                    1590
```

```
<210> SEQ ID NO 18
<211> LENGTH: 530
<212> TYPE: PRT
<213> ORGANISM: Artificial Sequence
<220> FEATURE:
<223> OTHER INFORMATION: Description of Artificial Sequence:Deduced
      protein sequence from clone pAD662

<400> SEQUENCE: 18

Asp Ile Lys Leu Lys Lys Thr Asn Ile Leu Ser Leu Lys Lys Ile Lys
  1               5                  10                  15

Lys Val Tyr Gly Pro Val Ile Ala Leu Ser Asp Val Thr Phe Val Val
             20                  25                  30

Pro Lys Gly Glu Ile Thr Ser Leu Val Gly Glu Asn Gly Ala Gly Lys
         35                  40                  45

Ser Thr Leu Leu Lys Ile Leu Ser Gly Val Ile Pro Ala Gly Gln Tyr
     50                  55                  60

Glu Gly Asp Leu Ile Phe Glu Asp Lys Ile Met Ala Phe Ala Asn Thr
 65                  70                  75                  80

Lys Ala Ser Glu Arg Val Gly Ile Ala Ile Ile His Gln Glu Leu Ser
                 85                  90                  95

Ile Ser Pro Tyr Leu Ser Ile Cys Glu Asn Met Tyr Ile Gly Asn Tyr
            100                 105                 110

Pro Thr Lys Phe Gly Lys Val Asn Trp Asn Lys Met Ile Ser Glu Cys
        115                 120                 125

Lys Lys Tyr Leu Glu Met Val Gly Leu Asp Glu Asp Pro Thr Thr Ile
    130                 135                 140

Ala Gly Ser Leu Ser Ile Ala Lys Gln Gln Met Val Glu Ile Ala Lys
145                 150                 155                 160

Ala Leu Ser Lys Asn Ala Lys Leu Leu Ile Leu Asp Glu Pro Thr Ser
                165                 170                 175
```

```
Ser Leu Asn Asp Glu Asn Ala Phe Arg Leu Leu Asp Ile Met Lys Ser
            180                 185                 190

Leu Lys Ser Lys Gly Ile Thr Ser Ile Phe Val Ser His Lys Leu Asn
        195                 200                 205

Glu Val Lys Tyr Val Ser Asp Asn Ile Val Val Ile Arg Asp Gly Lys
    210                 215                 220

Phe Ile Ser Gln Tyr Asn Lys Asn Glu Glu Ile Ile Asp Glu Asn Arg
225                 230                 235                 240

Leu Ile Gln Asp Ile Val Gly Arg Pro Leu Lys Ser Lys Phe Pro Pro
                245                 250                 255

Arg Asp Leu Asp Arg Lys Ile Gly Glu Ile Ile Phe Glu Ile Lys Asp
            260                 265                 270

Ile Val Ile Pro His Ala Ser Ile Ala Asn Tyr Asn Val Val Lys Asn
        275                 280                 285

Ala Ser Leu Asp Val Lys Gln Gly Glu Ile Val Gly Ile Ser Gly Leu
    290                 295                 300

Val Gly Ser Gly Arg Thr Glu Leu Met Leu Ser Leu Phe Gly Gln Tyr
305                 310                 315                 320

Tyr Asn Lys Pro Ser Ser Gly Lys Val Phe Tyr Lys Gly Lys Glu Val
                325                 330                 335

Lys Phe Thr Asn Thr Lys Gln Ala Ile Lys Ser Gly Ile Met Tyr Ala
            340                 345                 350

Ser Glu Asp Arg Lys Asn Val Gly Leu Ile Gln Ile Phe Ser Ile Gln
        355                 360                 365

Asn Asn Ile Thr Ser Ala Ala Leu His Leu Phe Ser Lys Trp Gly Ile
    370                 375                 380

Leu Asn Lys Asn Lys Glu Ile Ile Asn Ala Gln Lys Leu Lys Lys Asp
385                 390                 395                 400

Val Ser Ile Lys Thr Lys Asn Ile Leu Asn Asn Val Glu Ser Leu Ser
                405                 410                 415

Gly Gly Asn Gln Gln Lys Val Val Ile Ala Lys Ala Leu Ser Thr Lys
            420                 425                 430

Phe Asp Leu Leu Ile Ile Asp Glu Pro Thr Lys Gly Ile Asp Val Gly
        435                 440                 445

Ser Lys Tyr Glu Ile Tyr Lys Ile Leu Leu Asp Leu Ser Ser Gln Gly
    450                 455                 460

Lys Thr Ile Ile Val Ile Ser Ser Glu Ile Glu Glu Leu Leu Gly Ile
465                 470                 475                 480

Thr Asp His Leu Tyr Phe Val Thr Gly Lys Leu Phe Gly Gln Asn Gln
                485                 490                 495

Asp Trp Leu Ser Gln Phe Leu His Leu Phe Tyr Asn Phe Phe Asp Gln
            500                 505                 510

Lys Asp Tyr His Lys Asp Phe Gln Ile Leu Arg His Asn Leu Gly Glu
        515                 520                 525

Ala Ser
    530
```

<210> SEQ ID NO 19
<211> LENGTH: 852
<212> TYPE: DNA
<213> ORGANISM: Artificial Sequence
<220> FEATURE:
<223> OTHER INFORMATION: Description of Artificial Sequence:Clone pAD681

<400> SEQUENCE: 19

-continued

```
atcgaaacca tcaaaattga gctgggtgag cagctcgaat tttttgaaaa aaataataaa     60

ttagtcgaaa aacaacgact aaaagaccga gtcaataatg atattgactc gctttctgaa    120

ttcggaattt gttcaggaat tgagaattat gcccgccata ttgacggacg ccaaaaaggc    180

gaaaaaccat ttagtttact agattattta ccccaagacg gcctaatttt tattgatgaa    240

tcccatatta tgatcagcca aattaagggc atgtatgaag gtgatcgaag ccgaaaacaa    300

accttggttg actatggtta tcgactacct tcagctcttg ataatcggcc cttaaaactc    360

agtgaatttg agaaatatca acaggcaaaa atttatgttt cagccacacc ggccagctat    420

gaaattgata aaacaaatgg cgaaattgtc tcgcaaatta tcagaccaac tggactaatt    480

gatccagaaa tagtaattga atctaccaaa aatcaaatgg agaaaatttt tcagtatttg    540

ctaaaacaga aggaaaaaaa agaaagaagt ctcattttaa ctaccacaaa acgactggcc    600

gaagaaatca gcaagtatct ccaggaagaa aaattacaaa atgtctatta tttgcactca    660

gaaatgacga cttttgagcg cgatgaaatc ataattaagc ttcgaaaagg aatttatgat    720

gcaattgtcg ggataaattt acttcgtgaa ggcgttgata tcccggaagt ttctttgatt    780

tttgttcttg aagccggtct tgtttctttt ttgcgatccg catgcgagct cggtaccccg    840

ggtcgacctg ca                                                         852
```

```
<210> SEQ ID NO 20
<211> LENGTH: 284
<212> TYPE: PRT
<213> ORGANISM: Artificial Sequence
<220> FEATURE:
<223> OTHER INFORMATION: Description of Artificial Sequence:Deduced
      protein sequence from clone pAD681

<400> SEQUENCE: 20

Ile Glu Thr Ile Lys Ile Glu Leu Gly Glu Gln Leu Glu Phe Phe Glu
  1               5                  10                  15

Lys Asn Asn Lys Leu Val Glu Lys Gln Arg Leu Lys Asp Arg Val Asn
             20                  25                  30

Asn Asp Ile Asp Ser Leu Ser Glu Phe Gly Ile Cys Ser Gly Ile Glu
         35                  40                  45

Asn Tyr Ala Arg His Ile Asp Gly Arg Gln Lys Gly Glu Lys Pro Phe
     50                  55                  60

Ser Leu Leu Asp Tyr Leu Pro Gln Asp Gly Leu Ile Phe Ile Asp Glu
 65                  70                  75                  80

Ser His Ile Met Ile Ser Gln Ile Lys Gly Met Tyr Glu Gly Asp Arg
                 85                  90                  95

Ser Arg Lys Gln Thr Leu Val Asp Tyr Gly Tyr Arg Leu Pro Ser Ala
            100                 105                 110

Leu Asp Asn Arg Pro Leu Lys Leu Ser Glu Phe Glu Lys Tyr Gln Gln
        115                 120                 125

Ala Lys Ile Tyr Val Ser Ala Thr Pro Ala Ser Tyr Glu Ile Asp Lys
    130                 135                 140

Thr Asn Gly Glu Ile Val Ser Gln Ile Ile Arg Pro Thr Gly Leu Ile
145                 150                 155                 160

Asp Pro Glu Ile Val Ile Glu Ser Thr Lys Asn Gln Met Glu Lys Ile
                165                 170                 175

Phe Gln Tyr Leu Leu Lys Gln Lys Glu Lys Lys Glu Arg Ser Leu Ile
            180                 185                 190

Leu Thr Thr Thr Lys Arg Leu Ala Glu Glu Ile Ser Lys Tyr Leu Gln
```

-continued

```
        195                 200                 205

Glu Glu Lys Leu Gln Asn Val Tyr Tyr Leu His Ser Glu Met Thr Thr
    210                 215                 220

Phe Glu Arg Asp Glu Ile Ile Ile Lys Leu Arg Lys Gly Ile Tyr Asp
225                 230                 235                 240

Ala Ile Val Gly Ile Asn Leu Leu Arg Glu Gly Val Asp Ile Pro Glu
                245                 250                 255

Val Ser Leu Ile Phe Val Leu Glu Ala Gly Leu Val Ser Phe Leu Arg
            260                 265                 270

Ser Ala Cys Glu Leu Gly Thr Pro Gly Arg Pro Ala
        275                 280


<210> SEQ ID NO 21
<211> LENGTH: 843
<212> TYPE: DNA
<213> ORGANISM: Artificial Sequence
<220> FEATURE:
<223> OTHER INFORMATION: Description of Artificial Sequence:Clone pAD700

<400> SEQUENCE: 21

atgcccaaat taaaccgact tagagcccga tttgtccaga ttcaaaacat tgaaaaaatg     60

acaaatgtaa tggaaatgat tgcgaatgca aaaattccaa aaataaaaaa caagtttaaa    120

attgttcaag aatattttga aaatttagat tatatttttc aaaatattct tgcaaattta    180

tctaagaagg ttgaggaatt aactaatgct gattccaaaa aaaatcttta tattattttt    240

ggatcaaatt taggtttttg tggtgccctt aataatttaa tcttaaaaaa tgttgtccca    300

caacttcaga aaaatgatga aattatcgtc tttggtgaaa aaatttataa ttttttgtca    360

ataaattact ctaatttaat tattaaattt tttctaaata ttgaagaaac taattttagt    420

gaaccaattt tagaaatctc aaactttgta aatcaatcga tttttgagag aaaatataaa    480

aaaattttta tttgttataa caaatttatc agtattatac attcaagccc agagatgcaa    540

aatttatttg atttcaaaaa aaatactata aaatacggtg gttacgggat tgagtttgaa    600

ccaaatgcta ctgaggtttt taaaaaatta atgccctttt atataaaatc catccttgaa    660

aaacttttta tcgaatccaa attagttgag acttcaacta gacgaacatc aatggaaagt    720

gcactgaaaa tgccagttga aattttgcat aagtttagaa acagaaataa ttccagtcgt    780

ccagccatga ttaccccaga aattattgag attattagtg gtaaaatgtt gaaaaagtta    840

ggt                                                                  843


<210> SEQ ID NO 22
<211> LENGTH: 281
<212> TYPE: PRT
<213> ORGANISM: Artificial Sequence
<220> FEATURE:
<223> OTHER INFORMATION: Description of Artificial Sequence:Deduced
      protein sequence from clone pAD700

<400> SEQUENCE: 22

Met Pro Lys Leu Asn Arg Leu Arg Ala Arg Phe Val Gln Ile Gln Asn
  1               5                  10                  15

Ile Glu Lys Met Thr Asn Val Met Glu Met Ile Ala Asn Ala Lys Ile
             20                  25                  30

Pro Lys Ile Lys Asn Lys Phe Lys Ile Val Gln Glu Tyr Phe Glu Asn
         35                  40                  45

Leu Asp Tyr Ile Phe Gln Asn Ile Leu Ala Asn Leu Ser Lys Lys Val
     50                  55                  60
```

```
Glu Glu Leu Thr Asn Ala Asp Ser Lys Lys Asn Leu Tyr Ile Ile Phe
 65                  70                  75                  80

Gly Ser Asn Leu Gly Phe Cys Gly Ala Leu Asn Asn Leu Ile Leu Lys
                85                  90                  95

Asn Val Val Pro Gln Leu Gln Lys Asn Asp Glu Ile Ile Val Phe Gly
            100                 105                 110

Glu Lys Ile Tyr Asn Phe Leu Ser Ile Asn Tyr Ser Asn Leu Ile Ile
        115                 120                 125

Lys Phe Phe Leu Asn Ile Glu Glu Thr Asn Phe Ser Glu Pro Ile Leu
    130                 135                 140

Glu Ile Ser Asn Phe Val Asn Gln Ser Ile Phe Glu Arg Lys Tyr Lys
145                 150                 155                 160

Lys Ile Phe Ile Cys Tyr Asn Lys Phe Ile Ser Ile Ile His Ser Ser
                165                 170                 175

Pro Glu Met Gln Asn Leu Phe Asp Phe Lys Lys Asn Thr Ile Lys Tyr
            180                 185                 190

Gly Gly Tyr Gly Ile Glu Phe Glu Pro Asn Ala Thr Glu Val Phe Lys
        195                 200                 205

Lys Leu Met Pro Phe Tyr Ile Lys Ser Ile Leu Glu Lys Leu Phe Ile
    210                 215                 220

Glu Ser Lys Leu Val Glu Thr Ser Thr Arg Arg Thr Ser Met Glu Ser
225                 230                 235                 240

Ala Leu Lys Met Pro Val Glu Ile Leu His Lys Phe Arg Asn Arg Asn
                245                 250                 255

Asn Ser Ser Arg Pro Ala Met Ile Thr Pro Glu Ile Ile Glu Ile Ile
            260                 265                 270

Ser Gly Lys Met Leu Lys Lys Leu Gly
        275                 280

<210> SEQ ID NO 23
<211> LENGTH: 615
<212> TYPE: DNA
<213> ORGANISM: Artificial Sequence
<220> FEATURE:
<223> OTHER INFORMATION: Description of Artificial Sequence:Clone pAD711

<400> SEQUENCE: 23

tcaggtatgt caaaaaatat taaggaaatt tcaatcctac cccttaaatt aaatcctgct     60

ggaattatgc ctgtaatttt tgccttaatt atcgtttcac tgccgacact ttttagcgga    120

tttcttgata gaaatacctc agcagttcgg aattgaatag ataataatat gcaaatttat    180

cacccaatcg gtcttatcat ttttattgtt tttaatgtct ccttttcaat aataatgtcc    240

ttacaacaat cccgagttga taaaattgca caggattttg ccaaaaattc aacttttatc    300

cctgggattc gcccaggaga acagactgaa gattatttaa tttcagtggt tttgcgactt    360

tcagttttca gtgcgattta tcttaccttt ttaggaattc tccaacctgt tgaaattatg    420

ttaggtcttc cttcggcaat cacaatttca ggaacttcga taataatttt agcaacaact    480

acacttgaaa cgatttcgca gatcaaagcc cgttatgatg cacaaaaagt tctaaaacaa    540

agtaaaaaga tccgcaaaaa tttacaagtt cgaaaaaatt ctccttctat tgattcaaat    600

caggatcttt tatgg                                                     615

<210> SEQ ID NO 24
<211> LENGTH: 205
<212> TYPE: PRT
```

<213> ORGANISM: Artificial Sequence
<220> FEATURE:
<223> OTHER INFORMATION: Description of Artificial Sequence:Deduced protein sequence from clone pAD711

<400> SEQUENCE: 24

```
Ser Gly Met Ser Lys Asn Ile Lys Glu Ile Ser Ile Leu Pro Leu Lys
  1               5                  10                  15

Leu Asn Pro Ala Gly Ile Met Pro Val Ile Phe Ala Leu Ile Ile Val
             20                  25                  30

Ser Leu Pro Thr Leu Phe Ser Gly Phe Leu Asp Arg Asn Thr Ser Ala
         35                  40                  45

Val Arg Asn Trp Ile Asp Asn Asn Met Gln Ile Tyr His Pro Ile Gly
     50                  55                  60

Leu Ile Ile Phe Ile Val Phe Asn Val Ser Phe Ser Ile Ile Met Ser
 65                  70                  75                  80

Leu Gln Gln Ser Arg Val Asp Lys Ile Ala Gln Asp Phe Ala Lys Asn
                 85                  90                  95

Ser Thr Phe Ile Pro Gly Ile Arg Pro Gly Glu Gln Thr Glu Asp Tyr
            100                 105                 110

Leu Ile Ser Val Val Leu Arg Leu Ser Val Phe Ser Ala Ile Tyr Leu
        115                 120                 125

Thr Phe Leu Gly Ile Leu Gln Pro Val Glu Ile Met Leu Gly Leu Pro
    130                 135                 140

Ser Ala Ile Thr Ile Ser Gly Thr Ser Ile Ile Ile Leu Ala Thr Thr
145                 150                 155                 160

Thr Leu Glu Thr Ile Ser Gln Ile Lys Ala Arg Tyr Asp Ala Gln Lys
                165                 170                 175

Val Leu Lys Gln Ser Lys Lys Ile Arg Lys Asn Leu Gln Val Arg Lys
            180                 185                 190

Asn Ser Pro Ser Ile Asp Ser Asn Gln Asp Leu Leu Trp
        195                 200                 205
```

<210> SEQ ID NO 25
<211> LENGTH: 648
<212> TYPE: DNA
<213> ORGANISM: Artificial Sequence
<220> FEATURE:
<223> OTHER INFORMATION: Description of Artificial Sequence:Clone pAD721

<400> SEQUENCE: 25

```
atcgccgaag aagtttcaag tttttctccg tttgaccgac ttttattttt taggatgtta     60

gatactgcaa ctgcaggtga tattttcacc tacttttcac cagaaattca gaccaaatta    120

gtactaagtt taccaaatga gctaatcaat aaattacttg atgaacttta tgttgatgaa    180

attgtcgaac ttcttgatga agtccctgat aatgttgcca aaagaatttt gcgcaacatt    240

gacattgata ctcgtaaaca aataaatcaa cttttgcagt ataccgacga tcaaattggc    300

gcttttatgt cagttgatat cgtctatctt tttaaagatt cgacttgtca tcaagcactt    360

gaaaaaatta gaaactataa agatatctcc gaattagtgc attattatta tgtcgttgat    420

caaaacaaga aaataatcgg ggcaactact ttagaagata ttgtcttttc tgatcctaat    480

actcagatca aagaaattgt ttttcaagtc ccttttcttg ttacactgat aaaaaagatt    540

atgccgccga agtttttgcc caaaatgatt tttccagtac tcccggttgt taataccagc    600

cagaaactaa tccgaatggt tccagttgat gatattatcc gatattgt                 648
```

<210> SEQ ID NO 26
<211> LENGTH: 216
<212> TYPE: PRT
<213> ORGANISM: Artificial Sequence
<220> FEATURE:
<223> OTHER INFORMATION: Description of Artificial Sequence:Deduced protein sequence from clone pAD721

<400> SEQUENCE: 26

```
Ile Ala Glu Glu Val Ser Ser Phe Ser Pro Phe Asp Arg Leu Leu Phe
  1               5                  10                  15

Phe Arg Met Leu Asp Thr Ala Thr Ala Gly Asp Ile Phe Thr Tyr Phe
             20                  25                  30

Ser Pro Glu Ile Gln Thr Lys Leu Val Leu Ser Leu Pro Asn Glu Leu
         35                  40                  45

Ile Asn Lys Leu Leu Asp Glu Leu Tyr Val Asp Glu Ile Val Glu Leu
     50                  55                  60

Leu Asp Glu Val Pro Asp Asn Val Ala Lys Arg Ile Leu Arg Asn Ile
 65                  70                  75                  80

Asp Ile Asp Thr Arg Lys Gln Ile Asn Gln Leu Leu Gln Tyr Thr Asp
                 85                  90                  95

Asp Gln Ile Gly Ala Phe Met Ser Val Asp Ile Val Tyr Leu Phe Lys
            100                 105                 110

Asp Ser Thr Cys His Gln Ala Leu Glu Lys Ile Arg Asn Tyr Lys Asp
        115                 120                 125

Ile Ser Glu Leu Val His Tyr Tyr Tyr Val Val Asp Gln Asn Lys Lys
    130                 135                 140

Ile Ile Gly Ala Thr Thr Leu Glu Asp Ile Val Phe Ser Asp Pro Asn
145                 150                 155                 160

Thr Gln Ile Lys Glu Ile Val Phe Gln Val Pro Phe Leu Val Thr Leu
                165                 170                 175

Ile Lys Lys Ile Met Pro Pro Lys Phe Leu Pro Lys Met Ile Phe Pro
            180                 185                 190

Val Leu Pro Val Val Asn Thr Ser Gln Lys Leu Ile Arg Met Val Pro
        195                 200                 205

Val Asp Asp Ile Ile Arg Tyr Cys
    210                 215
```

<210> SEQ ID NO 27
<211> LENGTH: 837
<212> TYPE: DNA
<213> ORGANISM: Artificial Sequence
<220> FEATURE:
<223> OTHER INFORMATION: Description of Artificial Sequence:Clone pAD727

<400> SEQUENCE: 27

```
tcatttggtt caggatttaa tttagcaatt gattttagtg gcggaactaa ctttttaatt     60

gaaagctcaa attcaagtta tgatttaatt acaaaggaaa aagccgaaaa aataattagt    120

tttcttgatt cacaaaatat aaacaagtca aattcaacaa ttttgcttaa tccattaaat    180

gaaaatggaa atatttttaa tcttgaaatt aaaacaaaac ttgatctagc aacaaaaatt    240

gcctcattaa atacggcaat ccagaataat ttttctaata ttcgaatgac aaattattca    300

atttcgaatg aagaagctca aaaattaatt ttcaatgcaa ttctttcagt tggaatcgca    360

cttatttttg taactatttt tacgctaatt aggtttaaat ggactttttc gcttgcaata    420

attttctcac ttctttttaa tgttttaatg gttttgctag caattattat tacacggatc    480

gaaatatcgc agaatttagt tgttgcaatt cttactttaa ttggttatac agtaaatgat    540
```

-continued

```
acaatcgtgg tttttgatag agtaaaagca agattttcag aaataaatca tgaaaatgtt    600

tataaatttg ataaaattaa agaaatttcc ttacaagcaa ttagagaaac agcaaaaagg    660

tcggtatata catccttgac aaccatttta acaattgttg ttttaatgat tttttatgaa    720

tcaattgata ttgtctttag cctgacgatg ttaattggtg tgataattgg aacatattcc    780

tccttattta tcgcaacccg catttggatt attcttgaat catcccgtaa tcgtaaa       837
```

```
<210> SEQ ID NO 28
<211> LENGTH: 279
<212> TYPE: PRT
<213> ORGANISM: Artificial Sequence
<220> FEATURE:
<223> OTHER INFORMATION: Description of Artificial Sequence:Deduced
      protein sequence from clone pAD727

<400> SEQUENCE: 28

Ser Phe Gly Ser Gly Phe Asn Leu Ala Ile Asp Phe Ser Gly Gly Thr
  1               5                  10                  15

Asn Phe Leu Ile Glu Ser Ser Asn Ser Ser Tyr Asp Leu Ile Thr Lys
             20                  25                  30

Glu Lys Ala Glu Lys Ile Ile Ser Phe Leu Asp Ser Gln Asn Ile Asn
         35                  40                  45

Lys Ser Asn Ser Thr Ile Leu Leu Asn Pro Leu Asn Glu Asn Gly Asn
     50                  55                  60

Ile Phe Asn Leu Glu Ile Lys Thr Lys Leu Asp Leu Ala Thr Lys Ile
 65                  70                  75                  80

Ala Ser Leu Asn Thr Ala Ile Gln Asn Asn Phe Ser Asn Ile Arg Met
                 85                  90                  95

Thr Asn Tyr Ser Ile Ser Asn Glu Glu Ala Gln Lys Leu Ile Phe Asn
            100                 105                 110

Ala Ile Leu Ser Val Gly Ile Ala Leu Ile Phe Val Thr Ile Phe Thr
        115                 120                 125

Leu Ile Arg Phe Lys Trp Thr Phe Ser Leu Ala Ile Ile Phe Ser Leu
    130                 135                 140

Leu Phe Asn Val Leu Met Val Leu Leu Ala Ile Ile Ile Thr Arg Ile
145                 150                 155                 160

Glu Ile Ser Gln Asn Leu Val Val Ala Ile Leu Thr Leu Ile Gly Tyr
                165                 170                 175

Thr Val Asn Asp Thr Ile Val Val Phe Asp Arg Val Lys Ala Arg Phe
            180                 185                 190

Ser Glu Ile Asn His Glu Asn Val Tyr Lys Phe Asp Lys Ile Lys Glu
        195                 200                 205

Ile Ser Leu Gln Ala Ile Arg Glu Thr Ala Lys Arg Ser Val Tyr Thr
    210                 215                 220

Ser Leu Thr Thr Ile Leu Thr Ile Val Val Leu Met Ile Phe Tyr Glu
225                 230                 235                 240

Ser Ile Asp Ile Val Phe Ser Leu Thr Met Leu Ile Gly Val Ile Ile
                245                 250                 255

Gly Thr Tyr Ser Ser Leu Phe Ile Ala Thr Arg Ile Trp Ile Ile Leu
            260                 265                 270

Glu Ser Ser Arg Asn Arg Lys
        275
```

```
<210> SEQ ID NO 29
<211> LENGTH: 2523
```

-continued

<212> TYPE: DNA
<213> ORGANISM: Artificial Sequence
<220> FEATURE:
<223> OTHER INFORMATION: Description of Artificial Sequence:Clone pAD742

<400> SEQUENCE: 29

```
atgaagttaa taaaaattga aattgaaggt tttaaatcct ttgctgaacc tgtaagtatt     60
aaatttgatg gttcaattgt tggaataatt gggccaaatg gctctggaaa atccaatata    120
aatgatgcaa ttaaatgagt tttaggcgaa aaatcagtta aacaattacc gggcccaaat    180
atggatgatg gcatttttgc tggctcaaaa acaggtatga tcgcaattga aaaaattgaa    240
atcaggacaa aagagcttga aaaacaagta aaacagcttg aaaaacaagc agaaaatgca    300
aaaatttacc tcgaaaaatc aaagcaatta gaatctgttg aagtcggctt aattgtctct    360
gatattaaaa agtaccaaac agaattagat caagtccagg aaaaattaaa tgatctaaaa    420
tttcaagaac ctaaatttat cagcgaaatt gaagcaaatg agaaaataat tattacaaat    480
acacaaaaaa ggtcagaaat tgaagctgaa atcaacacta aaaaccgcga aattcaccgc    540
ctaaaagagc aaattaatac cctaaattta gcttatgcaa aagcaactca acttcaagaa    600
atgattttat caagtgaaat tagtgtaaat tttgagcaaa aaatggctgc tttgcgccaa    660
aaatatagtc ttataagcgc gcaaaaagac aattttgcaa aattaatcag ccaaaacaag    720
ctcaaaaaac tagaaattga agaaaaactt aatacattta ggacacaaaa gggtgaaatt    780
gaaaggaatt tatacagtct aaattccgaa aaaattatta gtcaaactag aatctccgag    840
ctaaaaaagt ccttagaatc aatgtctttt ttgccaaagg ggacaaaaat cattatcgaa    900
aatagctttc tttttcctgg atattgtggg cttgtctctg atttaatcaa aattttccca    960
aaatatacag gcgcaattga agccgcattg ggtccaactt taaaacaaat tgttgttgac   1020
caacctgaaa ccgcagtttc agcaattaat tttctaaaga aaaattatgc aggaagcgca   1080
acatttatcc ccctttcaac attaaaaccg cgatttattc ccgatttata tcttgaacat   1140
ctaaattcac aaaaaggttt tataaattta gctagcaatt tagtcgattt tgaaaaaaaa   1200
tacaagattt tagcggattt tttactagga gggattattg ttgctgatac aattgattca   1260
gcaaatcgaa tcgcaaactt ccttaaccac aaaaacatga tcgtaacttt agacggcgat   1320
gttattagaa ctagcgggat aatttctggg ggtcataaga taaaaaatga ttcttccttt   1380
tcaattcagt ataaaatcga tgaactaaca aataatttga attttttga agaaaaaatt    1440
caagaattta aagttaaatc taatgaattt gaacagttaa ttacaagaga atctgtattt   1500
ttacagcaaa ttaatattaa tcttaatgat ttagagcaaa aatttagtaa ttctgaaaat   1560
gaattaatcg aaattaaagc tcaaaatgaa ggtcttgaag agagtctaaa tcaaaaagat   1620
gacctaaatt taagtctaaa tcgaacttta aaagaaaaaa ttgaacttga aaatgtggtt   1680
ttagaacttg aaaatcaatg caaaatttta aaaactgaaa aaaaacagct cgataatcaa   1740
atttcagaac ttacagtttt agttcaagaa cttaaccaaa aacagcgaaa aatcaacgca   1800
gatcttaacc aaaatcaaaa ttacaaagac aaatatgaat ttttaattac aaatttacga   1860
aataatttat cccaaaaata cagtctaact tttgaaggcg cagctcaaaa atatgaactt   1920
gaaattccag aaaaagatgc tcgcgaattt gttaatagtc taaatttaga gattaaagcg   1980
cttggaaatg ttaatttaga tgcaattaat gactttgaaa caacgagtca aagactcgaa   2040
aaactaaaaa aaagtcaaaa tgaacttgaa actgccaggt caaaaatttt agaagttatc   2100
tcggatttag ataaaattat cattggaaaa acccaggaaa ttgtcgatct agttaattcc   2160
```

-continued

```
gagtttaacc ttgttttcca gaatatgttt ggtgggggaa gtgcaaaaat ttattttagt   2220

gataaaaacg atattttaaa ttcggggatt gaaataagtg cccaaccacc tggaaaaact   2280

atcaaaaata ttaggctttt ttctgggggc gaaaaggcaa ttattgcaat ttcacttttg   2340

ttttcaatta ttaaggcaag accaattccg ctttgcattc ttgatgaagt tgaagctgcc   2400

cttgatgagt caaatgtgat cagatatgtg gaatttcgaa agcagttaaa acaaaaaacg   2460

cagtttttga tcatcaccca tcggcacgga acgatgtccc gagttgatca acttttagga   2520

atc                                                                 2523
```

<210> SEQ ID NO 30
<211> LENGTH: 841
<212> TYPE: PRT
<213> ORGANISM: Artificial Sequence
<220> FEATURE:
<223> OTHER INFORMATION: Description of Artificial Sequence:Deduced protein sequence from clone pAD742

<400> SEQUENCE: 30

```
Met Lys Leu Ile Lys Ile Glu Ile Glu Gly Phe Lys Ser Phe Ala Glu
  1               5                  10                  15

Pro Val Ser Ile Lys Phe Asp Gly Ser Ile Val Gly Ile Ile Gly Pro
             20                  25                  30

Asn Gly Ser Gly Lys Ser Asn Ile Asn Asp Ala Ile Lys Trp Val Leu
         35                  40                  45

Gly Glu Lys Ser Val Lys Gln Leu Pro Gly Pro Asn Met Asp Asp Gly
     50                  55                  60

Ile Phe Ala Gly Ser Lys Thr Gly Met Ile Ala Ile Glu Lys Ile Glu
 65                  70                  75                  80

Ile Arg Thr Lys Glu Leu Glu Lys Gln Val Lys Gln Leu Glu Lys Gln
                 85                  90                  95

Ala Glu Asn Ala Lys Ile Tyr Leu Glu Lys Ser Lys Gln Leu Glu Ser
            100                 105                 110

Val Glu Val Gly Leu Ile Val Ser Asp Ile Lys Lys Tyr Gln Thr Glu
        115                 120                 125

Leu Asp Gln Val Gln Glu Lys Leu Asn Asp Leu Lys Phe Gln Glu Pro
    130                 135                 140

Lys Phe Ile Ser Glu Ile Glu Ala Asn Glu Lys Ile Ile Ile Thr Asn
145                 150                 155                 160

Thr Gln Lys Arg Ser Glu Ile Glu Ala Glu Ile Asn Thr Lys Asn Arg
                165                 170                 175

Glu Ile His Arg Leu Lys Glu Gln Ile Asn Thr Leu Asn Leu Ala Tyr
            180                 185                 190

Ala Lys Ala Thr Gln Leu Gln Glu Met Ile Leu Ser Ser Glu Ile Ser
        195                 200                 205

Val Asn Phe Glu Gln Lys Met Ala Ala Leu Arg Gln Lys Tyr Ser Leu
    210                 215                 220

Ile Ser Ala Gln Lys Asp Asn Phe Ala Lys Leu Ile Ser Gln Asn Lys
225                 230                 235                 240

Leu Lys Lys Leu Glu Ile Glu Glu Lys Leu Asn Thr Phe Arg Thr Gln
                245                 250                 255

Lys Gly Glu Ile Glu Arg Asn Leu Tyr Ser Leu Asn Ser Glu Lys Ile
            260                 265                 270

Ile Ser Gln Thr Arg Ile Ser Glu Leu Lys Lys Ser Leu Glu Ser Met
        275                 280                 285
```

-continued

```
Ser Phe Leu Pro Lys Gly Thr Lys Ile Ile Ile Glu Asn Ser Phe Leu
    290                 295                 300

Phe Pro Gly Tyr Cys Gly Leu Val Ser Asp Leu Ile Lys Ile Phe Pro
305                 310                 315                 320

Lys Tyr Thr Gly Ala Ile Glu Ala Ala Leu Gly Pro Thr Leu Lys Gln
                325                 330                 335

Ile Val Val Asp Gln Pro Glu Thr Ala Val Ser Ala Ile Asn Phe Leu
            340                 345                 350

Lys Lys Asn Tyr Ala Gly Ser Ala Thr Phe Ile Pro Leu Ser Thr Leu
        355                 360                 365

Lys Pro Arg Phe Ile Pro Asp Leu Tyr Leu Glu His Leu Asn Ser Gln
    370                 375                 380

Lys Gly Phe Ile Asn Leu Ala Ser Asn Leu Val Asp Phe Glu Lys Lys
385                 390                 395                 400

Tyr Lys Ile Leu Ala Asp Phe Leu Leu Gly Gly Ile Ile Val Ala Asp
                405                 410                 415

Thr Ile Asp Ser Ala Asn Arg Ile Ala Asn Phe Leu Asn His Lys Asn
            420                 425                 430

Met Ile Val Thr Leu Asp Gly Asp Val Ile Arg Thr Ser Gly Ile Ile
        435                 440                 445

Ser Gly Gly His Lys Ile Lys Asn Asp Ser Ser Phe Ser Ile Gln Tyr
    450                 455                 460

Lys Ile Asp Glu Leu Thr Asn Asn Leu Asn Phe Phe Glu Glu Lys Ile
465                 470                 475                 480

Gln Glu Phe Lys Val Lys Ser Asn Glu Phe Glu Gln Leu Ile Thr Arg
                485                 490                 495

Glu Ser Val Phe Leu Gln Gln Ile Asn Ile Asn Leu Asn Asp Leu Glu
            500                 505                 510

Gln Lys Phe Ser Asn Ser Glu Asn Glu Leu Ile Glu Ile Lys Ala Gln
        515                 520                 525

Asn Glu Gly Leu Glu Glu Ser Leu Asn Gln Lys Asp Asp Leu Asn Leu
    530                 535                 540

Ser Leu Asn Arg Thr Leu Lys Glu Lys Ile Glu Leu Glu Asn Val Val
545                 550                 555                 560

Leu Glu Leu Glu Asn Gln Cys Lys Ile Leu Lys Thr Glu Lys Lys Gln
                565                 570                 575

Leu Asp Asn Gln Ile Ser Glu Leu Thr Val Leu Val Gln Glu Leu Asn
            580                 585                 590

Gln Lys Gln Arg Lys Ile Asn Ala Asp Leu Asn Gln Asn Gln Asn Tyr
        595                 600                 605

Lys Asp Lys Tyr Glu Phe Leu Ile Thr Asn Leu Arg Asn Asn Leu Ser
    610                 615                 620

Gln Lys Tyr Ser Leu Thr Phe Glu Gly Ala Ala Gln Lys Tyr Glu Leu
625                 630                 635                 640

Glu Ile Pro Glu Lys Asp Ala Arg Glu Phe Val Asn Ser Leu Asn Leu
                645                 650                 655

Glu Ile Lys Ala Leu Gly Asn Val Asn Leu Asp Ala Ile Asn Asp Phe
            660                 665                 670

Glu Thr Thr Ser Gln Arg Leu Glu Lys Leu Lys Lys Ser Gln Asn Glu
        675                 680                 685

Leu Glu Thr Ala Arg Ser Lys Ile Leu Glu Val Ile Ser Asp Leu Asp
    690                 695                 700

Lys Ile Ile Ile Gly Lys Thr Gln Glu Ile Val Asp Leu Val Asn Ser
```

```
705                 710                 715                 720

Glu Phe Asn Leu Val Phe Gln Asn Met Phe Gly Gly Gly Ser Ala Lys
                725                 730                 735

Ile Tyr Phe Ser Asp Lys Asn Asp Ile Leu Asn Ser Gly Ile Glu Ile
            740                 745                 750

Ser Ala Gln Pro Pro Gly Lys Thr Ile Lys Asn Ile Arg Leu Phe Ser
        755                 760                 765

Gly Gly Glu Lys Ala Ile Ile Ala Ile Ser Leu Leu Phe Ser Ile Ile
    770                 775                 780

Lys Ala Arg Pro Ile Pro Leu Cys Ile Leu Asp Glu Val Glu Ala Ala
785                 790                 795                 800

Leu Asp Glu Ser Asn Val Ile Arg Tyr Val Glu Phe Arg Lys Gln Leu
                805                 810                 815

Lys Gln Lys Thr Gln Phe Leu Ile Ile Thr His Arg His Gly Thr Met
            820                 825                 830

Ser Arg Val Asp Gln Leu Leu Gly Ile
        835                 840
```

<210> SEQ ID NO 31
<211> LENGTH: 1698
<212> TYPE: DNA
<213> ORGANISM: Artificial Sequence
<220> FEATURE:
<223> OTHER INFORMATION: Description of Artificial Sequence:Clone pAD760

<400> SEQUENCE: 31

```
atgaatagaa aaaaaaccga aaaatcaaaa attagttcaa aagatagtaa aaaattaata     60

attcaagcta tccaagatgt ggcaaaaaat agcgaattaa atctggaagc agttattgat    120

atttttcagg aagcaattga atttgtaata acaaagaaaa ttgacccaga tgcgcaaata    180

aaaattgaag ctgatcttga acaattgagt tttaaagttt ttaatacaaa cgggattgtt    240

gttgaagaaa attattttga tgatcttaca gatgaggaaa aagttaacga tcttgtttct    300

tttattttac tatcaaaggc aaaagaaact gatcctgaga ttcaggttga tgatattttt    360

tcaattgaaa ttaatcttga aagttttgaa cattgacttt ttatggcaat tatgcacgct    420

tttaagcaaa aaatttctga aattgtccga aataatgttt ataacaaata tttatcgctt    480

aaaaataacg tagttttggc cactgttact aataaaattg ctgctggtta tattttcgaa    540

attgacgatg ataaagtttc tgcctttatg ccaagccatt atgcaagtgg acaaaattta    600

aaaataggca ctaaacatga agttgtaatt gaaaatgtat caaaaaatac aaaacagtcg    660

caggttgtga tatcctcaaa atcagttcaa cttgtcaaga aaaaaataat cgatgcaatc    720

cctgaactac agtcaaaatt tcttgaaatc acttcaattg cacggattcc aggggaaaga    780

tgtaaagtcg caattcgcag aaatgaagat gccgaagctg ataatatttc tgaaatcggc    840

tcaattgtag gagcaactgg ctcaagagtt cttgcaattt ctcaagaact tcaaggtgaa    900

aaaattgagg tgattaaata tgatgataat attgtcaaat ttattgttaa tgcgatgtcg    960

ccttcaaaag ttatttgcgt aaaagagttc aaaataggtc ataaattacg tcgttttatc   1020

gtagttgttc ctgattttca acatagttta gccattggaa aaaacggttc aaatgttaaa   1080

ctagtagcag atctaacacg ttgtcaagtg caaattatcc cgtattcaag cgcgctaaaa   1140

gatcaaaatt ttaaaattga atgaaatgga aatattaaag acattcaaga actaaacagt   1200

cttaacaatg agtatattca tcgccagcag ggtagaattt atcaaaatca tcggaattca   1260

tatggtcaag gtaataataa ttttgactta attttacagc aattcgaatc tgatattcgc   1320
```

-continued

```
gagttagaaa aaccttatgg gattgaaaac gagtttatac caaaaaatga gcaaaaacag   1380

gtaagaagtc accaagaatt tccaaaaaac aagaataatc tagcaaaagc agcaactaaa   1440

tcgcgtaatt ttaacaaaag ccagaatatc cgcgaaaata tttcaaaaga ttttgattat   1500

ggctttgaaa acgagaaaga ttctaattct ttccaaaata ttagtcaaag atcttttttt   1560

gatgcagatt cactttttga ttcggctcta aatgaggcaa ttagtgaaaa cgagttaatc   1620

gataaaattc accaagaaga ggaaaaaaaa caagaattat tattacaaga gaaggaaaaa   1680

tgagcaaaaa atgaagct                                                 1698


<210> SEQ ID NO 32
<211> LENGTH: 566
<212> TYPE: PRT
<213> ORGANISM: Artificial Sequence
<220> FEATURE:
<223> OTHER INFORMATION: Description of Artificial Sequence:Deduced
      protein sequence from clone pAD760

<400> SEQUENCE: 32

Met Asn Arg Lys Lys Thr Glu Lys Ser Lys Ile Ser Ser Lys Asp Ser
  1               5                  10                  15

Lys Lys Leu Ile Ile Gln Ala Ile Gln Asp Val Ala Lys Asn Ser Glu
             20                  25                  30

Leu Asn Leu Glu Ala Val Ile Asp Ile Phe Gln Glu Ala Ile Glu Phe
         35                  40                  45

Val Ile Thr Lys Lys Ile Asp Pro Asp Ala Gln Ile Lys Ile Glu Ala
     50                  55                  60

Asp Leu Glu Gln Leu Ser Phe Lys Val Phe Asn Thr Asn Gly Ile Val
 65                  70                  75                  80

Val Glu Glu Asn Tyr Phe Asp Asp Leu Thr Asp Glu Glu Lys Val Asn
                 85                  90                  95

Asp Leu Val Ser Phe Ile Leu Leu Ser Lys Ala Lys Glu Thr Asp Pro
            100                 105                 110

Glu Ile Gln Val Asp Asp Ile Phe Ser Ile Glu Ile Asn Leu Glu Ser
        115                 120                 125

Phe Glu His Trp Leu Phe Met Ala Ile Met His Ala Phe Lys Gln Lys
    130                 135                 140

Ile Ser Glu Ile Val Arg Asn Asn Val Tyr Asn Lys Tyr Leu Ser Leu
145                 150                 155                 160

Lys Asn Asn Val Val Leu Ala Thr Val Thr Asn Lys Ile Ala Ala Gly
                165                 170                 175

Tyr Ile Phe Glu Ile Asp Asp Asp Lys Val Ser Ala Phe Met Pro Ser
            180                 185                 190

His Tyr Ala Ser Gly Gln Asn Leu Lys Ile Gly Thr Lys His Glu Val
        195                 200                 205

Val Ile Glu Asn Val Ser Lys Asn Thr Lys Gln Ser Gln Val Val Ile
    210                 215                 220

Ser Ser Lys Ser Val Gln Leu Val Lys Lys Lys Ile Ile Asp Ala Ile
225                 230                 235                 240

Pro Glu Leu Gln Ser Lys Phe Leu Glu Ile Thr Ser Ile Ala Arg Ile
                245                 250                 255

Pro Gly Glu Arg Cys Lys Val Ala Ile Arg Arg Asn Glu Asp Ala Glu
            260                 265                 270

Ala Asp Asn Ile Ser Glu Ile Gly Ser Ile Val Gly Ala Thr Gly Ser
        275                 280                 285
```

-continued

```
Arg Val Leu Ala Ile Ser Gln Glu Leu Gln Gly Glu Lys Ile Glu Val
    290                 295                 300

Ile Lys Tyr Asp Asp Asn Ile Val Lys Phe Ile Val Asn Ala Met Ser
305                 310                 315                 320

Pro Ser Lys Val Ile Cys Val Lys Glu Phe Lys Ile Gly His Lys Leu
                325                 330                 335

Arg Arg Phe Ile Val Val Val Pro Asp Phe Gln His Ser Leu Ala Ile
            340                 345                 350

Gly Lys Asn Gly Ser Asn Val Lys Leu Val Ala Asp Leu Thr Arg Cys
        355                 360                 365

Gln Val Gln Ile Ile Pro Tyr Ser Ser Ala Leu Lys Asp Gln Asn Phe
    370                 375                 380

Lys Ile Glu Trp Asn Gly Asn Ile Lys Asp Ile Gln Glu Leu Asn Ser
385                 390                 395                 400

Leu Asn Asn Glu Tyr Ile His Arg Gln Gln Gly Arg Ile Tyr Gln Asn
                405                 410                 415

His Arg Asn Ser Tyr Gly Gln Gly Asn Asn Asn Phe Asp Leu Ile Leu
            420                 425                 430

Gln Gln Phe Glu Ser Asp Ile Arg Glu Leu Glu Lys Pro Tyr Gly Ile
        435                 440                 445

Glu Asn Glu Phe Ile Pro Lys Asn Glu Gln Lys Gln Val Arg Ser His
    450                 455                 460

Gln Glu Phe Pro Lys Asn Lys Asn Asn Leu Ala Lys Ala Ala Thr Lys
465                 470                 475                 480

Ser Arg Asn Phe Asn Lys Ser Gln Asn Ile Arg Glu Asn Ile Ser Lys
                485                 490                 495

Asp Phe Asp Tyr Gly Phe Glu Asn Glu Lys Asp Ser Asn Ser Phe Gln
            500                 505                 510

Asn Ile Ser Gln Arg Ser Phe Phe Asp Ala Asp Ser Leu Phe Asp Ser
        515                 520                 525

Ala Leu Asn Glu Ala Ile Ser Glu Asn Glu Leu Ile Asp Lys Ile His
    530                 535                 540

Gln Glu Glu Glu Lys Lys Gln Glu Leu Leu Leu Gln Glu Lys Glu Lys
545                 550                 555                 560

Trp Ala Lys Asn Glu Ala
                565


<210> SEQ ID NO 33
<211> LENGTH: 1860
<212> TYPE: DNA
<213> ORGANISM: Artificial Sequence
<220> FEATURE:
<223> OTHER INFORMATION: Description of Artificial Sequence:Clone pAD774

<400> SEQUENCE: 33

gaattctacc tttgatcacc taatgcaaat cgggtacatt ttgcaattta taaagatccg     60

gaagacaaaa ttccggctga aattattgtg atgtcaaaaa ataatgatgt ttggttttgc    120

caaattaatg cctcttttaa tggatattcc tataatttat taattgagca tcacgattta    180

aaaataactg aggcacttga tccttatgcc tttagtattg cgccttttga ttgaaaaaaa    240

aatgaaagtc caaaagcata tttaattgac attttttccg aaaaaactgg aaaaaatcct    300

tcaaaattag aaggatttaa caaaaatccg caaattgatg ctcaaattta tcagctgcac    360

attcgagatt tttcatctat tagtaaaaaa acagaaaata aaggtacttt tatcggagcg    420
```

-continued

```
ctagaaaatg atgtttttag ttatttaaat agcttaaaat ttaatttttt acaattatta    480

ccaatccact cttgttataa tttcagccaa aaaaacgcta gcatcctcca caaaggggat    540

ggaaacggtc attttagcac ttataattgg ggttatgacc caattggtta cttttcgata    600

aattcaagtt attcaacaga tccaatggat ccatatctgc gaatttttga gtttaaaaaa    660

tttgttgact ccgcccataa aaataagatc ggaattgttc ttgatgttga ttttagtcac    720

acctttaaaa attcaattct tgaggatgta gctcacgggc atttttaccg ggatgaagca    780

gctgttttac ctgccggatt tccgccactt gatacacgaa aaccaatggc atttaggcta    840

attttggatt ccttaatttt ttttactaaa tattataaag ttgatggatt tcgctttaat    900

ttagcatctt ttttagataa aaaagcaatt acagttattg ccagtgaact aaaaaaagtt    960

aatccaaata ttcttttata tggtgatttt tcaaatccta gtgacctacc aagcagaaat   1020

cgacttgaaa aagggaaaac aggaaatagt tttaactttg gatatttaaa cgatacaatc   1080

caaacagcaa ttatcgggag cggaaatccg cgtgataaag gtttaatttt atcaaaaact   1140

agtaaaaaat tcgctgctta tgtttcttca attccgggga acattgcaaa ttttgacttc   1200

caaaatttgc catattcaaa aaaaaaatac gacctttttg caaacgatat cagcctaaat   1260

cttgcctatc ttacttgtta taatggcccg actttagccg ataaaattct tagtgcgaca   1320

acgcgaattg gaaaaagaga atttcttgaa atctaccggc aagccttaat gatggtcaat   1380

tttgtccaag gaaaaatttc acttagtgct gggactgaat ttgctttttc aagaatttgt   1440

gatttttctg gggcagttta tcaaaattgc tatcctaatt taaacataaa aagaccgcct   1500

ttttcgtttt tagcgggcaa atatcttgat tttcattctg ataaaaccac agatttcaca   1560

aatggattga attttgaaat tcttaaaaac aatgaaatca aagagaaaat ctttgatttt   1620

cttgccgaaa ttaatcaatt tcgccaaaat tctccatttt ttcggcttga tacaaaccaa   1680

aaaatcaaaa aacagctaaa atttgaaact gttgataaca ataaaggatt aattatcttt   1740

aaaattctgc taaaaataaa gtgattaaag ttattcataa tttttcacat ctttcttatg   1800

aatatgattt taaaaatttt aatattcttt ttagctcaaa gattaaagtt attcctaatt   1860
```

<210> SEQ ID NO 34
<211> LENGTH: 620
<212> TYPE: PRT
<213> ORGANISM: Artificial Sequence
<220> FEATURE:
<223> OTHER INFORMATION: Description of Artificial Sequence:Deduced
      protein sequence from clone pAD774

<400> SEQUENCE: 34

```
Glu Phe Tyr Leu Trp Ser Pro Asn Ala Asn Arg Val His Phe Ala Ile
  1               5                  10                  15

Tyr Lys Asp Pro Glu Asp Lys Ile Pro Ala Glu Ile Ile Val Met Ser
             20                  25                  30

Lys Asn Asn Asp Val Trp Phe Cys Gln Ile Asn Ala Ser Phe Asn Gly
         35                  40                  45

Tyr Ser Tyr Asn Leu Leu Ile Glu His His Asp Leu Lys Ile Thr Glu
     50                  55                  60

Ala Leu Asp Pro Tyr Ala Phe Ser Ile Ala Pro Phe Asp Trp Lys Lys
 65                  70                  75                  80

Asn Glu Ser Pro Lys Ala Tyr Leu Ile Asp Ile Phe Ser Glu Lys Thr
                 85                  90                  95

Gly Lys Asn Pro Ser Lys Leu Glu Gly Phe Asn Lys Asn Pro Gln Ile
            100                 105                 110
```

-continued

```
Asp Ala Gln Ile Tyr Gln Leu His Ile Arg Asp Phe Ser Ser Ile Ser
        115                 120                 125

Lys Lys Thr Glu Asn Lys Gly Thr Phe Ile Gly Ala Leu Glu Asn Asp
    130                 135                 140

Val Phe Ser Tyr Leu Asn Ser Leu Lys Phe Asn Phe Leu Gln Leu Leu
145                 150                 155                 160

Pro Ile His Ser Cys Tyr Asn Phe Ser Gln Lys Asn Ala Ser Ile Leu
                165                 170                 175

His Lys Gly Asp Gly Asn Gly His Phe Ser Thr Tyr Asn Trp Gly Tyr
            180                 185                 190

Asp Pro Ile Gly Tyr Phe Ser Ile Asn Ser Ser Tyr Ser Thr Asp Pro
        195                 200                 205

Met Asp Pro Tyr Leu Arg Ile Phe Glu Phe Lys Lys Phe Val Asp Ser
    210                 215                 220

Ala His Lys Asn Lys Ile Gly Ile Val Leu Asp Val Asp Phe Ser His
225                 230                 235                 240

Thr Phe Lys Asn Ser Ile Leu Glu Asp Val Ala His Gly His Phe Tyr
                245                 250                 255

Arg Asp Glu Ala Ala Val Leu Pro Ala Gly Phe Pro Pro Leu Asp Thr
            260                 265                 270

Arg Lys Pro Met Ala Phe Arg Leu Ile Leu Asp Ser Leu Ile Phe Phe
        275                 280                 285

Thr Lys Tyr Tyr Lys Val Asp Gly Phe Arg Phe Asn Leu Ala Ser Phe
    290                 295                 300

Leu Asp Lys Lys Ala Ile Thr Val Ile Ala Ser Glu Leu Lys Lys Val
305                 310                 315                 320

Asn Pro Asn Ile Leu Leu Tyr Gly Asp Phe Ser Asn Pro Ser Asp Leu
                325                 330                 335

Pro Ser Arg Asn Arg Leu Glu Lys Gly Lys Thr Gly Asn Ser Phe Asn
            340                 345                 350

Phe Gly Tyr Leu Asn Asp Thr Ile Gln Thr Ala Ile Ile Gly Ser Gly
        355                 360                 365

Asn Pro Arg Asp Lys Gly Leu Ile Leu Ser Lys Thr Ser Lys Lys Phe
    370                 375                 380

Ala Ala Tyr Val Ser Ser Ile Pro Gly Asn Ile Ala Asn Phe Asp Phe
385                 390                 395                 400

Gln Asn Leu Pro Tyr Ser Lys Lys Lys Tyr Asp Leu Phe Ala Asn Asp
                405                 410                 415

Ile Ser Leu Asn Leu Ala Tyr Leu Thr Cys Tyr Asn Gly Pro Thr Leu
            420                 425                 430

Ala Asp Lys Ile Leu Ser Ala Thr Thr Arg Ile Gly Lys Arg Glu Phe
        435                 440                 445

Leu Glu Ile Tyr Arg Gln Ala Leu Met Met Val Asn Phe Val Gln Gly
    450                 455                 460

Lys Ile Ser Leu Ser Ala Gly Thr Glu Phe Ala Phe Ser Arg Ile Cys
465                 470                 475                 480

Asp Phe Ser Gly Gly Ser Tyr Gln Asn Cys Tyr Pro Asn Leu Asn Ile
                485                 490                 495

Lys Arg Pro Pro Phe Ser Phe Leu Ala Gly Lys Tyr Leu Asp Phe His
            500                 505                 510

Ser Asp Lys Thr Thr Asp Phe Thr Asn Gly Leu Asn Phe Glu Ile Leu
        515                 520                 525
```

-continued

```
Lys Asn Asn Glu Ile Lys Glu Lys Ile Phe Asp Phe Leu Ala Glu Ile
    530                 535                 540

Asn Gln Phe Arg Gln Asn Ser Pro Phe Phe Arg Leu Asp Thr Asn Gln
545                 550                 555                 560

Lys Ile Lys Lys Gln Leu Lys Phe Glu Thr Val Asp Asn Asn Lys Gly
                565                 570                 575

Leu Ile Ile Phe Lys Ile Leu Leu Lys Ile Lys Trp Leu Lys Leu Phe
            580                 585                 590

Ile Ile Phe His Ile Phe Leu Met Asn Met Ile Leu Lys Ile Leu Ile
        595                 600                 605

Phe Phe Leu Ala Gln Arg Leu Lys Leu Phe Leu Ile
    610                 615                 620


<210> SEQ ID NO 35
<211> LENGTH: 897
<212> TYPE: DNA
<213> ORGANISM: Artificial Sequence
<220> FEATURE:
<223> OTHER INFORMATION: Description of Artificial Sequence:Clone pAD784

<400> SEQUENCE: 35

gctttttgt ttgttgatgg tcggtatatt gaaaaagctg aaaaagatgc taaaaattgt     60

caggtttttt tacctaccaa gcaaatcttg aagatttttt caagaaaacc cgtatcaaaa    120

aatcggcatt gatctgaata tttaactatt gaccaatttg ataaaataag aagttgattt    180

ccaaatgccg attttgttaa gttacaagcc caactttttc gaattataaa aacagaagaa    240

gaaatcaaaa atatcgaaaa agctgttgaa atctcactcg cggcttataa taaaatattt    300

ccaaaaatca aaccgggaat gacggagaaa agtatcgatg tcaacctaaa ttatcaaatg    360

aagcttttag gagccgaaaa agaatccttt gattcaataa ttgcaactgg ttctaattcg    420

gcaatgccgc attgaagggc gagtgaaacc gaaattttag ataatgatct tttaaaaatt    480

gattttggtg cgctttttaa cggttattgc gctgatatta caagaacttc ttatcttgga    540

cagattagtg aaaaaaaatt agaaattttg gaaatagtaa aaaaagctgc tgaaattggt    600

agaaaaaaag ttgctcctgg ggttaaagcc agcgaaattg accttgcttg ccggaatttt    660

atcaccgaac aaggctatgg aaaatatttt attcactcaa ctggccacgg ggttggtatt    720

gatatccatg aattgccagt tgttagttca actagccaga caattttaga gcccggaatg    780

gtaataactg ttgaacccgg aatttatatc cctggacttg gaggcgcaag aattgaggat    840

gttgttttag taactgaaag tggttttcgt accttgtcac gaaaaggtga aagaatt       897


<210> SEQ ID NO 36
<211> LENGTH: 299
<212> TYPE: PRT
<213> ORGANISM: Artificial Sequence
<220> FEATURE:
<223> OTHER INFORMATION: Description of Artificial Sequence:Deduced
      protein sequence from clone pAD784

<400> SEQUENCE: 36

Ala Phe Leu Phe Val Asp Gly Arg Tyr Ile Glu Lys Ala Glu Lys Asp
  1               5                  10                  15

Ala Lys Asn Cys Gln Val Phe Leu Pro Thr Lys Gln Ile Leu Lys Ile
            20                  25                  30

Phe Ser Arg Lys Pro Val Ser Lys Asn Arg His Trp Ser Glu Tyr Leu
        35                  40                  45

Thr Ile Asp Gln Phe Asp Lys Ile Arg Ser Trp Phe Pro Asn Ala Asp
```

```
     50                  55                  60

Phe Val Lys Leu Gln Ala Gln Leu Phe Arg Ile Ile Lys Thr Glu Glu
 65                  70                  75                  80

Glu Ile Lys Asn Ile Glu Lys Ala Val Glu Ile Ser Leu Ala Ala Tyr
                 85                  90                  95

Asn Lys Ile Phe Pro Lys Ile Lys Pro Gly Met Thr Glu Lys Ser Ile
            100                 105                 110

Asp Val Asn Leu Asn Tyr Gln Met Lys Leu Leu Gly Ala Glu Lys Glu
        115                 120                 125

Ser Phe Asp Ser Ile Ile Ala Thr Gly Ser Asn Ser Ala Met Pro His
    130                 135                 140

Trp Arg Ala Ser Glu Thr Glu Ile Leu Asp Asn Asp Leu Leu Lys Ile
145                 150                 155                 160

Asp Phe Gly Ala Leu Phe Asn Gly Tyr Cys Ala Asp Ile Thr Arg Thr
                165                 170                 175

Ser Tyr Leu Gly Gln Ile Ser Glu Lys Lys Leu Glu Ile Leu Glu Ile
            180                 185                 190

Val Lys Lys Ala Ala Glu Ile Gly Arg Lys Lys Val Ala Pro Gly Val
        195                 200                 205

Lys Ala Ser Glu Ile Asp Leu Ala Cys Arg Asn Phe Ile Thr Glu Gln
    210                 215                 220

Gly Tyr Gly Lys Tyr Phe Ile His Ser Thr Gly His Gly Val Gly Ile
225                 230                 235                 240

Asp Ile His Glu Leu Pro Val Val Ser Ser Thr Ser Gln Thr Ile Leu
                245                 250                 255

Glu Pro Gly Met Val Ile Thr Val Glu Pro Gly Ile Tyr Ile Pro Gly
            260                 265                 270

Leu Gly Gly Ala Arg Ile Glu Asp Val Val Leu Val Thr Glu Ser Gly
        275                 280                 285

Phe Arg Thr Leu Ser Arg Lys Gly Glu Arg Ile
    290                 295
```

```
<210> SEQ ID NO 37
<211> LENGTH: 633
<212> TYPE: DNA
<213> ORGANISM: Artificial Sequence
<220> FEATURE:
<223> OTHER INFORMATION: Description of Artificial Sequence:Clone pAD789

<400> SEQUENCE: 37

gatcttgtat ttaaagtaga aaattctgaa aatcaattac aagatttaga tggaactttt      60

tctttaatta gtattaaaaa tttaaactat aaattggaag atagagtttt atttaataat     120

ttaaatttag aagttcaaaa aggtaaaaaa tatttactaa aaggagctaa cgggtctgga     180

aagtccacat tttcaaggat tttattaggc attgagaagg aatttgaagg tcaaatttta     240

ataaataaca aatacgatat aaaaaaaata aatcctgatt ctataaataa ccatattaat     300

tatgtataca acaattcaga cttaattaat gcatcaactc tagaaaatat ttcgcttttg     360

gaaccgaaaa caaaagatga gattaggccg ttattagaaa aggtaaattt tgaaaacctt     420

gatttagaca agaaaattga ttctgatgtt tgattatttt tccactgggc aaatccaaaa     480

aatccccttg cacgctcact ttattctcca aaagaaattt taataattga cgaaggtctt     540

tccaacttag accaagaaag ttatgttaaa atcatatctg aacttattgc ggataaaaat     600

ttaacattaa ttttcattac ccctcacttt gat                                  633
```

-continued

<210> SEQ ID NO 38
<211> LENGTH: 211
<212> TYPE: PRT
<213> ORGANISM: Artificial Sequence
<220> FEATURE:
<223> OTHER INFORMATION: Description of Artificial Sequence:Deduced protein sequence from clone pAD789

<400> SEQUENCE: 38

```
Asp Leu Val Phe Lys Val Glu Asn Ser Glu Asn Gln Leu Gln Asp Leu
  1               5                  10                  15

Asp Gly Thr Phe Ser Leu Ile Ser Ile Lys Asn Leu Asn Tyr Lys Leu
             20                  25                  30

Glu Asp Arg Val Leu Phe Asn Asn Leu Asn Leu Glu Val Gln Lys Gly
         35                  40                  45

Lys Lys Tyr Leu Leu Lys Gly Ala Asn Gly Ser Gly Lys Ser Thr Phe
     50                  55                  60

Ser Arg Ile Leu Leu Gly Ile Glu Lys Glu Phe Glu Gly Gln Ile Leu
 65                  70                  75                  80

Ile Asn Asn Lys Tyr Asp Ile Lys Lys Ile Asn Pro Asp Ser Ile Asn
                 85                  90                  95

Asn His Ile Asn Tyr Val Tyr Asn Asn Ser Asp Leu Ile Asn Ala Ser
            100                 105                 110

Thr Leu Glu Asn Ile Ser Leu Leu Glu Pro Lys Thr Lys Asp Glu Ile
        115                 120                 125

Arg Pro Leu Leu Glu Lys Val Asn Phe Glu Asn Leu Asp Leu Asp Lys
    130                 135                 140

Lys Ile Asp Ser Asp Val Trp Leu Phe Phe His Trp Ala Asn Pro Lys
145                 150                 155                 160

Asn Pro Leu Ala Arg Ser Leu Tyr Ser Pro Lys Glu Ile Leu Ile Ile
                165                 170                 175

Asp Glu Gly Leu Ser Asn Leu Asp Gln Glu Ser Tyr Val Lys Ile Ile
            180                 185                 190

Ser Glu Leu Ile Ala Asp Lys Asn Leu Thr Leu Ile Phe Ile Thr Pro
        195                 200                 205

His Phe Asp
    210
```

<210> SEQ ID NO 39
<211> LENGTH: 1791
<212> TYPE: DNA
<213> ORGANISM: Artificial Sequence
<220> FEATURE:
<223> OTHER INFORMATION: Description of Artificial Sequence:Clones pAD908, pAD981, pAD1013, and pAD1049

<400> SEQUENCE: 39

```
cttgaaataa tcaaatatgg atcaaaagaa tctctaaatt actgactaat ttctgaaagc     60

gggaaaagat atgactattt tcgaccaatt gaaggaattc ttaataaaat tcagagaaaa    120

ttttgggaga catcaagcga agatttacga ctttgattta agaaaatgat gtcagaattt    180

ccttgtagta gttgcaaagg agcccggctt aacaagtatg cgcttgccgt tttcattgaa    240

aagtataata tctttcaatt atcccaactt tcaattaaag atttaataac ttttttttaga   300

aatttaaaat taactgaatt tgacggaaaa atttctactt taattctcga tgaaattaaa    360

tcacgactgt catttttagc aaatgttggt cttgaatatt taactttaaa tagatcaacg    420

gcaaccttat caggaggcga atcccaacga attaggcttg caagccaggt tggatatcaa    480
```

-continued

```
ctaaccggaa ttctttatgt tcttgatgaa ccttcaattg gcctacatca aaaagataat    540

gacaaattaa ttgcgacact gaaaaaaatg gttgaaattg gtaatagttt aattgtagtc    600

gagcatgatt ttgagacaat tttagctgct gattatattg ttgatatcgg gccaaaagct    660

ggtgaaaacg gtggtttttt ggttgctgca ggatcaatta aggatattga aaatgaacca    720

aaatcactta ccggccaatt tttaactgga aaattggaaa ttccagtacc aaaaaaacga    780

cgggctggca atggcaaatt tataattatt gaaaaagctg ctgaaaataa tttaaaaaaa    840

attaatgtca acattcctct aggcaaattt gttgttgtca ctggtgtttc tggatctgga    900

aagtcgacat tagttaatca aattatcgta aatgcgattg ccaaaaatct tggaacaact    960

aatattcgca ttgggaaaaa tgtgaggaaa ttaaagggct ttttaatatt gataagttga   1020

ttgcaatcaa tcaaagtcaa tcggacgaac cctagatcaa atcccgcaac ttatacctct   1080

gtttttgatg atatccgtga ggtttttgcc aatactgagc aggcaagagc gcttggtttt   1140

tcaaagtcaa aattttcctt taatctgcaa actgggcggt gtgataaatg ccaaggagac   1200

gggcaaatta aaattgaaat gtattttatg cctgatattt atgttttatg tgatcactgc   1260

caaggaaaaa gatacaagcc ggatgtccta caaattcgtt tttatggaaa aacaatcgcg   1320

gatattcttg atttaacagt ttcagaagca cttgaatttt tccataattg gcctaaaata   1380

atcgcaaaat tacaaaccct agctgatgtt ggtcttggtt atataaaact tggccaatca   1440

gcaataactt tatcaggagg agaagctcaa cgaattaaat tagccacttt tttacaaaaa   1500

aaacctaaag gaaaatcact ttttgtactt gacgagccaa caactggact ccataattat   1560

gatgttgcta atttaattaa agtgctaaat cgaatagtcg ataacggtga tagcataatt   1620

gtaatcgagc ataatttaga ggtaattaaa gttgctgact atattattga tttaggccca   1680

aacggcgggg ataacggggg ccaaatagtt gcaaaaggaa caccagaagc tgtagcaaaa   1740

gttagtgaat catatactgg cgcttattta aaaacaattt taaatataaa a            1791
```

<210> SEQ ID NO 40
<211> LENGTH: 597
<212> TYPE: PRT
<213> ORGANISM: Artificial Sequence
<220> FEATURE:
<223> OTHER INFORMATION: Description of Artificial Sequence:Deduced protein sequence from clones pAD908, pAD981, pAD1013, and pAD1049

<400> SEQUENCE: 40

```
Leu Glu Ile Ile Lys Tyr Gly Ser Lys Glu Ser Leu Asn Tyr Trp Leu
  1               5                  10                  15

Ile Ser Glu Ser Gly Lys Arg Tyr Asp Tyr Phe Arg Pro Ile Glu Gly
             20                  25                  30

Ile Leu Asn Lys Ile Gln Arg Lys Phe Trp Glu Thr Ser Ser Glu Asp
         35                  40                  45

Leu Arg Leu Trp Phe Lys Lys Met Met Ser Glu Phe Pro Cys Ser Ser
     50                  55                  60

Cys Lys Gly Ala Arg Leu Asn Lys Tyr Ala Leu Ala Val Phe Ile Glu
 65                  70                  75                  80

Lys Tyr Asn Ile Phe Gln Leu Ser Gln Leu Ser Ile Lys Asp Leu Ile
                 85                  90                  95

Thr Phe Phe Arg Asn Leu Lys Leu Thr Glu Phe Asp Gly Lys Ile Ser
            100                 105                 110

Thr Leu Ile Leu Asp Glu Ile Lys Ser Arg Leu Ser Phe Leu Ala Asn
        115                 120                 125
```

-continued

```
Val Gly Leu Glu Tyr Leu Thr Leu Asn Arg Ser Thr Ala Thr Leu Ser
    130                 135                 140

Gly Gly Glu Ser Gln Arg Ile Arg Leu Ala Ser Gln Val Gly Tyr Gln
145                 150                 155                 160

Leu Thr Gly Ile Leu Tyr Val Leu Asp Glu Pro Ser Ile Gly Leu His
                165                 170                 175

Gln Lys Asp Asn Asp Lys Leu Ile Ala Thr Leu Lys Lys Met Val Glu
            180                 185                 190

Ile Gly Asn Ser Leu Ile Val Val Glu His Asp Phe Glu Thr Ile Leu
        195                 200                 205

Ala Ala Asp Tyr Ile Val Asp Ile Gly Pro Lys Ala Gly Glu Asn Gly
    210                 215                 220

Gly Phe Leu Val Ala Ala Gly Ser Ile Lys Asp Ile Glu Asn Glu Pro
225                 230                 235                 240

Lys Ser Leu Thr Gly Gln Phe Leu Thr Gly Lys Leu Glu Ile Pro Val
                245                 250                 255

Pro Lys Lys Arg Arg Ala Gly Asn Gly Lys Phe Ile Ile Ile Glu Lys
            260                 265                 270

Ala Ala Glu Asn Asn Leu Lys Lys Ile Asn Val Asn Ile Pro Leu Gly
        275                 280                 285

Lys Phe Val Val Val Thr Gly Val Ser Gly Ser Gly Lys Ser Thr Leu
    290                 295                 300

Val Asn Gln Ile Ile Val Asn Ala Ile Ala Lys Asn Leu Gly Thr Thr
305                 310                 315                 320

Asn Ile Arg Ile Gly Lys Asn Val Arg Lys Leu Lys Gly Phe Leu Ile
                325                 330                 335

Leu Ile Ser Trp Leu Gln Ser Ile Lys Val Asn Arg Thr Asn Pro Arg
            340                 345                 350

Ser Asn Pro Ala Thr Tyr Thr Ser Val Phe Asp Asp Ile Arg Glu Val
        355                 360                 365

Phe Ala Asn Thr Glu Gln Ala Arg Ala Leu Gly Phe Ser Lys Ser Lys
    370                 375                 380

Phe Ser Phe Asn Leu Gln Thr Gly Arg Cys Asp Lys Cys Gln Gly Asp
385                 390                 395                 400

Gly Gln Ile Lys Ile Glu Met Tyr Phe Met Pro Asp Ile Tyr Val Leu
                405                 410                 415

Cys Asp His Cys Gln Gly Lys Arg Tyr Lys Pro Asp Val Leu Gln Ile
            420                 425                 430

Arg Phe Tyr Gly Lys Thr Ile Ala Asp Ile Leu Asp Leu Thr Val Ser
        435                 440                 445

Glu Ala Leu Glu Phe Phe His Asn Trp Pro Lys Ile Ile Ala Lys Leu
    450                 455                 460

Gln Thr Leu Ala Asp Val Gly Leu Gly Tyr Ile Lys Leu Gly Gln Ser
465                 470                 475                 480

Ala Ile Thr Leu Ser Gly Gly Glu Ala Gln Arg Ile Lys Leu Ala Thr
                485                 490                 495

Phe Leu Gln Lys Lys Pro Lys Gly Lys Ser Leu Phe Val Leu Asp Glu
            500                 505                 510

Pro Thr Thr Gly Leu His Asn Tyr Asp Val Ala Asn Leu Ile Lys Val
        515                 520                 525

Leu Asn Arg Ile Val Asp Asn Gly Asp Ser Ile Ile Val Ile Glu His
    530                 535                 540
```

-continued

```
Asn Leu Glu Val Ile Lys Val Ala Asp Tyr Ile Ile Asp Leu Gly Pro
545                 550                 555                 560

Asn Gly Gly Asp Asn Gly Gly Gln Ile Val Ala Lys Gly Thr Pro Glu
                565                 570                 575

Ala Val Ala Lys Val Ser Glu Ser Tyr Thr Gly Ala Tyr Leu Lys Thr
            580                 585                 590

Ile Leu Asn Ile Lys
        595


<210> SEQ ID NO 41
<211> LENGTH: 900
<212> TYPE: DNA
<213> ORGANISM: Artificial Sequence
<220> FEATURE:
<223> OTHER INFORMATION: Description of Artificial Sequence:Clone pAD913

<400> SEQUENCE: 41

atgaaaatta aagcaaaaac catcgtaaaa atttatgatc aaaaattacc atcagaatta     60

aaagcccttg ataaagtaac tactgaaata aatcagggcg agtttattgc aataattggc    120

caaactggtt caggaaaaac aacttttatt cagcatatga atgcactttt gctaccagat    180

caaggcgaaa ttgagtatct ctattttgat tcaaaaaatc aagaaaaaaa attagttgtt    240

caaaaaccgc gtttttttag aaaaaaacta aaatttatta atgaaattcg tcggcgtgtg    300

ggcgtcgttt ttcagtttgc tgaatatcag ctttttgagc aaacaattga aaaagacatc    360

atatttgggg ctgtttcaat gggaactcca aaaaatgagg caaaaaaaat tgccgcagaa    420

ataattgaat tagttggtct tgatcaaagt tttttacaaa aatcaccttt tgaactttca    480

ggtggccaga aacgccgagt tgcaattgcc ggaattttag caatggatcc tgatattatt    540

ttttttgatg aacccacggc cggacttgat ccccaaggaa cgctaaaaat gcttgaaatt    600

cttgatactt tatataaaaa gggcaagaca atcattctgg caactcatga tcttgatagt    660

gttttagaat gaacaaaacg ttgtattttt tttaaagatg gtagaattat ttatgatggt    720

gatacttatt caattttagc aaataataaa tttttaattg aaaataagat gttaccaact    780

aatttactca attttcgcga aaaattaatc aaaattggtt atccaatttc taatgttaga    840

tcagtatctg agttaatcag tgaaattaat atgctaattc aaaaggaaac aaatgcagat    900


<210> SEQ ID NO 42
<211> LENGTH: 300
<212> TYPE: PRT
<213> ORGANISM: Artificial Sequence
<220> FEATURE:
<223> OTHER INFORMATION: Description of Artificial Sequence:Deduced
      protein sequence from clone pAD913

<400> SEQUENCE: 42

Met Lys Ile Lys Ala Lys Thr Ile Val Lys Ile Tyr Asp Gln Lys Leu
  1               5                  10                  15

Pro Ser Glu Leu Lys Ala Leu Asp Lys Val Thr Thr Glu Ile Asn Gln
             20                  25                  30

Gly Glu Phe Ile Ala Ile Ile Gly Gln Thr Gly Ser Gly Lys Thr Thr
         35                  40                  45

Phe Ile Gln His Met Asn Ala Leu Leu Leu Pro Asp Gln Gly Glu Ile
     50                  55                  60

Glu Tyr Leu Tyr Phe Asp Ser Lys Asn Gln Glu Lys Lys Leu Val Val
 65                  70                  75                  80

Gln Lys Pro Arg Phe Phe Arg Lys Lys Leu Lys Phe Ile Asn Glu Ile
```

-continued

```
                85                  90                  95

Arg Arg Arg Val Gly Val Val Phe Gln Phe Ala Glu Tyr Gln Leu Phe
            100                 105                 110

Glu Gln Thr Ile Glu Lys Asp Ile Ile Phe Gly Ala Val Ser Met Gly
        115                 120                 125

Thr Pro Lys Asn Glu Ala Lys Lys Ile Ala Ala Glu Ile Ile Glu Leu
    130                 135                 140

Val Gly Leu Asp Gln Ser Phe Leu Gln Lys Ser Pro Phe Glu Leu Ser
145                 150                 155                 160

Gly Gly Gln Lys Arg Arg Val Ala Ile Ala Gly Ile Leu Ala Met Asp
                165                 170                 175

Pro Asp Ile Ile Phe Phe Asp Glu Pro Thr Ala Gly Leu Asp Pro Gln
            180                 185                 190

Gly Thr Leu Lys Met Leu Glu Ile Leu Asp Thr Leu Tyr Lys Lys Gly
        195                 200                 205

Lys Thr Ile Ile Leu Ala Thr His Asp Leu Asp Ser Val Leu Glu Trp
    210                 215                 220

Thr Lys Arg Cys Ile Phe Phe Lys Asp Gly Arg Ile Ile Tyr Asp Gly
225                 230                 235                 240

Asp Thr Tyr Ser Ile Leu Ala Asn Asn Lys Phe Leu Ile Glu Asn Lys
                245                 250                 255

Met Leu Pro Thr Asn Leu Leu Asn Phe Arg Glu Lys Leu Ile Lys Ile
            260                 265                 270

Gly Tyr Pro Ile Ser Asn Val Arg Ser Val Ser Glu Leu Ile Ser Glu
        275                 280                 285

Ile Asn Met Leu Ile Gln Lys Glu Thr Asn Ala Asp
    290                 295                 300
```

<210> SEQ ID NO 43
<211> LENGTH: 489
<212> TYPE: DNA
<213> ORGANISM: Artificial Sequence
<220> FEATURE:
<223> OTHER INFORMATION: Description of Artificial Sequence:Deduced protein sequence from clone pAD920

<400> SEQUENCE: 43

```
ttaaaatccc gtttttatca aaaagtaaat tcgcagatag acgttaaaaa aaacacagat     60

caagaaaaag ataaaaaaac tgagcccgaa aaaattaatt tttatactct gaaaaaagta    120

atttttcctg aaagtttgct tgagattgat gattatgcct tttatgtcga tagtgcaaat    180

ttagatcaaa atgaaaaaat tcaagaactt gatttttcaa aagcaatgaa attaaggagg    240

attgggagtt tcgcttttca aggaaacaat ataaaaacgc tcgttttacc cccttctatt    300

acatcaattg gaaaacaagc ttttgcaaaa aacagtttag aaacagtaga tttttcccag    360

gcaacaaaac tagaaacaat tgaacctggt gccttttttg ataataaaat caccgaactt    420

gatttgtcaa aaaatttgat tttagccgaa attttcaggg tagttttgag acaaatcaaa    480

ttatcaagt                                                            489
```

<210> SEQ ID NO 44
<211> LENGTH: 163
<212> TYPE: PRT
<213> ORGANISM: Artificial Sequence
<220> FEATURE:
<223> OTHER INFORMATION: Description of Artificial Sequence:Deduced protein sequence from clone pAD920

-continued

<400> SEQUENCE: 44

```
Leu Lys Ser Arg Phe Tyr Gln Lys Val Asn Ser Gln Ile Asp Val Lys
  1               5                  10                  15

Lys Asn Thr Asp Gln Glu Lys Asp Lys Lys Thr Glu Pro Glu Lys Ile
             20                  25                  30

Asn Phe Tyr Thr Leu Lys Lys Val Ile Phe Pro Glu Ser Leu Leu Glu
         35                  40                  45

Ile Asp Asp Tyr Ala Phe Tyr Val Asp Ser Ala Asn Leu Asp Gln Asn
     50                  55                  60

Glu Lys Ile Gln Glu Leu Asp Phe Ser Lys Ala Met Lys Leu Arg Arg
 65                  70                  75                  80

Ile Gly Ser Phe Ala Phe Gln Gly Asn Asn Ile Lys Thr Leu Val Leu
                 85                  90                  95

Pro Pro Ser Ile Thr Ser Ile Gly Lys Gln Ala Phe Ala Lys Asn Ser
            100                 105                 110

Leu Glu Thr Val Asp Phe Ser Gln Ala Thr Lys Leu Glu Thr Ile Glu
        115                 120                 125

Pro Gly Ala Phe Phe Asp Asn Lys Ile Thr Glu Leu Asp Leu Ser Lys
    130                 135                 140

Asn Leu Ile Leu Ala Glu Ile Phe Arg Val Val Leu Arg Gln Ile Lys
145                 150                 155                 160

Leu Ser Ser
```

<210> SEQ ID NO 45
<211> LENGTH: 1101
<212> TYPE: DNA
<213> ORGANISM: Artificial Sequence
<220> FEATURE:
<223> OTHER INFORMATION: Description of Artificial Sequence:Clone pAD922

<400> SEQUENCE: 45

```
actgatcaga tcttaatttt ccatttggcc aaaactttag accaaaaata tcttgaaatt     60

gaccttgaaa tgctcgaaaa aggtaacttt gaatttcaag atttcattaa tttctggcaa    120

tctcggattg aaaaaataga agaaaattta gcgcaaattt ctaccgataa aatcacagag    180

gcaaaaatca acgaattttt taattcttat ttgctttatt ttgaaaaatt acaaaaatta    240

tttagctcat catataatct tggctatgaa aatgtggcca aattatatga ttatttctat    300

gaagtccaaa aaatttaccg acaaaaacag caagcaaaag tcgaatttga ctaccgcagt    360

gctaaaaaag attatgaaga ccagctaaaa aaaataaagc aagaaaaagc ttttttcatt    420

aaaacattaa atgtaaaagc gcttaattta aaaaaagagg cccaactcga gattgacaaa    480

ttcaccgctc aaaacaattt gttgacttcc tatattgacg aatttaatta tgaatataaa    540

attgcaaata acaaagcgct agtaacaaca gatctaaaaa attattcatt ttttaaaaaa    600

caagcaataa tcaataagga aattgccaaa tttcttgata ggagaaatat tttgttactt    660

gaaaaaaacc ttttttcctt tcttaatatt tctgagattg aaaaattatt tgaaattatg    720

aataatttca aaaaaagtca aattgaaaag tataaaagtt tgactttcga taaaaaagat    780

gaaaaaaatt atacaaatac aaaattattt agtcaattaa tccgtaccga aattatcatt    840

ttggatattc aaggtttaaa agaaattgcc caaaatcgta aaaaaactta tcaagaaaaa    900

gtaaattttc aaacaaaatt tctccaattt aaaaataaat attcatataa taaaaaaaga    960

agtagtccgc aagccgaaaa tctagaaaaa ctcaatgaat taaaagaaaa actggcccaa   1020

aaagaagcaa tttatgaaga agaaaaagac ctttttatta gaaaatatac ctcttggaaa   1080
```

```
acaaaaccag agcaaaaaaa t                                              1101


<210> SEQ ID NO 46
<211> LENGTH: 367
<212> TYPE: PRT
<213> ORGANISM: Artificial Sequence
<220> FEATURE:
<223> OTHER INFORMATION: Description of Artificial Sequence:Deduced
      protein sequence from clone pAD922

<400> SEQUENCE: 46

Thr Asp Gln Ile Leu Ile Phe His Leu Ala Lys Thr Leu Asp Gln Lys
  1               5                  10                  15

Tyr Leu Glu Ile Asp Leu Glu Met Leu Glu Lys Gly Asn Phe Glu Phe
             20                  25                  30

Gln Asp Phe Ile Asn Phe Trp Gln Ser Arg Ile Glu Lys Ile Glu Glu
         35                  40                  45

Asn Leu Ala Gln Ile Ser Thr Asp Lys Ile Thr Glu Ala Lys Ile Asn
     50                  55                  60

Glu Phe Phe Asn Ser Tyr Leu Leu Tyr Phe Glu Lys Leu Gln Lys Leu
 65                  70                  75                  80

Phe Ser Ser Ser Tyr Asn Leu Gly Tyr Glu Asn Val Ala Lys Leu Tyr
                 85                  90                  95

Asp Tyr Phe Tyr Glu Val Gln Lys Ile Tyr Arg Gln Lys Gln Gln Ala
            100                 105                 110

Lys Val Glu Phe Asp Tyr Arg Ser Ala Lys Lys Asp Tyr Glu Asp Gln
        115                 120                 125

Leu Lys Lys Ile Lys Gln Glu Lys Ala Phe Phe Ile Lys Thr Leu Asn
    130                 135                 140

Val Lys Ala Leu Asn Leu Lys Lys Glu Ala Gln Leu Glu Ile Asp Lys
145                 150                 155                 160

Phe Thr Ala Gln Asn Asn Leu Leu Thr Ser Tyr Ile Asp Glu Phe Asn
                165                 170                 175

Tyr Glu Tyr Lys Ile Ala Asn Asn Lys Ala Leu Val Thr Thr Asp Leu
            180                 185                 190

Lys Asn Tyr Ser Phe Phe Lys Lys Gln Ala Ile Ile Asn Lys Glu Ile
        195                 200                 205

Ala Lys Phe Leu Asp Arg Arg Asn Ile Leu Leu Leu Glu Lys Asn Leu
    210                 215                 220

Phe Ser Phe Leu Asn Ile Ser Glu Ile Glu Lys Leu Phe Glu Ile Met
225                 230                 235                 240

Asn Asn Phe Lys Lys Ser Gln Ile Glu Lys Tyr Lys Ser Leu Thr Phe
                245                 250                 255

Asp Lys Lys Asp Glu Lys Asn Tyr Thr Asn Thr Lys Leu Phe Ser Gln
            260                 265                 270

Leu Ile Arg Thr Glu Ile Ile Ile Leu Asp Ile Gln Gly Leu Lys Glu
        275                 280                 285

Ile Ala Gln Asn Arg Lys Lys Thr Tyr Gln Glu Lys Val Asn Phe Gln
    290                 295                 300

Thr Lys Phe Leu Gln Phe Lys Asn Lys Tyr Ser Tyr Asn Lys Lys Arg
305                 310                 315                 320

Ser Ser Pro Gln Ala Glu Asn Leu Glu Lys Leu Asn Glu Leu Lys Glu
                325                 330                 335

Lys Leu Ala Gln Lys Glu Ala Ile Tyr Glu Glu Glu Lys Asp Leu Phe
            340                 345                 350
```

-continued

```
Ile Arg Lys Tyr Thr Ser Trp Lys Thr Lys Pro Glu Gln Lys Asn
        355                 360                 365


<210> SEQ ID NO 47
<211> LENGTH: 438
<212> TYPE: DNA
<213> ORGANISM: Artificial Sequence
<220> FEATURE:
<223> OTHER INFORMATION: Description of Artificial Sequence:Clones
      pAD923 and pAD925

<400> SEQUENCE: 47

tataatttaa aaaaagaaac taatttgagg aaatttttaa tgtcaaaaaa atctaaaaat      60

tcaagcattg aatttgatgc tattgttgtc ggtggcggcc atgctgggat cgaagcagtt     120

tatgcattat taaaaaaaaa gttaaaagtt gttctaataa ctcttgataa gaaaaaatta     180

gcttcaatgc cttgtaatcc cgcaattggt gggccagcaa aaggaattat aactcgcgag     240

atcgatgccc ttggaggagt tcagggaaaa ttttcagatt tagcaatgat ccaaattaaa     300

tatttaaatg aatcaaaagg tcctgccgtt ttagcaatta gagcccaaat tgataaggaa     360

aaatattcaa aattaatatt aaaggatttg aaaaaacagg aaaatttatt aattatcgag     420

gatttggtta gtgaactc                                                   438


<210> SEQ ID NO 48
<211> LENGTH: 146
<212> TYPE: PRT
<213> ORGANISM: Artificial Sequence
<220> FEATURE:
<223> OTHER INFORMATION: Description of Artificial Sequence:Deduced
      protein sequence from clones pAD923 and pAD925

<400> SEQUENCE: 48

Tyr Asn Leu Lys Lys Glu Thr Asn Leu Arg Lys Phe Leu Met Ser Lys
  1               5                  10                  15

Lys Ser Lys Asn Ser Ser Ile Glu Phe Asp Ala Ile Val Val Gly Gly
             20                  25                  30

Gly His Ala Gly Ile Glu Ala Val Tyr Ala Leu Leu Lys Lys Lys Leu
         35                  40                  45

Lys Val Val Leu Ile Thr Leu Asp Lys Lys Lys Leu Ala Ser Met Pro
     50                  55                  60

Cys Asn Pro Ala Ile Gly Gly Pro Ala Lys Gly Ile Ile Thr Arg Glu
 65                  70                  75                  80

Ile Asp Ala Leu Gly Gly Val Gln Gly Lys Phe Ser Asp Leu Ala Met
                 85                  90                  95

Ile Gln Ile Lys Tyr Leu Asn Glu Ser Lys Gly Pro Ala Val Leu Ala
            100                 105                 110

Ile Arg Ala Gln Ile Asp Lys Glu Lys Tyr Ser Lys Leu Ile Leu Lys
        115                 120                 125

Asp Leu Lys Lys Gln Glu Asn Leu Leu Ile Ile Glu Asp Leu Val Ser
    130                 135                 140

Glu Leu
145


<210> SEQ ID NO 49
<211> LENGTH: 1074
<212> TYPE: DNA
<213> ORGANISM: Artificial Sequence
<220> FEATURE:
<223> OTHER INFORMATION: Description of Artificial Sequence:Clone pAD950
```

-continued

<400> SEQUENCE: 49

```
caaattgtac aatcagaacc agaaatttta aatcaaaaat tttttttatg taaaaaaata     60
ctacaggaac aaaaattaat tagtttttgc gaacaaaaat tagaaaaagc aaagaaaaat    120
aaccaatttg aactcgccaa cgaatatcac aaagcgctta ttgcactgaa aaaaactaaa    180
attgaacaac aaaatattga gcttaacaac ctaaaaaata ttgattttct ttattatagt    240
gaaattggcg agaataattt agtaattagt tttgcttttt atcgcaatgg tgttttttta    300
tctaataaaa attttattat tgatattata cttaattata cagaagtttt aattaatttt    360
ttaaataatt attataaaat taatatttat cccgatgagt tagtagttaa aaatttttgg    420
cctaaaaatg ctgaattttt agacccaaaa attaatatca aaattggaaa aagcttaaaa    480
tataagcata ttttaaacac tttagcaaaa aatcaccaag attttatcag ccataatttt    540
gaccaagaaa ttaagaaaaa aattaaaaat cagaaaattt tagaactagt taaaaccagt    600
ttaaaaattg aaaatgttga aaaaattatg gcaattgact gctcaaattt agagtcaaac    660
taccccacaa ctggaattat tttctatata aacggaatat atgagcgaaa ttacaataga    720
tttttcaatt ataggggaac aaaaaaaggt gatacaaatt atatgagaca gggttttgaa    780
aaatatatta aaaatccaaa atttctaaaa cctgatttga ttttagtaga tggaggaatt    840
caacaaatta atttaattat agaaatttta agaaaaaatc actttgaaat tccgattttt    900
ggaatggtaa aaaataaaag gcataaaact gaaaaaatta ttgacttaaa tggtaaaaaa    960
attaacctag ctcaagaagt tcttaatttc tttgctttaa ttcaagaaaa tgtcgattta   1020
tttgttaagg aaaaaatgaa gaaaaaacaa ataaaaagtt tattttctaa ggaa         1074
```

<210> SEQ ID NO 50
<211> LENGTH: 358
<212> TYPE: PRT
<213> ORGANISM: Artificial Sequence
<220> FEATURE:
<223> OTHER INFORMATION: Description of Artificial Sequenc:Deduced protein sequence from Clone pAD950

<400> SEQUENCE: 50

```
Gln Ile Val Gln Ser Glu Pro Glu Ile Leu Asn Gln Lys Phe Phe Leu
  1               5                  10                  15

Cys Lys Lys Ile Leu Gln Glu Gln Lys Leu Ile Ser Phe Cys Glu Gln
             20                  25                  30

Lys Leu Glu Lys Ala Lys Lys Asn Asn Gln Phe Glu Leu Ala Asn Glu
         35                  40                  45

Tyr His Lys Ala Leu Ile Ala Leu Lys Lys Thr Lys Ile Glu Gln Gln
     50                  55                  60

Asn Ile Glu Leu Asn Asn Leu Lys Asn Ile Asp Phe Leu Tyr Tyr Ser
 65                  70                  75                  80

Glu Ile Gly Glu Asn Asn Leu Val Ile Ser Phe Ala Phe Tyr Arg Asn
                 85                  90                  95

Gly Val Phe Leu Ser Asn Lys Asn Phe Ile Ile Asp Ile Ile Leu Asn
            100                 105                 110

Tyr Thr Glu Val Leu Ile Asn Phe Leu Asn Asn Tyr Tyr Lys Ile Asn
        115                 120                 125

Ile Tyr Pro Asp Glu Leu Val Val Lys Asn Phe Trp Pro Lys Asn Ala
    130                 135                 140

Glu Phe Leu Asp Pro Lys Ile Asn Ile Lys Ile Gly Lys Ser Leu Lys
145                 150                 155                 160
```

-continued

```
Tyr Lys His Ile Leu Asn Thr Leu Ala Lys Asn His Gln Asp Phe Ile
                165                 170                 175

Ser His Asn Phe Asp Gln Glu Ile Lys Lys Lys Ile Lys Asn Gln Lys
            180                 185                 190

Ile Leu Glu Leu Val Lys Thr Ser Leu Lys Ile Glu Asn Val Glu Lys
        195                 200                 205

Ile Met Ala Ile Asp Cys Ser Asn Leu Glu Ser Asn Tyr Pro Thr Thr
    210                 215                 220

Gly Ile Ile Phe Tyr Ile Asn Gly Ile Tyr Glu Arg Asn Tyr Asn Arg
225                 230                 235                 240

Phe Phe Asn Tyr Arg Gly Thr Lys Lys Gly Asp Thr Asn Tyr Met Arg
                245                 250                 255

Gln Gly Phe Glu Lys Tyr Ile Lys Asn Pro Lys Phe Leu Lys Pro Asp
            260                 265                 270

Leu Ile Leu Val Asp Gly Gly Ile Gln Gln Ile Asn Leu Ile Ile Glu
        275                 280                 285

Ile Leu Arg Lys Asn His Phe Glu Ile Pro Ile Phe Gly Met Val Lys
    290                 295                 300

Asn Lys Arg His Lys Thr Glu Lys Ile Ile Asp Leu Asn Gly Lys Lys
305                 310                 315                 320

Ile Asn Leu Ala Gln Glu Val Leu Asn Phe Phe Ala Leu Ile Gln Glu
                325                 330                 335

Asn Val Asp Leu Phe Val Lys Glu Lys Met Lys Lys Lys Gln Ile Lys
            340                 345                 350

Ser Leu Phe Ser Lys Glu
        355
```

<210> SEQ ID NO 51
<211> LENGTH: 282
<212> TYPE: DNA
<213> ORGANISM: Artificial Sequence
<220> FEATURE:
<223> OTHER INFORMATION: Description of Artificial Sequence:Clone pAD951

<400> SEQUENCE: 51

```
tcgaatataa ctgacaaaac aggaaaactt ttaaaaattt ctaacaataa aaatacttta     60

atttttaaag ttgttggagt ttttgatcct gaaaaagatg acgaaaatat tgctattttt    120

aacaataata ttgaaaaata ttctagtgaa ttacttccaa tagctgctgt ggtttatttt    180

gatcatgata atttatataa taatattaat gaatttttaa ataaatatag caaaccgggc    240

gttagtcgtt attactcgac aaatggcggc cggatcaaat tc                       282
```

<210> SEQ ID NO 52
<211> LENGTH: 94
<212> TYPE: PRT
<213> ORGANISM: Artificial Sequence
<220> FEATURE:
<223> OTHER INFORMATION: Description of Artificial Sequence:Deduced protein sequence from clone pAD951

<400> SEQUENCE: 52

```
Ser Asn Ile Thr Asp Lys Thr Gly Lys Leu Leu Lys Ile Ser Asn Asn
  1               5                  10                  15

Lys Asn Thr Leu Ile Phe Lys Val Val Gly Val Phe Asp Pro Glu Lys
            20                  25                  30

Asp Asp Glu Asn Ile Ala Ile Phe Asn Asn Asn Ile Glu Lys Tyr Ser
        35                  40                  45
```

-continued

```
Ser Glu Leu Leu Pro Ile Ala Ala Val Val Tyr Phe Asp His Asp Asn
     50                  55                  60

Leu Tyr Asn Asn Ile Asn Glu Phe Leu Asn Lys Tyr Ser Lys Pro Gly
 65                  70                  75                  80

Val Ser Arg Tyr Tyr Ser Thr Asn Gly Gly Arg Ile Lys Phe
                 85                  90


<210> SEQ ID NO 53
<211> LENGTH: 438
<212> TYPE: DNA
<213> ORGANISM: Artificial Sequence
<220> FEATURE:
<223> OTHER INFORMATION: Description of Artificial Sequence:Clone pAD977

<400> SEQUENCE: 53

attttaatta ataattcaat tgaatataag gaattagacc caaaccagtt aagaaaacat     60

attgcactaa caacaaatga aaacataatt ttcgaagaca ctttggcaaa caacataact    120

ttatgagata aaaatcccga tttagatttg ctaaattctt taataaaaaa gtataaaatt    180

gataattttt caaaaccaga aactgaaatt agctcaaaaa atttatctga gggcgaaaaa    240

caaaaagttg cattggccag attagagtac aaaaatttag atatttgatg tttagatgaa    300

gctcttgata acattttcaa ggaagatgct tttgaaattt acagtgattt actttcaaaa    360

ccgaataaaa caatttttat cgcaagtcac cacattcctg aaaaaataaa accgatgttt    420

gaccaaataa ttgaaatt                                                  438


<210> SEQ ID NO 54
<211> LENGTH: 146
<212> TYPE: PRT
<213> ORGANISM: Artificial Sequence
<220> FEATURE:
<223> OTHER INFORMATION: Description of Artificial Sequence:Deduced
      protein sequence from clone pAD977

<400> SEQUENCE: 54

Ile Leu Ile Asn Asn Ser Ile Glu Tyr Lys Glu Leu Asp Pro Asn Gln
  1               5                  10                  15

Leu Arg Lys His Ile Ala Leu Thr Thr Asn Glu Asn Ile Ile Phe Glu
             20                  25                  30

Asp Thr Leu Ala Asn Asn Ile Thr Leu Trp Asp Lys Asn Pro Asp Leu
         35                  40                  45

Asp Leu Leu Asn Ser Leu Ile Lys Lys Tyr Lys Ile Asp Asn Phe Ser
     50                  55                  60

Lys Pro Glu Thr Glu Ile Ser Ser Lys Asn Leu Ser Glu Gly Glu Lys
 65                  70                  75                  80

Gln Lys Val Ala Leu Ala Arg Leu Glu Tyr Lys Asn Leu Asp Ile Trp
                 85                  90                  95

Cys Leu Asp Glu Ala Leu Asp Asn Ile Phe Lys Glu Asp Ala Phe Glu
            100                 105                 110

Ile Tyr Ser Asp Leu Leu Ser Lys Pro Asn Lys Thr Ile Phe Ile Ala
        115                 120                 125

Ser His His Ile Pro Glu Lys Ile Lys Pro Met Phe Asp Gln Ile Ile
    130                 135                 140

Glu Ile
145


<210> SEQ ID NO 55
```

-continued

<211> LENGTH: 400
<212> TYPE: DNA
<213> ORGANISM: Artificial Sequence
<220> FEATURE:
<223> OTHER INFORMATION: Description of Artificial Sequence:Clone pAD983

<400> SEQUENCE: 55

```
tcaacgggct gccaaattga acctgacaaa ccgctggtaa aaaaatgggt tatgggtgtt     60

ttatttaatt atagctttta ttattcagga attctaagca tagttttagg attttttttct   120

tctgaaataa caattttctt tcttcaaaca gcaggggctg atattaatgt tccagtttga   180

ggccatctaa taattgggac agtttttgt atttttttca ctagccttaa ttatatttca    240

ataaaaacat caggatgaat tgcgcttgca tcaacaattt taaaatttat tcctttagta   300

tttgcagttt ttgcaggaat tctatttcca aaaacttata atgccggcgg ttctaatgcc   360

tttgttcaaa cagctcaaat agttttaatt ttgcaaaatt                         400
```

<210> SEQ ID NO 56
<211> LENGTH: 133
<212> TYPE: PRT
<213> ORGANISM: Artificial Sequence
<220> FEATURE:
<223> OTHER INFORMATION: Description of Artificial Sequence:Deduced protein sequence from clone pAD983

<400> SEQUENCE: 56

```
Ser Thr Gly Cys Gln Ile Glu Pro Asp Lys Pro Leu Val Lys Lys Trp
  1               5                  10                  15

Val Met Gly Val Leu Phe Asn Tyr Ser Phe Tyr Tyr Ser Gly Ile Leu
             20                  25                  30

Ser Ile Val Leu Gly Phe Phe Ser Ser Glu Ile Thr Ile Phe Phe Leu
         35                  40                  45

Gln Thr Ala Gly Ala Asp Ile Asn Val Pro Val Trp Gly His Leu Ile
     50                  55                  60

Ile Gly Thr Val Phe Cys Ile Phe Phe Thr Ser Leu Asn Tyr Ile Ser
 65                  70                  75                  80

Ile Lys Thr Ser Gly Trp Ile Ala Leu Ala Ser Thr Ile Leu Lys Phe
                 85                  90                  95

Ile Pro Leu Val Phe Ala Val Phe Ala Gly Ile Leu Phe Pro Lys Thr
            100                 105                 110

Tyr Asn Ala Gly Gly Ser Asn Ala Phe Val Gln Thr Ala Gln Ile Val
        115                 120                 125

Leu Ile Leu Gln Asn
    130
```

<210> SEQ ID NO 57
<211> LENGTH: 522
<212> TYPE: DNA
<213> ORGANISM: Artificial Sequence
<220> FEATURE:
<223> OTHER INFORMATION: Description of Artificial Sequence:Clone pAD984

<400> SEQUENCE: 57

```
ttaaaaagtg aaaaccaaaa agaaacagca aatttaaata ctacttttac tcaaacaatt     60

agtaaaaaag atatcgaaat aaccaattta agaaatgaaa ttggcaaatt tcttgatgaa   120

aaagataaaa tgcgaagtga cattcttgca aatgatgatg agataaaggc gatgaggagt   180

gaaatttctc aactaaaaga agcaaatgcc aacctacaaa atgtcaagtt agaagaaatt   240

tcaaatttaa aactagaaca taaggacgaa attaatgaaa aagaccgtaa aattagttat   300
```

-continued

```
ttagagaata aatttaacga cttggaagaa gaaaaaaata attcaattca aaatgctgta    360

agtcaaaaaa cacgagaaat aaaggaaaaa attgaaaaag agctagaaat taaatgggga    420

agaaaaaata aaacaggaaa aatcagattt aagaggaaaa ttttaaggag caaattaata    480

aaccaggaga aaaaattcaa gattagaaga agaattaaat ta                       522
```

<210> SEQ ID NO 58
<211> LENGTH: 174
<212> TYPE: PRT
<213> ORGANISM: Artificial Sequence
<220> FEATURE:
<223> OTHER INFORMATION: Description of Artificial Sequence:Deduced protein sequence from clone pAD984

<400> SEQUENCE: 58

```
Leu Lys Ser Glu Asn Gln Lys Glu Thr Ala Asn Leu Asn Thr Thr Phe
  1               5                  10                  15

Thr Gln Thr Ile Ser Lys Lys Asp Ile Glu Ile Thr Asn Leu Arg Asn
             20                  25                  30

Glu Ile Gly Lys Phe Leu Asp Glu Lys Asp Lys Met Arg Ser Asp Ile
         35                  40                  45

Leu Ala Asn Asp Asp Glu Ile Lys Ala Met Arg Ser Glu Ile Ser Gln
     50                  55                  60

Leu Lys Glu Ala Asn Ala Asn Leu Gln Asn Val Lys Leu Glu Glu Ile
 65                  70                  75                  80

Ser Asn Leu Lys Leu Glu His Lys Asp Glu Ile Asn Glu Lys Asp Arg
                 85                  90                  95

Lys Ile Ser Tyr Leu Glu Asn Lys Phe Asn Asp Leu Glu Glu Glu Lys
            100                 105                 110

Asn Asn Ser Ile Gln Asn Ala Val Ser Gln Lys Thr Arg Glu Ile Lys
        115                 120                 125

Glu Lys Ile Glu Lys Glu Leu Glu Ile Lys Trp Gly Arg Lys Asn Lys
    130                 135                 140

Thr Gly Lys Ile Arg Phe Lys Arg Lys Ile Leu Arg Ser Lys Leu Ile
145                 150                 155                 160

Asn Gln Glu Lys Lys Phe Lys Ile Arg Arg Arg Ile Lys Leu
                165                 170
```

<210> SEQ ID NO 59
<211> LENGTH: 633
<212> TYPE: DNA
<213> ORGANISM: Artificial Sequence
<220> FEATURE:
<223> OTHER INFORMATION: Description of Artificial Sequence:Clone pAD994

<400> SEQUENCE: 59

```
attaaacact tttttaaaag atttgaaatg tataaacgat tagttcagga attctttcct     60

aaattagatt ttgaaaattt agaaaaatac gtaaatttaa ttgaatttag taataaaaac    120

tttaatttaa ccgctttttc tggtgatatt ctttgaaaag agggaatttt tgagtcaatt    180

tttacaatga atttcattgt tggtttagta aataataaag aaaataaaaa attaaaaatt    240

ttggatattg gggctggatc aggttttcct tcaattcctt ttttgattac aaacccagaa    300

attgagctaa caatttctga gtcaatgcaa aaaagatgcc agtttttaaa ggatgtttct    360

gaaaaattag atttgaaatt caatttaatt tgcaaaccag ttcaagaaat taatccacaa    420

aaatttgata taataactgc cagagcagtg gcaaatttgg aaaagcttga gaaaattaca    480
```

-continued

```
aaaaaaattc attttccaaa aacgctttta gcttttatta aagggcccaa agtttttaat    540

gaagttcaaa attgtaaaaa ttgtaattat aaaatcatta aagttaataa taatataaat    600

aaaaaaattt ttatcgcatt taaacaagtt tct                                 633
```

<210> SEQ ID NO 60
<211> LENGTH: 211
<212> TYPE: PRT
<213> ORGANISM: Artificial Sequence
<220> FEATURE:
<223> OTHER INFORMATION: Description of Artificial Sequence:Deduced protein sequence from clone pAD994

<400> SEQUENCE: 60

```
Ile Lys His Phe Phe Lys Arg Phe Glu Met Tyr Lys Arg Leu Val Gln
  1               5                  10                  15

Glu Phe Phe Pro Lys Leu Asp Phe Glu Asn Leu Glu Lys Tyr Val Asn
             20                  25                  30

Leu Ile Glu Phe Ser Asn Lys Asn Phe Asn Leu Thr Ala Phe Ser Gly
         35                  40                  45

Asp Ile Leu Trp Lys Glu Gly Ile Phe Glu Ser Ile Phe Thr Met Asn
     50                  55                  60

Phe Ile Val Gly Leu Val Asn Asn Lys Glu Asn Lys Lys Leu Lys Ile
 65                  70                  75                  80

Leu Asp Ile Gly Ala Gly Ser Gly Phe Pro Ser Ile Pro Phe Leu Ile
                 85                  90                  95

Thr Asn Pro Glu Ile Glu Leu Thr Ile Ser Glu Ser Met Gln Lys Arg
            100                 105                 110

Cys Gln Phe Leu Lys Asp Val Ser Glu Lys Leu Asp Leu Lys Phe Asn
        115                 120                 125

Leu Ile Cys Lys Pro Val Gln Glu Ile Asn Pro Gln Lys Phe Asp Ile
    130                 135                 140

Ile Thr Ala Arg Ala Val Ala Asn Leu Glu Lys Leu Glu Lys Ile Thr
145                 150                 155                 160

Lys Lys Ile His Phe Pro Lys Thr Leu Leu Ala Phe Ile Lys Gly Pro
                165                 170                 175

Lys Val Phe Asn Glu Val Gln Asn Cys Lys Asn Cys Asn Tyr Lys Ile
            180                 185                 190

Ile Lys Val Asn Asn Asn Ile Asn Lys Lys Ile Phe Ile Ala Phe Lys
        195                 200                 205

Gln Val Ser
    210
```

<210> SEQ ID NO 61
<211> LENGTH: 537
<212> TYPE: DNA
<213> ORGANISM: Artificial Sequence
<220> FEATURE:
<223> OTHER INFORMATION: Description of Artificial Sequence:Clone pAD1005

<400> SEQUENCE: 61

```
atgaaaaaat tattagttat tttgcttgat aaattccagg atattgaact tacaactttt     60

atttccctga ttaaaaaagc agaaattttt acagatattg aattttttaa ccctaaaaat    120

aataaattag taataggtca attcggagtt gtatcaattc aagcacataa tcactggaaa    180

tcagatgact ttgatgctgt ttttattccg gggggttttg cggcccaatt attccgcaag    240

gattcaaaat caattcaact tgtgagcgag ttttttgcgc aaaacaaaca tatttttgcc    300
```

-continued

```
atttgtgatg caccaaatgc aatttttgaa ctaaaattag cagaaaatta tcaatttagt    360

tcatatccaa accaacataa ttccaaaatt agactaagac aagattcgtt agtaactatt    420

gaccgcaatt atatttcggc aagaaatgca gcaagttcgg cagattttgc tttcgttgta    480

attgaaaagc tgggatcaaa agagttagct caaaaaatta gaaatggatt ttatctt       537
```

<210> SEQ ID NO 62
<211> LENGTH: 179
<212> TYPE: PRT
<213> ORGANISM: Artificial Sequence
<220> FEATURE:
<223> OTHER INFORMATION: Description of Artificial Sequence:Deduced protein sequence from clone pAD1005

<400> SEQUENCE: 62

```
Met Lys Lys Leu Leu Val Ile Leu Leu Asp Lys Phe Gln Asp Ile Glu
  1               5                  10                  15

Leu Thr Thr Phe Ile Ser Leu Ile Lys Lys Ala Glu Ile Phe Thr Asp
             20                  25                  30

Ile Glu Phe Phe Asn Pro Lys Asn Asn Lys Leu Val Ile Gly Gln Phe
         35                  40                  45

Gly Val Val Ser Ile Gln Ala His Asn His Trp Lys Ser Asp Asp Phe
     50                  55                  60

Asp Ala Val Phe Ile Pro Gly Gly Phe Ala Ala Gln Leu Phe Arg Lys
 65                  70                  75                  80

Asp Ser Lys Ser Ile Gln Leu Val Ser Glu Phe Phe Ala Gln Asn Lys
                 85                  90                  95

His Ile Phe Ala Ile Cys Asp Ala Pro Asn Ala Ile Phe Glu Leu Lys
            100                 105                 110

Leu Ala Glu Asn Tyr Gln Phe Ser Ser Tyr Pro Asn Gln His Asn Ser
        115                 120                 125

Lys Ile Arg Leu Arg Gln Asp Ser Leu Val Thr Ile Asp Arg Asn Tyr
    130                 135                 140

Ile Ser Ala Arg Asn Ala Ala Ser Ser Ala Asp Phe Ala Phe Val Val
145                 150                 155                 160

Ile Glu Lys Leu Gly Ser Lys Glu Leu Ala Gln Lys Ile Arg Asn Gly
                165                 170                 175

Phe Tyr Leu
```

<210> SEQ ID NO 63
<211> LENGTH: 486
<212> TYPE: DNA
<213> ORGANISM: Artificial Sequence
<220> FEATURE:
<223> OTHER INFORMATION: Description of Artificial Sequence:Clone pAD1016

<400> SEQUENCE: 63

```
ttaatcgttt ttgcttatat gatgttggtt gtaatgaatt gaggttttgc ctctgccgga     60

cttaacggta aagcgggaat aagtggttat ttaggtcact tttttccaaa tgctaatgaa    120

gccccaggaa ccgttgtaaa tcaagcagtt aactggggta tcacaattgg tcgtggaatt    180

ggatcagttc ttgttggttg attaattgtg aaaatttcgc ataaatatac agtaattttg    240

tctttatttt ttatgctttt tggaattatt gccccttatt caccaactta tgccgggttt    300

ataattctta gaacaatttt tgcaattggc ggaacaatgc agattatttt aattcaacca    360

gttgtctcaa attatttaaa tcaaaggcaa aaagctgtta tttcacaagt tttccccttt    420
```

-continued tttttatcca attggaacaa taattacgct tattcctttt gcaggaatta tttggtcaag 480
agctca 486

<210> SEQ ID NO 64
<211> LENGTH: 162
<212> TYPE: PRT
<213> ORGANISM: Artificial Sequence
<220> FEATURE:
<223> OTHER INFORMATION: Description of Artificial Sequence:Deduced protein sequence from clone pAD1016

<400> SEQUENCE: 64

```
Leu Ile Val Phe Ala Tyr Met Met Leu Val Val Met Asn Trp Gly Phe
  1               5                  10                  15

Ala Ser Ala Gly Leu Asn Gly Lys Ala Gly Ile Ser Gly Tyr Leu Gly
             20                  25                  30

His Phe Phe Pro Asn Ala Asn Glu Ala Pro Gly Thr Val Val Asn Gln
         35                  40                  45

Ala Val Asn Trp Gly Ile Thr Ile Gly Arg Gly Ile Gly Ser Val Leu
     50                  55                  60

Val Gly Trp Leu Ile Val Lys Ile Ser His Lys Tyr Thr Val Ile Leu
 65                  70                  75                  80

Ser Leu Phe Phe Met Leu Phe Gly Ile Ile Ala Pro Tyr Ser Pro Thr
                 85                  90                  95

Tyr Ala Gly Phe Ile Ile Leu Arg Thr Ile Phe Ala Ile Gly Gly Thr
            100                 105                 110

Met Gln Ile Ile Leu Ile Gln Pro Val Val Ser Asn Tyr Leu Asn Gln
        115                 120                 125

Arg Gln Lys Ala Val Ile Ser Gln Val Phe Pro Phe Phe Leu Ser Asn
    130                 135                 140

Trp Asn Asn Asn Tyr Ala Tyr Ser Phe Cys Arg Asn Tyr Leu Val Lys
145                 150                 155                 160

Ser Ser
```

<210> SEQ ID NO 65
<211> LENGTH: 456
<212> TYPE: DNA
<213> ORGANISM: Artificial Sequence
<220> FEATURE:
<223> OTHER INFORMATION: Description of Artificial Sequence:Clone pAD1020

<400> SEQUENCE: 65

```
tctgatcgtt ttccagttac aagtttagaa aaattatttc aatttgtcgc taattcagcg     60

cctatttttg aaaaattcaa aaaagcaaaa gaaaaatttt atcaagcaaa atttgggact    120

aagatgaata gttgagaccg tttagttcca ttagttgaga caaaaaataa ttattctgtt    180

gaagatgcac aaaaaatagt gcttggggca atcaaaccat taggtcaaga atataaagat    240

gttgtagaaa aagcatttag ccaaagatga attgactatc attatgttga ttcaaaaaga    300

tctggtgctt attcaattgg gggttcatat gggcttgaaa aaaaatatat tttaatgaat    360

tatgacttta ctataaacgc agttcatact ttagcacatg aattaggtca ttcgctccat    420

tcttattatt ctgataaaaa ccagaattat cataat                              456
```

<210> SEQ ID NO 66
<211> LENGTH: 152
<212> TYPE: PRT

<213> ORGANISM: Artificial Sequence
<220> FEATURE:
<223> OTHER INFORMATION: Description of Artificial Sequence:Deduced protein sequence from clone pAD1020

<400> SEQUENCE: 66

```
Ser Asp Arg Phe Pro Val Thr Ser Leu Glu Lys Leu Phe Gln Phe Val
  1               5                  10                  15

Ala Asn Ser Ala Pro Ile Phe Glu Lys Phe Lys Lys Ala Lys Glu Lys
             20                  25                  30

Phe Tyr Gln Ala Lys Phe Gly Thr Lys Met Asn Ser Trp Asp Arg Leu
         35                  40                  45

Val Pro Leu Val Glu Thr Lys Asn Asn Tyr Ser Val Glu Asp Ala Gln
     50                  55                  60

Lys Ile Val Leu Gly Ala Ile Lys Pro Leu Gly Gln Glu Tyr Lys Asp
 65                  70                  75                  80

Val Val Glu Lys Ala Phe Ser Gln Arg Trp Ile Asp Tyr His Tyr Val
                 85                  90                  95

Asp Ser Lys Arg Ser Gly Ala Tyr Ser Ile Gly Gly Ser Tyr Gly Leu
            100                 105                 110

Glu Lys Lys Tyr Ile Leu Met Asn Tyr Asp Phe Thr Ile Asn Ala Val
        115                 120                 125

His Thr Leu Ala His Glu Leu Gly His Ser Leu His Ser Tyr Tyr Ser
    130                 135                 140

Asp Lys Asn Gln Asn Tyr His Asn
145                 150
```

<210> SEQ ID NO 67
<211> LENGTH: 576
<212> TYPE: DNA
<213> ORGANISM: Artificial Sequence
<220> FEATURE:
<223> OTHER INFORMATION: Description of Artificial Sequence:Clone pAD1027

<400> SEQUENCE: 67

```
gaattaatta gggaaaattt atcacttgca aaatcatttt atgttgataa aaataataat     60

ccttggatat caacaacaaa aaattttgaa aacttatttg attatgtaca aagcgagcat    120

ctaattaata ctaataaaat aaaaaattat atcacaaaca taaattttaa aatcaaaaaa    180

aatagtgaaa tacctgcttt agaacttaat aatttgctaa aagatgataa aattcggctt    240

gaaataaatg ttgatatctc aaagtgagtc caacaaaaac taattaaaat tttaagtttt    300

aagtttgatt gggacctaaa accagacctg aatcagtatg cccggatttt tgcacaaaat    360

ctacccgagc caaaatctga ggtattctta ctaagaaaag atgaaaattc agcagcgtga    420

actagtaaaa aactagtaaa tataataaat aaaattaagg gatttaacaa tggattagac    480

ccagaaaatc ctgatttaag gttagttagc caactttatt tacttgattt tggcaaaatt    540

ggtgatgaaa atgctataga aaattttaaa gggatt                              576
```

<210> SEQ ID NO 68
<211> LENGTH: 192
<212> TYPE: PRT
<213> ORGANISM: Artificial Sequence
<220> FEATURE:
<223> OTHER INFORMATION: Description of Artificial Sequence:Deduced protein sequence from clone pAD1027

<400> SEQUENCE: 68

-continued

```
Glu Leu Ile Arg Glu Asn Leu Ser Leu Ala Lys Ser Phe Tyr Val Asp
  1               5                  10                  15

Lys Asn Asn Asn Pro Trp Ile Ser Thr Thr Lys Asn Phe Glu Asn Leu
             20                  25                  30

Phe Asp Tyr Val Gln Ser Glu His Leu Ile Asn Thr Asn Lys Ile Lys
         35                  40                  45

Asn Tyr Ile Thr Asn Ile Asn Phe Lys Ile Lys Lys Asn Ser Glu Ile
     50                  55                  60

Pro Ala Leu Glu Leu Asn Asn Leu Leu Lys Asp Asp Lys Ile Arg Leu
 65                  70                  75                  80

Glu Ile Asn Val Asp Ile Ser Lys Trp Val Gln Gln Lys Leu Ile Lys
                 85                  90                  95

Ile Leu Ser Phe Lys Phe Asp Trp Asp Leu Lys Pro Asp Leu Asn Gln
            100                 105                 110

Tyr Ala Arg Ile Phe Ala Gln Asn Leu Pro Glu Pro Lys Ser Glu Val
        115                 120                 125

Phe Leu Leu Arg Lys Asp Glu Asn Ser Ala Ala Trp Thr Ser Lys Lys
    130                 135                 140

Leu Val Asn Ile Ile Asn Lys Ile Lys Gly Phe Asn Asn Gly Leu Asp
145                 150                 155                 160

Pro Glu Asn Pro Asp Leu Arg Leu Val Ser Gln Leu Tyr Leu Leu Asp
                165                 170                 175

Phe Gly Lys Ile Gly Asp Glu Asn Ala Ile Glu Asn Phe Lys Gly Ile
            180                 185                 190


<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence:Clone
      pAD1037

<400> SEQUENCE: 69

catatgttaa ttgaagtttt aataattcac taccgtcaag ttcagtatgg ccaaagtatt     60

aaaaaatcag taatttataa cttaataaca accctgattt tagtgccgat tattacagtt    120

ggcgcctttt tgaaccgttt ttttattaaa acaggctgac taataccatt ttttaatgtt    180

tctggcgggg caattttaag ttttgttgtc ataattgagt tagttccaga atttatccat    240

ttaagaaata acccttcttt tcagtgacat ttttctcttt ttttgtttgc tttaggaatt    300

attttagcct taattatttt aatttacatg aacattaagc gccgtagatc c             351


<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence:Deduced
      protein sequence from clone pAD1037

<400> SEQUENCE: 70

      His Met Leu Ile Glu Val Leu Ile Ile His Tyr Arg Gln Val Gln Tyr
        1               5                  10                  15
      Gly Gln Ser Ile Lys Lys Ser Val Ile Tyr Asn Leu Ile Thr Thr Leu
                   20                  25                  30
      Ile Leu Val Pro Ile Ile Thr Val Gly Ala Phe Leu Asn Arg Phe Phe
               35                  40                  45
      Ile Lys Thr Gly Trp Leu Ile Pro Phe Phe Asn Val Ser Gly Gly Ala
           50                  55                  60
      Ile Leu Ser Phe Val Val Ile Ile Glu Leu Val Pro Glu Phe Ile His
```

-continued

```
 65                  70                  75                  80
Leu Arg Asn Asn Pro Ser Phe Gln Trp His Phe Ser Leu Phe Leu Phe
                85                  90                  95
Ala Leu Gly Ile Ile Leu Ala Leu Ile Ile Leu Ile Tyr Met Asn Ile
            100                 105                 110
Lys Arg Arg Arg Ser
        115
```

<210> SEQ ID NO 71
<211> LENGTH: 1776
<212> TYPE: DNA
<213> ORGANISM: Artificial Sequence
<220> FEATURE:
<223> OTHER INFORMATION: Description of Artificial Sequence:Clone pAD1038

<400> SEQUENCE: 71

```
gaattcgaaa aacgaattaa ggcaattttg caagaaattg agcaaaattc cgatcaagtt     60

attattttta ttgatgaaat tcaccttcta attggaacag gatcttctgg gactgattca    120

atggattttg ccaatatcct aaaaccaatt atggctcgcg gacagattaa attaatcggg    180

gctaccacaa attccgaata tcgcttatat atcgaaaaag atggcgccct tgaaagaaga    240

atgcaaaaag tagaaatttt agagccttca gttattgata caattaatat tttacgggga    300

attaaggaaa ggctagaaaa tttccatcaa gtaaaaatta aggattctgc tcttgttttt    360

gctacaaaag cggcaaatcg ttacattttt gaccgctttc tacctgataa agctatcgat    420

ttagtcgatg aagctgctgc ttctttaaaa gttgaaatca actaccaacc agaaaaactt    480

gaaaaagcaa agcgcgagct aatttattta aaaatggaag aaattaactc gcaaaaacaa    540

gataattcag aattaaaatc caaaattgaa aatcttgaaa atgaagtaaa aaaattacaa    600

gatcaatggg atcaatcaaa aaaatcagcc tctgaaatcg ctagcttatc ccaggaactt    660

gaaaaactaa aatatcaaca aaattactta atggaacaag gagactacca aaaagccgcc    720

gagattaaat acggaaaaat tcccaaaata agtaaaaaat taggcgaaat taaagcaaga    780

aggcaggaaa tttccaatgt tctagacgaa agtcagatcg caaaggttgt ctctaattga    840

acaaaaattc cgattgaaaa acttttagaa tcagaaattc aaaaatattt gaatttagaa    900

aaaaatttag caaaatcgct taagggtcaa aatcaggcaa ttaaggctgt ttcagatgcg    960

attttgcggt ttaaagctaa aattaatgat gaatcccgcc caatttcatc atttttcttt   1020

atgggaccaa ctggggtggg aaaaactgaa cttgctagag ctttagctct taatttattt   1080

aataataaaa accaaataat ccgtcttgat atgtcagaat atatggaaaa acatagtgtt   1140

tcaaagctaa ttggggctcc tccgggttat attggttttg aacaaggtgg taatctaaca   1200

aataaagtaa gactaaatcc ttattcgatt attttgcttg atgaaattga aaaagctcat   1260

ccggaagtaa tcaacatttt tttacaaatt cttgataatg gtgaaattgt tgatagtaag   1320

tcacaaaaag taaattttcg caatacaatt ataattatga cctcaaatat cggtgctaat   1380

aaaattcttg agggtaaaaa gatgaatgaa attgaggcaa aaaaggaact tttaagatat   1440

ttaaagccag aatttctcaa ccgaattgat gaaattatcg tatttaatcc tttaaattat   1500

gatataattt ttgaaattat tgaacttgaa ctaaaggatt tgcaaaatcg tctaaaggaa   1560

aataattttg agattgaatt tgaaaaatca gtcaaaaatt gaattttaga gtttggatat   1620

gataaaaatt ttggtgccag gccaattaag cgctttatta agaaagaaat tgaaaatttt   1680

gttgccaaaa aaatagtggc cgaagaaatt ttaaaagata aaaaatacaa tttatctttt   1740

aaaaatgata aattgcatct taatgaaagc gaaaat                             1776
```

-continued

<210> SEQ ID NO 72
<211> LENGTH: 592
<212> TYPE: PRT
<213> ORGANISM: Artificial Sequence
<220> FEATURE:
<223> OTHER INFORMATION: Description of Artificial Sequence:Deduced protein sequence from clone pAD1038

<400> SEQUENCE: 72

```
Glu Phe Glu Lys Arg Ile Lys Ala Ile Leu Gln Glu Ile Glu Gln Asn
  1               5                  10                  15

Ser Asp Gln Val Ile Ile Phe Ile Asp Glu Ile His Leu Leu Ile Gly
             20                  25                  30

Thr Gly Ser Ser Gly Thr Asp Ser Met Asp Phe Ala Asn Ile Leu Lys
         35                  40                  45

Pro Ile Met Ala Arg Gly Gln Ile Lys Leu Ile Gly Ala Thr Thr Asn
     50                  55                  60

Ser Glu Tyr Arg Leu Tyr Ile Glu Lys Asp Gly Ala Leu Glu Arg Arg
 65                  70                  75                  80

Met Gln Lys Val Glu Ile Leu Glu Pro Ser Val Ile Asp Thr Ile Asn
                 85                  90                  95

Ile Leu Arg Gly Ile Lys Glu Arg Leu Glu Asn Phe His Gln Val Lys
            100                 105                 110

Ile Lys Asp Ser Ala Leu Val Phe Ala Thr Lys Ala Ala Asn Arg Tyr
        115                 120                 125

Ile Phe Asp Arg Phe Leu Pro Asp Lys Ala Ile Asp Leu Val Asp Glu
    130                 135                 140

Ala Ala Ala Ser Leu Lys Val Glu Ile Asn Tyr Gln Pro Glu Lys Leu
145                 150                 155                 160

Glu Lys Ala Lys Arg Glu Leu Ile Tyr Leu Lys Met Glu Glu Ile Asn
                165                 170                 175

Ser Gln Lys Gln Asp Asn Ser Glu Leu Lys Ser Lys Ile Glu Asn Leu
            180                 185                 190

Glu Asn Glu Val Lys Lys Leu Gln Asp Gln Trp Asp Gln Ser Lys Lys
        195                 200                 205

Ser Ala Ser Glu Ile Ala Ser Leu Ser Gln Glu Leu Glu Lys Leu Lys
    210                 215                 220

Tyr Gln Gln Asn Tyr Leu Met Glu Gln Gly Asp Tyr Gln Lys Ala Ala
225                 230                 235                 240

Glu Ile Lys Tyr Gly Lys Ile Pro Lys Ile Ser Lys Lys Leu Gly Glu
                245                 250                 255

Ile Lys Ala Arg Arg Gln Glu Ile Ser Asn Val Leu Asp Glu Ser Gln
            260                 265                 270

Ile Ala Lys Val Val Ser Asn Trp Thr Lys Ile Pro Ile Glu Lys Leu
        275                 280                 285

Leu Glu Ser Glu Ile Gln Lys Tyr Leu Asn Leu Glu Lys Asn Leu Ala
    290                 295                 300

Lys Ser Leu Lys Gly Gln Asn Gln Ala Ile Lys Ala Val Ser Asp Ala
305                 310                 315                 320

Ile Leu Arg Phe Lys Ala Lys Ile Asn Asp Glu Ser Arg Pro Ile Ser
                325                 330                 335

Ser Phe Phe Phe Met Gly Pro Thr Gly Val Gly Lys Thr Glu Leu Ala
            340                 345                 350

Arg Ala Leu Ala Leu Asn Leu Phe Asn Asn Lys Asn Gln Ile Ile Arg
        355                 360                 365
```

```
Leu Asp Met Ser Glu Tyr Met Glu Lys His Ser Val Ser Lys Leu Ile
    370                 375                 380

Gly Ala Pro Pro Gly Tyr Ile Gly Phe Glu Gln Gly Gly Asn Leu Thr
385                 390                 395                 400

Asn Lys Val Arg Leu Asn Pro Tyr Ser Ile Ile Leu Leu Asp Glu Ile
                405                 410                 415

Glu Lys Ala His Pro Glu Val Ile Asn Ile Phe Leu Gln Ile Leu Asp
            420                 425                 430

Asn Gly Glu Ile Val Asp Ser Lys Ser Gln Lys Val Asn Phe Arg Asn
        435                 440                 445

Thr Ile Ile Ile Met Thr Ser Asn Ile Gly Ala Asn Lys Ile Leu Glu
    450                 455                 460

Gly Lys Lys Met Asn Glu Ile Glu Ala Lys Lys Glu Leu Leu Arg Tyr
465                 470                 475                 480

Leu Lys Pro Glu Phe Leu Asn Arg Ile Asp Glu Ile Ile Val Phe Asn
                485                 490                 495

Pro Leu Asn Tyr Asp Ile Ile Phe Glu Ile Ile Glu Leu Glu Leu Lys
            500                 505                 510

Asp Leu Gln Asn Arg Leu Lys Glu Asn Asn Phe Glu Ile Glu Phe Glu
        515                 520                 525

Lys Ser Val Lys Asn Trp Ile Leu Glu Phe Gly Tyr Asp Lys Asn Phe
    530                 535                 540

Gly Ala Arg Pro Ile Lys Arg Phe Ile Lys Lys Glu Ile Glu Asn Phe
545                 550                 555                 560

Val Ala Lys Lys Ile Val Ala Glu Glu Ile Leu Lys Asp Lys Lys Tyr
                565                 570                 575

Asn Leu Ser Phe Lys Asn Asp Lys Leu His Leu Asn Glu Ser Glu Asn
            580                 585                 590
```

<210> SEQ ID NO 73
<211> LENGTH: 796
<212> TYPE: DNA
<213> ORGANISM: Artificial Sequence
<220> FEATURE:
<223> OTHER INFORMATION: Description of Artificial Sequence:Clone pAD1040

<400> SEQUENCE: 73

```
atggtaaaat ctacaaaaca tttcaaattt atcctttgaa attgattata tttgattttt     60

acgatttttt ttaaaattta tctcattgtt gctccttatt ttatttttac ttttattcta    120

aatgaaaatt taactttttt ttgggtagcc acaacatctt ttttaggggt tagaattttt    180

aatatctttt tagattttat gaatcaagca tattttaaag ggtttttgat ctttcataag    240

atgaaacttg ccgaaaaaat aacaaatttt ttggaaaaaa cgacttacaa aaaatataac    300

gaaaattcaa gtgggtttta ctattcggaa attgaaaata caatagaaaa aagcgtttca    360

caattttatg caaatttatt gtccttttttg caaactcttt ccataatttt gatgacttta    420

ggtttatttt tttatataaa ctggatttta gcgttaatta ttgtcggtgt tataaccttt    480

tttgtaatta caacttcttt actatctaaa aaattaacca aacttcaatc cgcaaaattg    540

caagcaattt cggattttaa caattcttta agcacttatc ttttaacttt gccgcaatta    600

aaaaccttaa attctgatga taaattcgaa tttataatta ataaaagaaa caagaaaaat    660

tgaataacta gagaaaaata tggtatattt tccgacttaa tttcattttt taatgaatat    720

tccaataatt ttttctccgc aataatcaca attggaattg cattttggac actttattat    780
```

```
aaaaataata atagct                                                    796


<210> SEQ ID NO 74
<211> LENGTH: 265
<212> TYPE: PRT
<213> ORGANISM: Artificial Sequence
<220> FEATURE:
<223> OTHER INFORMATION: Description of Artificial Sequence:Deduced
      protein sequence from clone pAD1040

<400> SEQUENCE: 74

Met Val Lys Ser Thr Lys His Phe Lys Phe Ile Leu Trp Asn Trp Leu
  1               5                  10                  15

Tyr Leu Ile Phe Thr Ile Phe Phe Lys Ile Tyr Leu Ile Val Ala Pro
             20                  25                  30

Tyr Phe Ile Phe Thr Phe Ile Leu Asn Glu Asn Leu Thr Phe Phe Trp
         35                  40                  45

Val Ala Thr Thr Ser Phe Leu Gly Val Arg Ile Phe Asn Ile Phe Leu
     50                  55                  60

Asp Phe Met Asn Gln Ala Tyr Phe Lys Gly Phe Leu Ile Phe His Lys
 65                  70                  75                  80

Met Lys Leu Ala Glu Lys Ile Thr Asn Phe Leu Glu Lys Thr Thr Tyr
                 85                  90                  95

Lys Lys Tyr Asn Glu Asn Ser Ser Gly Phe Tyr Tyr Ser Glu Ile Glu
            100                 105                 110

Asn Thr Ile Glu Lys Ser Val Ser Gln Phe Tyr Ala Asn Leu Leu Ser
        115                 120                 125

Phe Leu Gln Thr Leu Ser Ile Ile Leu Met Thr Leu Gly Leu Phe Phe
    130                 135                 140

Tyr Ile Asn Trp Ile Leu Ala Leu Ile Ile Val Gly Val Ile Thr Phe
145                 150                 155                 160

Phe Val Ile Thr Thr Ser Leu Leu Ser Lys Lys Leu Thr Lys Leu Gln
                165                 170                 175

Ser Ala Lys Leu Gln Ala Ile Ser Asp Phe Asn Asn Ser Leu Ser Thr
            180                 185                 190

Tyr Leu Leu Thr Leu Pro Gln Leu Lys Thr Leu Asn Ser Asp Asp Lys
        195                 200                 205

Phe Glu Phe Ile Ile Asn Lys Arg Asn Lys Lys Asn Trp Ile Thr Arg
    210                 215                 220

Glu Lys Tyr Gly Ile Phe Ser Asp Leu Ile Ser Phe Phe Asn Glu Tyr
225                 230                 235                 240

Ser Asn Asn Phe Phe Ser Ala Ile Ile Thr Ile Gly Ile Ala Phe Trp
                245                 250                 255

Thr Leu Tyr Tyr Lys Asn Asn Asn Ser
            260                 265


<210> SEQ ID NO 75
<211> LENGTH: 453
<212> TYPE: DNA
<213> ORGANISM: Artificial Sequence
<220> FEATURE:
<223> OTHER INFORMATION: Description of Artificial Sequence:Clone pAD702

<400> SEQUENCE: 75

tcttatgaga aaaaatattt acctttgcta atagtccctg gaatttttgg cgctatttta     60

tttttctttt ttattaaaac acttttagac tataaagcaa tcaaaaaatc tgttatttat    120
```

```
tttcgttccc agttgcaaaa taatgcaaat cgacttgaaa tgccaccaat gattccatga    180

cttgtaaaaa aagtgaatca aaaagaggta aatgctatct gacttagcgg ctttactttg    240

tttgcaacaa ttatgatggg cttaacttac tgagtgttat taaaatatta tccggagaaa    300

aatattcaaa attctgccga atatataact gcaatggcag taaatggcgc tttgtttata    360

gttatgctaa tttatgattt aatgcttcgt cggcgtttgg gaaatattga agcaattttt    420

ggtcccattt atcataaaag ttttgatata ggt                                 453
```

```
<210> SEQ ID NO 76
<211> LENGTH: 151
<212> TYPE: PRT
<213> ORGANISM: Artificial Sequence
<220> FEATURE:
<223> OTHER INFORMATION: Description of Artificial Sequence:Deduced
      protein sequence from clone pAD702

<400> SEQUENCE: 76

Ser Tyr Glu Lys Lys Tyr Leu Pro Leu Leu Ile Val Pro Gly Ile Phe
  1               5                  10                  15

Gly Ala Ile Leu Phe Phe Leu Phe Ile Lys Thr Leu Leu Asp Tyr Lys
             20                  25                  30

Ala Ile Lys Lys Ser Val Ile Tyr Phe Arg Ser Gln Leu Gln Asn Asn
         35                  40                  45

Ala Asn Arg Leu Glu Met Pro Pro Met Ile Pro Trp Leu Val Lys Lys
     50                  55                  60

Val Asn Gln Lys Glu Val Asn Ala Ile Trp Leu Ser Gly Phe Thr Leu
 65                  70                  75                  80

Phe Ala Thr Ile Met Met Gly Leu Thr Tyr Trp Val Leu Leu Lys Tyr
                 85                  90                  95

Tyr Pro Glu Lys Asn Ile Gln Asn Ser Ala Glu Tyr Ile Thr Ala Met
            100                 105                 110

Ala Val Asn Gly Ala Leu Phe Ile Val Met Leu Ile Tyr Asp Leu Met
        115                 120                 125

Leu Arg Arg Arg Leu Gly Asn Ile Glu Ala Ile Phe Gly Pro Ile Tyr
    130                 135                 140

His Lys Ser Phe Asp Ile Gly
145                 150
```

```
<210> SEQ ID NO 77
<211> LENGTH: 99
<212> TYPE: DNA
<213> ORGANISM: Artificial Sequence
<220> FEATURE:
<223> OTHER INFORMATION: Description of Artificial Sequence:Clone pAD763

<400> SEQUENCE: 77

gatctttgtg ttatttttgt taataaaacc aagtttaaaa gtcatttccc ctggtttgtc     60

agtggtttta acatcataat aatagacaaa ataattctt                            99
```

```
<210> SEQ ID NO 78
<211> LENGTH: 33
<212> TYPE: PRT
<213> ORGANISM: Artificial Sequence
<220> FEATURE:
<223> OTHER INFORMATION: Description of Artificial Sequence:Deduced
      protein sequence from pAD763

<400> SEQUENCE: 78

Asp Leu Cys Val Ile Phe Val Asn Lys Thr Lys Phe Lys Ser His Phe
```

-continued

```
  1               5                  10                  15

Pro Trp Phe Val Ser Gly Phe Asn Ile Ile Ile Ile Asp Lys Ile Ile
             20                  25                  30

Leu


<210> SEQ ID NO 79
<211> LENGTH: 489
<212> TYPE: DNA
<213> ORGANISM: Artificial Sequence
<220> FEATURE:
<223> OTHER INFORMATION: Description of Artificial Sequence:Clone pAD766

<400> SEQUENCE: 79

gatcaacaaa aaccacaacc aaaagaagaa aaagaagaaa aacaagaaaa agaagaaaaa     60

aaaccgccga tagttcaagg tcctagtcca aaaccacaaa agattgaaaa tatcggtctt    120

gttaatgatt tttataaata caagtttaac gataaaattc ataaatttga accgactgag    180

tattataaaa atacagcaaa tttttctcag ggtggccttt atagtgcaaa tttgctcgaa    240

ttagaaaagg aaataaagaa acaagatccg gataatccta aaatatttta tgttcaaaga    300

cgaattgata ttggtggttt tctaacaaaa ggcacacttt taccatttca acccgcaaat    360

cttgagaata atttatcaag cctttcgctt tttgatagat attcccaatt tctgaggagc    420

ggcagattcg ataacaatta ttatataatt ggatccgata aggttgagga atttgatagg    480

ttgaaaaga                                                            489


<210> SEQ ID NO 80
<211> LENGTH: 163
<212> TYPE: PRT
<213> ORGANISM: Artificial Sequence
<220> FEATURE:
<223> OTHER INFORMATION: Description of Artificial Sequence:Deduced
      protein sequence from clone pAD766

<400> SEQUENCE: 80

Asp Gln Gln Lys Pro Gln Pro Lys Glu Glu Lys Glu Glu Lys Gln Glu
  1               5                  10                  15

Lys Glu Glu Lys Lys Pro Pro Ile Val Gln Gly Pro Ser Pro Lys Pro
             20                  25                  30

Gln Lys Ile Glu Asn Ile Gly Leu Val Asn Asp Phe Tyr Lys Tyr Lys
         35                  40                  45

Phe Asn Asp Lys Ile His Lys Phe Glu Pro Thr Glu Tyr Tyr Lys Asn
     50                  55                  60

Thr Ala Asn Phe Ser Gln Gly Gly Leu Tyr Ser Ala Asn Leu Leu Glu
 65                  70                  75                  80

Leu Glu Lys Glu Ile Lys Lys Gln Asp Pro Asp Asn Pro Lys Ile Phe
                 85                  90                  95

Tyr Val Gln Arg Arg Ile Asp Ile Gly Gly Phe Leu Thr Lys Gly Thr
            100                 105                 110

Leu Leu Pro Phe Gln Pro Ala Asn Leu Glu Asn Asn Leu Ser Ser Leu
        115                 120                 125

Ser Leu Phe Asp Arg Tyr Ser Gln Phe Leu Arg Ser Gly Arg Phe Asp
    130                 135                 140

Asn Asn Tyr Tyr Ile Ile Gly Ser Asp Lys Val Glu Glu Phe Asp Arg
145                 150                 155                 160

Leu Lys Arg
```

-continued

```
<210> SEQ ID NO 81
<211> LENGTH: 474
<212> TYPE: DNA
<213> ORGANISM: Artificial Sequence
<220> FEATURE:
<223> OTHER INFORMATION: Description of Artificial Sequence:Clone pAD957

<400> SEQUENCE: 81

agctatttta gtattataag ccctttgttt ttggctgttt cttgcacaaa cattataatt     60

agcaaatctg aattatcaaa aatagaaagt aatattttta attttataat aaacgaaaat    120

gaaaaaaatt taactagatt taccgcaact ttagtaaaaa aaactaataa taacttgact    180

tttgtcagta cttttcattc gctaaattca ataaaaaaca atatacagca acaagttttt    240

gatatttttt tacaacaatt tagtgtgaaa aatttagaaa ctaaattaaa atcaaaaatt    300

agagttgaat atgaaaataa agaaaaagat atcatagttt tttcgctaga tataaaggaa    360

cccttattgt tgagaatttc ggattctatt gattttcagg ttctagagga ttttacaaac    420

acaaaaaata gcctatttag cttaaggttt ctcaccgatc ttaaacgaag attt          474


<210> SEQ ID NO 82
<211> LENGTH: 158
<212> TYPE: PRT
<213> ORGANISM: Artificial Sequence
<220> FEATURE:
<223> OTHER INFORMATION: Description of Artificial Sequence:Deduced
      protein sequence from clone pAD957

<400> SEQUENCE: 82

Ser Tyr Phe Ser Ile Ile Ser Pro Leu Phe Leu Ala Val Ser Cys Thr
  1               5                  10                  15

Asn Ile Ile Ile Ser Lys Ser Glu Leu Ser Lys Ile Glu Ser Asn Ile
             20                  25                  30

Phe Asn Phe Ile Ile Asn Glu Asn Glu Lys Asn Leu Thr Arg Phe Thr
         35                  40                  45

Ala Thr Leu Val Lys Lys Thr Asn Asn Asn Leu Thr Phe Val Ser Thr
     50                  55                  60

Phe His Ser Leu Asn Ser Ile Lys Asn Asn Ile Gln Gln Gln Val Phe
 65                  70                  75                  80

Asp Ile Phe Leu Gln Gln Phe Ser Val Lys Asn Leu Glu Thr Lys Leu
                 85                  90                  95

Lys Ser Lys Ile Arg Val Glu Tyr Glu Asn Lys Glu Lys Asp Ile Ile
            100                 105                 110

Val Phe Ser Leu Asp Ile Lys Glu Pro Leu Leu Leu Arg Ile Ser Asp
        115                 120                 125

Ser Ile Asp Phe Gln Val Leu Glu Asp Phe Thr Asn Thr Lys Asn Ser
    130                 135                 140

Leu Phe Ser Leu Arg Phe Leu Thr Asp Leu Lys Arg Arg Phe
145                 150                 155


<210> SEQ ID NO 83
<211> LENGTH: 123
<212> TYPE: DNA
<213> ORGANISM: Artificial Sequence
<220> FEATURE:
<223> OTHER INFORMATION: Description of Artificial Sequence:Clone pAD996

<400> SEQUENCE: 83

agctatctat taattatgat gccgcagggg gaacctatca cactactggt taaggtcatt     60

acgctagcgg ttatgcactc agatgaaaat gctgaaaggt acataaactc tgatgatccg    120
```

-continued

```
atc                                                                        123


<210> SEQ ID NO 84
<211> LENGTH: 41
<212> TYPE: PRT
<213> ORGANISM: Artificial Sequence
<220> FEATURE:
<223> OTHER INFORMATION: Description of Artificial Sequence:Deduced
      protein sequence from pAD996

<400> SEQUENCE: 84

Ser Tyr Leu Leu Ile Met Met Pro Gln Gly Glu Pro Ile Thr Leu Leu
  1               5                  10                  15

Val Lys Val Ile Thr Leu Ala Val Met His Ser Asp Glu Asn Ala Glu
             20                  25                  30

Arg Tyr Ile Asn Ser Asp Asp Pro Ile
         35                  40
```

METHODS OF IDENTIFYING ANTIGEN GENE SEQUENCES

This application is a continuation of International Application PCT/AU99/01035, filed Nov. 19, 1999 and published in English, of which the entire disclosure of the pending, prior application is hereby incorporated by reference.

The present invention relates to methods of identifying gene sequences of potential vaccine antigens. Also included are gene sequences and the polypeptides encoded by the gene sequences as well as the use of such sequences to induce a protective immune response in animals. Particularly, the invention relates to identifying potential antigen gene sequences of Mycoplasma, preferably *Mycoplasma hyopneumoniae.*

INTRODUCTION

The success of a vaccine to a pathogen resides in identifying a suitable antigen of a pathogen which is readily accessible to a host immune system. Once identified, it can form the basis for protection against the pathogen.

In recent years a number of vaccines have been commercialised by Animal Health companies. Many of the vaccines are based on inactivated whole cell bacterins. Although these vaccines provide a reasonable level of efficacy there is considerable scope for improvement. Therefore the presently available vaccines could be improved on by developing vaccines that were not based on whole cells or fractions of whole cells.

Other means of generating vaccines against pathogens includes the use of crude inactivated antigen mixtures of various proteins. However, the problem with these methods is that they present to the host a variety of antigens, none of which may provide suitable overall protection since the proteins most readily accessible to a host immune system are swamped by the other antigens. Moreover, some pathogens are difficult or expensive to grow because of their fastidious requirements. Some pathogens are also harmful to handle. Therefore, a vaccine which does not require the growing of the cells or bacteria and the processing of whole cells or fractions of whole cells would provide a safer, cheaper and possibly more efficacious vaccine.

One way of achieving a cleaner and more specific vaccine is by using recombinant protective antigens. By providing specific antigens, only those antigens readily accessible to the host immune system may be used.

There is the problem of identifying potential antigens. One way is to create a gene library. However, from the library, it is very time consuming to determine those sequences which may include a potential protective antigen.

To efficiently screen through a large number of potential antigen genes for their efficacy in providing some level of protection from disease it is useful to initially clone them as expressing clones. In this way the need for tedious and time consuming clone analysis and subsequent expression subcloning is avoided. The whole process of antigen discovery is speeded up. Applicants now provide a novel method to ensure that the clones initially investigated were expressing recombinant protein.

Previously, expression libraries have been screened for clones expressing all or part of a specific protein by using an antibody specific for or enriched for the protein of interest.

Identifying the DNA sequences that code for the proteins, also makes it possible, using appropriate expression vehicles, to form recombinant DNA molecules and to transform appropriate hosts (eg., prokaryotic or eukaryotic hosts) with those recombinant DNA molecules. Culturing of the transformed hosts then permits the hosts to express the DNA sequences and to produce the desired proteins.

Administering the produced and subsequently isolated proteins, active ingredients or combinations thereof (eg., by injection), in an amount sufficient to elicit a protective immune response, provides a means for immunising against infections.

One pathogen for which vaccines have been commercialised by Animal Health companies is *Mycoplasma hyopneumoniae*. This pathogen causes *Enzootic pneumonia* in pigs. It rarely causes death, but often results in severe morbidity and reduced performance manifesting in significant depression in feed conversion efficiency resulting in reduced weight gain in pigs. The animals show symptoms of coughing and fever and are often prone to secondary infection by opportunistic microorganisms.

Numerous attempts to provide a vaccine against *Mycoplasina hyopneumoniae* have not been terribly successful. Particularly, the use of heat inactivated, live or extract of Mycoplasma have proven to be ineffective in providing protection. Some vaccines based on inactivated whole cell bacterins have shown some level of efficacy but there is scope for improvement.

Additionally, *Mycoplasma hyopneumoniae* is difficult and expensive to grow because of its fastidious requirements. Therefore the presently available vaccines could be improved on by developing vaccines that were not based on whole cells or fractions of whole cells.

Accordingly, it is an object of the present invention to overcome or at least alleviate some of the problems of the prior art.

SUMMARY OF THE INVENTION

In one aspect of the present invention there is provided a method of identifying expression proteins translated from a nucleotide sequence in an expression vector, said method comprising the use of a marker co-expressed with a protein translated from the nucleotide sequence.

In a preferred embodiment of the present invention there is provided a use of a polyHis tag for identifying expression proteins encoded by a nucleotide sequence in an expression vector wherein said polyHis tag is co-expressed with said protein.

In another aspect of the present invention there is provided a method for identifying expression proteins encoded by a nucleotide sequence from a mixture of nucleotide sequences, said method comprising the steps of:

- providing an expression vector including a marker;
- introducing a nucleotide sequence from the mixture into the expression vector; and
- identifying an expression protein expressed by the expression vector by determining the presence of a fusion protein comprising the marker co-expressed with the expression protein.

In a preferred embodiment the marker is a polyHis tag.

In a further preferred embodiment, the expression vector is transfected into a host cell for expression of a marker-fusion protein comprising an expression protein. Preferably the marker fusion protein is a polyHis tag-fusion protein comprising a polyHis tag and an expression protein. Introduction of a population of expression vectors into the host cell may create a genomic or cDNA library which may be screened.

In a further preferred embodiment of the method there is included a step of purifying the expression protein using the marker expressed in the fusion protein. Preferably the marker is a polyHis tag.

There is provided in another aspect, a purified recombinant protein identified according to the above method. Preferably the recombinant protein is an expression protein.

In another aspect, there is provided a purified nucleotide sequence which encodes a recombinant protein identified according to the above method.

In another aspect of the present invention there is provided an expression vector including a marker, preferably a polyHis tag for use in identifying expression proteins encoded by a nucleotide sequence.

In yet another aspect of the invention, there is provided a host including an expression vector, said vector including a marker, preferably a polyHis tag for use in identifying an expression protein.

In a further aspect of the present invention, there is provided a method of identifying gene sequences encoding antigenic proteins from a sample of nucleotide sequences, said method comprising the steps of:

providing an expression vector including a marker;

introducing a nucleotide sequence from the sample into the expression vector;

identifying an antigenic expression protein expressed by the expression vector by determining the presence of a fusion protein comprising a marker co-expressed with the expression protein translated by the nucleotide sequence; and identifying the antigenic expression protein.

Preferably the marker is a polyHis tag.

In a preferred embodiment, the method further includes determining the gene sequence of the antigenic protein encoded by the expression vector.

In another aspect of the invention there is provided a method of screening a library of nucleotide sequences, said method including the steps of:

providing a source of nucleotide sequences;

providing an expression vector including a marker;

creating a library by introducing a nucleotide sequence into the expression vector;

identifying an expression protein expressed by the expression vector by determining the presence of a fusion protein comprising a marker co-expressed with the expression protein translated by the nucleotide sequence; and determining the nucleotide sequence of the expression protein.

Preferably the marker is a polyHis tag.

In another aspect, there is provided a method of screening to identify expression clones in an expression library wherein said method includes:

providing a source of nucleotide sequence;

providing an expression vector including a marker;

introducing the nucleotide sequence into the expression vector;

transforming the expression vector into a host to create an expression library; and locating an expression clone by detecting the expression of a fusion protein, comprising a marker, preferably a polyHis tag co-expressed with an expression protein.

In a further aspect of the present invention there is provided a method of identifying a therapeutic antigenic gene sequence encoding a therapeutic antigenic protein of a disease, from a sample of nucleotide sequences, said method comprising the steps of:

providing an expression vector including a marker;

introducing a nucleotide sequence from the sample into the expression vector;

identifying an antigenic expression protein expressed by the expression vector by determining the presence of a fusion protein comprising a marker, co-expressed with the expression protein translated by the nucleotide sequence;

inoculating an animal with the expression vector which expresses the antigenic expression protein;

challenging the animal with the disease;

identifying an expression vector and expression protein that provides a therapeutic effect induced by vaccination; and determining the gene sequence of the antigenic expression protein encoded by the expression vector.

Preferably the marker is a polyHis tag.

In a further preferred embodiment of the invention, there is provided a method of screening a library of nucleotide sequences for a nucleotide sequence encoding polypeptides of Mycoplasma, preferably *Mycoplasma hyopneumoniae*, said method comprising the steps of:

providing a source of nucleotide sequences from a sample of Mycoplasma;

providing an expression vector including a marker;

introducing a nucleotide sequence into the expression vector;

identifying a Mycoplasma expression protein expressed by the expression vector by determining the presence of a fusion protein comprising a marker, preferably a polyHis tag, co-expressed with the expression protein translated by a nucleotide sequence; and determining the nucleotide sequence of the expression protein of Mycoplasma, preferably *Mycoplasma hyopneumoniae.*

Preferably the marker is a polyHis tag.

In a preferred embodiment, the gene sequence encodes an antigenic polypeptide of Mycoplasma, preferably *Mycoplasma hyopneumoniae.*

In yet another aspect of the present invention, there is provided a nucleotide sequence, mutant, analogue, derivative or functionally active fragment thereof encoding a polypeptide of Mycoplasma, preferably *Mycoplasma hyopneumoniae*, said nucleotide sequence identified by the methods described above. Preferably the nucleotide sequence composes a sequence according to any one of FIGS. 1 to 42, and mutants, analogues derivatives or functionally active fragments thereof. More specifically, the nucleotide sequence is according to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO;33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

In an even further aspect of the present invention, there is provided a polypeptide encoded by the nucleotide sequence mutant, analogue, derivatives or functionally active fragments thereof encoding a polypeptide of Mycoplasma, preferably *Mycoplasma hyopneumoniae*, said nucleotide sequence identified by the methods described above. Preferably the polypeptide is encoded by a nucleotide sequence encoded by a sequence according to any one of FIGS. 1 to 42, mutant, analogues, derivatives or functionally active fragment thereof. More specifically the polypeptide has an amino acid sequence according to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82 or SEQ ID NO: 84 or a mutant, analogue, derivatives or functionally active fragments thereof.

In a further aspect of the present invention, there is included compositions comprising the polypeptides or nucleotide sequences described above. Furthermore in other aspects, there is included pharmaceutical compositions and vaccine compositions of the polypeptide or nucleotide sequences described above.

Other aspects of the invention include monoclonal antibodies generated against the polypeptides.

Also included as a further aspect of the invention is a method of treating Mycoplasma infection, said method including administering an effective amount of an antigen polypeptide of Mycoplasma encoded by a nucleotide sequence or nucleotide sequence encoding the polypeptide identified by the methods above. Preferably, the antigen polypeptide is encoded by a nucleotide sequence according to any one of FIGS. 1 to 42 or a mutant, analogue, derivative or functionally active fragment thereof. More specifically the nucleotide sequence is according to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO;15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

Throughout the description and claims of this specification, the word "comprise" and variations of the word, such as "comprising" and "comprises", is not intended to exclude other additives, components, integers or steps.

BRIEF DESCRIPTION OF FIGURES

FIG. 1 shows the nucleotide (SEQ ID NO: 1) and amino acid sequence (SEQ ID NO: 2) of Mycoplasma represented by clone pAD612.

FIG. 2 shows the nucleotide (SEQ ID NO: 3) and amino acid sequence (SEQ ID NO: 4) of Mycoplasma represented by clone pAD633.

FIG. 3 shows the nucleotide (SEQ ID NO: 5) and amino acid sequence (SEQ ID NO: 6) of Mycoplasma represented by clone pAD639.

FIG. 4 shows the nucleotide (SEQ ID NO: 7) and amino acid sequence (SEQ ID NO: 8) of Mycoplasma represented by clone pAD640.

FIG. 5 shows the nucleotide (SEQ ID NO: 9) and amino acid sequence (SEQ ID NO: 10) of Mycoplasma represented by clones pAD641 and pAD1033.

FIG. 6 shows the nucleotide (SEQ ID NO: 11) and amino acid sequence (SEQ ID NO: 12) of Mycoplasma represented by clone pAD653.

FIG. 7 shows the nucleotide (SEQ ID NO: 13) and amino acid sequence (SEQ ID NO: 14) of Mycoplasma represented by clones pAD657 and pAD964.

FIG. 8 shows the nucleotide (SEQ ID NO: 15) and amino acid sequence (SEQ ID NO: 16) of Mycoplasma represented by clones pAD659 and pAD910.

FIG. 9 shows the nucleotide (SEQ ID NO: 17) and amino acid sequence (SEQ ID NO: 18) of Mycoplasma represented by clone pAD662.

FIG. 10 shows the nucleotide (SEQ ID NO: 19) and amino acid sequence (SEQ ID NO: 20) of Mycoplasma represented by clone pAD681.

FIG. 11 shows the nucleotide (SEQ ID NO: 21) and amino acid sequence (SEQ ID NO: 22) of Mycoplasma represented by clone pAD700.

FIG. 12 shows the nucleotide (SEQ ID NO: 23) and amino acid sequence (SEQ ID NO: 24) of Mycoplasma represented by clone pAD711.

FIG. 13 shows the nucleotide (SEQ ID NO: 25) and amino acid sequence (SEQ ID NO: 26) of Mycoplasma represented by clone pAD721.

FIG. 14 shows the nucleotide (SEQ ID NO: 27) and amino acid sequence (SEQ ID NO: 28) of Mycoplasma represented by clone pAD727.

FIG. 15 shows the nucleotide (SEQ ID NO: 29) and amino acid sequence (SEQ ID NO: 30) of Mycoplasma represented by clone pAD742.

FIG. 16 shows the nucleotide (SEQ ID NO: 31) and amino acid sequence (SEQ ID NO: 32) of Mycoplasma represented by clone pAD760.

FIG. 17 shows the nucleotide (SEQ ID NO: 33) and amino acid sequence (SEQ ID NO: 34) of Mycoplasma represented by clones pAD774.

FIG. 18 shows the nucleotide (SEQ ID NO: 35) and amino acid sequence (SEQ ID NO: 36) of Mycoplasma represented by clone pAD784.

FIG. 19 shows the nucleotide (SEQ ID NO: 37) and amino acid sequence (SEQ ID NO: 38) of Mycoplasma represented by clone pAD789.

FIG. 20 shows the nucleotide (SEQ ID NO: 39) and amino acid sequence (SEQ ID NO: 40) of Mycoplasma represented by clones pAD908, pAD981, pAD1013 and pAD1049.

FIG. 21 shows the nucleotide (SEQ ID NO: 41) and amino acid sequence (SEQ ID NO: 42) of Mycoplasma represented by clones pAD913.

FIG. 22 shows the nucleotide (SEQ ID NO: 43) and amino acid sequence (SEQ ID NO: 44) of Mycoplasma represented by clone pAD920.

FIG. 23 shows the nucleotide (SEQ ID NO: 45) and amino acid sequence (SEQ ID NO: 46) of Mycoplasma represented by clone pAD922.

FIG. 24 shows the nucleotide (SEQ ID NO: 47) and amino acid sequence (SEQ ID NO: 48) of Mycoplasma represented by clones pAD923 and pAD925.

FIG. 25 shows the nucleotide (SEQ ID NO: 49) and amino acid sequence (SEQ ID NO: 50) of Mycoplasma represented by clone pAD950.

FIG. 26 shows the nucleotide (SEQ ID NO: 51) and amino acid sequence (SEQ ID NO: 52) of Mycoplasma represented by clone pAD951.

FIG. 27 shows the nucleotide (SEQ ID NO: 53) and amino acid sequence (SEQ ID NO: 54) of Mycoplasma represented by clone pAD977.

FIG. 28 shows the nucleotide (SEQ ID NO: 55) and amino acid sequence (SEQ ID NO: 56) of Mycoplasma represented by clone pAD983.

FIG. 29 shows the nucleotide (SEQ ID NO: 57) and amino acid sequence (SEQ ID NO: 58) of Mycoplasma represented by clone pAD984.

FIG. 30 shows the nucleotide (SEQ ID NO: 59) and amino acid sequence (SEQ ID NO: 60) of Mycoplasma sequence 30 represented by clone pAD994.

FIG. 31 shows the nucleotide (SEQ ID NO: 61) and amino acid sequence (SEQ ID NO: 62) of Mycoplasma represented by clone pAD1005.

FIG. 32 shows the nucleotide (SEQ ID NO: 63) and amino acid sequence (SEQ ID NO: 64) of Mycoplasma represented by clone pAD1016.

FIG. 33 shows the nucleotide (SEQ ID NO: 65) and amino acid sequence (SEQ ID NO: 66) of Mycoplasma represented by clone pAD1020.

FIG. 34 shows the nucleotide (SEQ ID NO: 67) and amino acid sequence (SEQ ID NO: 68) of Mycoplasma represented by clone pAD1027.

FIG. 35 shows the nucleotide (SEQ ID NO: 69) and amino acid sequence (SEQ ID NO: 70) of Mycoplasma represented by clone pAD1037.

FIG. 36 shows the nucleotide (SEQ ID NO: 71) and amino acid sequence (SEQ ID NO: 72) of Mycoplasma represented by clone pAD1038.

FIG. 37 shows the nucleotide (SEQ ID NO: 73) and amino acid sequence (SEQ ID NO: 74) of Mycoplasma represented by clones pAD1040.

FIG. 38 shows the nucleotide (SEQ ID NO: 75) and amino acid sequence (SEQ ID NO: 76) of Mycoplasma represented by clone pAD702.

FIG. 39 shows the nucleotide (SEQ ID NO: 77) and amino acid sequence (SEQ ID NO: 78) of Mycoplasma represented by clone pAD763.

FIG. 40 shows the nucleotide (SEQ ID NO: 79) and amino acid sequence (SEQ ID NO: 80) of Mycoplasma represented by clone pAD766.

FIG. 41 shows the nucleotide (SEQ ID NO: 81) and amino acid sequence (SEQ ID NO: 82) of Mycoplasma represented by clone pAD957.

FIG. 42 shows the nucleotide (SEQ ID NO: 83) and amino acid sequence (SEQ ID NO: 84) of Mycoplasma represented by clone pAD996.

DETAILED DESCRIPTION OF THE INVENTION

In one aspect of the present invention there is provided a method of identifying expression proteins translated from a nucleotide sequence in an expression vector, said method comprising the use of a marker co-expressed with a protein translated from the nucleotide sequence.

In a preferred embodiment, the marker is any marker which can be detected. Detection may be by a monoclonal antibody or specific polyclonal antiserum. Preferably the marker is small, preferably less than 30 amino acids. Most preferably, the marker is a polyHis tag. Although the tag may also be any one of the following such as:

(a) the FLAG tag, an 8 amino acid tag sequence which is available in plasmid vectors from Sigma-Aldrich Inc. USA, (b) the I-SPY epitope 6 amino acid tag available in vectors from Amrad Corporation Ltd., Australia, (c) the Hemagglutinin epitope 9 amino acid tag (Clontech Laboratories Inc. USA); and (d) the c-Myc epitope 12 amino acid tag (Clontech Laboratories Inc. USA).

When the marker is a polyHis tag, the number of histidine residues is preferably in the range of 4 to 8 histidine residues, most preferably, there are 6 histidine residues. At least four amino acid residues may precede the polyHis tag providing a total of at least 10 amino acids providing there are at least 4 to 8 contiguous histidine residues.

To efficiently screen through a large number of potential antigen genes for their efficacy in providing some level of protection from disease it is useful to initially clone them as expressing clones. In this way the need for tedious and time consuming clone analysis and subsequent expression sub-cloning is avoided. The whole process of antigen discovery is speeded up. Applicants provide a novel method to ensure that the clones initially investigated were expressing recombinant protein.

This is particularly the case when dealing with a gene library. Within any random library, there are a majority of clones which are in the incorrect orientation for expression or in the wrong reading frame to express a protein. The use of a marker, preferably a polyHis tag in an expression vector allows for the efficient identification of expressing clones which express a marker, preferably a polyHis tag fusion protein.

In clones that are not producing a recombinant marker-fusion protein or preferably a polyHis fusion protein, or only a short recombinant protein, the small marker or polyHis protein that is encoded is rapidly degraded within the host cell and any marker or polyHis protein that remains binds very weakly to membranes used for colony screening. Thus non-productive clones give a negative result in colony screening whereas clones producing a longer tagged recombinant protein can give a positive signal. Thus a general genomic expression library can be reduced significantly in complexity and therefore allow faster and more efficient screening and subsequent utilisation of desired clones.

Such clones expressing the proteins are deemed as potential protective antigens and because of the strategy used to construct and screen the clones the originally isolated clones could be immediately used in vaccine trials, both in the form of purified plasmid DNA for genetic vaccination, or as a purified marker-fusion recombinant protein, preferably a polyHis purified recombinant fusion protein.

Where the marker is a polyHis tag region, it may be derived from any source that contains the region. For instance, the regions of the vectors pQE30, pQE31 and pQE32 (Qiagen Pty. Ltd. Australia) encoding the polyHis tag may be used. Other sources of polyHis tag may be obtained from Novagen Inc., USA, (pET-1.9–33) or by synthetically making a polyHis tag.

In another aspect of the present invention there is provided a method for identifying expression proteins translated from a nucleotide sequence from a mixture of nucleotide sequences, said method comprising the steps of:

providing an expression vector including a marker;

introducing a nucleotide sequence from the mixture into the expression vector; and identifying an expression protein expressed by the expression vector by determining the presence of a fusion protein comprising the marker co-expressed with the expression protein.

Preferably, the marker is a polyHis tag. The following specific examples are directed to a polyHis tag marker and polyHis tag fusion proteins. However, any marker which can be detected and co-expressed with the protein in an expressing clone may be used. Accordingly, the present invention is not restricted to polyHis tags. This marker is illustrative only and should not be taken in any way as a restriction on the generality of the invention described.

As described above, identification of expression proteins, particularly from clones derived from a gene library, can expedite the identification of nucleotide sequences encoding potential antigens to pathogens.

The mixture of nucleotide sequences may be derived from any source such as from a tissue sample, microorganism, cell or any component which contains nucleic acid. Preferably the nucleic acid is genomic, mitochondrial, recombinant or mRNA. A sample of DNA may be firstly subjected to any means which fragments the DNA such as by sonication or by enzyme digestion such as restriction enzyme digestion. Alternatively, the nucleotide sequences may derive from PCR of a portion of a DNA sequence described above. These sequences may be open reading frames (ORF). The expression vector preferably includes a polyHis tag. The polyHis tag may be derived from any source harbouring the polyHis tag as discussed above.

Preferably the polyHis tag may be derived from standard vectors such as pQE30, pQE31 and pQE32 (Qiagen Pty. Ltd,, Australia). These vectors may be encode a T5 promoter, Lac operator and polyHis tag region. This region may cloned into an expression vector which is capable of expressing proteins encoded by the nucleotide sequences. Alternatively, the polyHis tag may be made synthetically.

Preferably the marker or preferably a polyHis tag region is cloned into a eukaryotic expression vector. Most preferably, the vector is pCl (Promega Corporation, Australia) and preferably creates clones pCl30, pCl31, and pCl32.

This series of vectors allows the cloning of fragments downstream of the polyHis tag region in all three reading frames. The cytomegalovirus (CMV) immediate-early enhancer/promoter, chimeric intron, and SV40 late polyadenylation signal in these exemplified clones allow the vectors to be used as eukaryotic expression vectors in cell culture systems and genetic immunisations using purified plasmid DNA. The T5 promoter allows expression of cloned inserts in prokaryotes. The construction of these vectors is significant because they enable the screening of a library to identify a large number of clones that are expressing recombinant proteins.

The nucleotide sequence(s) from the mixture such as from a digestion of genomic DNA may be introduced or cloned into the expression vector by any means known to the skilled addressee. The expression vector may be used to express protein in a host cell.

In a preferred embodiment, the expression vector is transfected into a host cell for expression of the expression protein of polyHis fusion protein comprising a polyHis tag and an expression protein. Introduction of the expression vector into the host cell may create a genomic or cDNA library.

The host cell may be any cell competent to receive the expression vector. Preferably the cell is prokaryotic. Most preferably it is *Escherichia coli*. Identification of the expression protein (and consequently any clones or host cells) expressing the protein can be determined by the presence of the polyHis tag on a polyHis tag fusion protein.

The vectors in the present invention allow the general screening for all expressing clones on the basis of the polyHis tag.

The polyHis tag may be identified by anti-polyHis antibodies or with metal-chelate conjugated probes such as nickel resin wherein the polyHis signals are developed by addition of a chromogenic substrate.

In clones that are not producing a recombinant polyHis fusion protein, or only a short recombinant protein, the small polyHis protein that is encoded is rapidly degraded within the host cell and any polyHis protein that remains binds very weakly to membranes used for colony screening. Thus non-productive clones give a negative result in polyHis colony screening whereas clones producing a longer polyHis tagged recombinant protein can give a positive signal. Thus a general genomic expression library can be reduced significantly in complexity and therefore allow faster and more efficient screening and subsequent utilisation of desired clones.

In a further preferred embodiment of the method there is included a step of purifying the expression protein using the polyHis tag expressed in the fusion protein.

Once an expression protein expressed by an expression clone is identified using the polyHis tag, then this tag may also be used to purify any expression proteins. Any purification method may be used which is known by the skilled addressee. Affinity columns in affinity chromatography with anti-polyHis antibodies may be used. Generally, the expressed protein, identified by virtue of the polyHis tag, may be isolated by any means which relies on utilising the polyHis tag.

There is provided in another aspect, a purified recombinant protein identified according to the above method.

Once the protein is isolated, it may be used in any number of ways including vaccine trials in the form of purified proteins. The proteins can be immediately identified as potential antigens. Preferably, they will be protective antigens.

In another aspect, there is provided a purified nucleotide sequence which encodes recombinant protein identified according to the above method.

The proteins identified by the polyHis method described above are expressed by discrete nucleotide sequences, preferably recombinant sequences. By identifying the protein, a clone expressing the protein may be identified which harbours the nucleotide sequence.

These clones may provide purified plasmid DNA, particularly the plasmid DNA may represent a potential protective antigen.

In another aspect of the present invention there is provided an expression vector or a recombinant vector including a marker, preferably a polyHis tag for use in identifying expression proteins encoded by a nucleotide sequence.

The expression vector may be any vector which produces expression of an expression protein. It may be a plasmid or cosmid. It may be introduced into clones for further expansion of the expression protein for the purposes of obtaining the protein for vaccination or identification purposes.

In yet another aspect of the invention, there is provided a host including an expression vector, said vector including a marker, preferably a polyHis tag for use in identifying an expression protein encoded by a nucleotide sequence.

The host cell may be any competent cell which can harbour an expression vector. Preferably, the host cell is prokaryotic or eukaryotic.

In a further aspect of the present invention, there is provided a method of identifying gene sequences encoding antigenic proteins from a sample of nucleotide sequences, said method comprising the steps of providing an expression vector including a marker, preferably a polyHis tag;

introducing a nucleotide sequence from the sample into the expression vector;

identifying an antigenic expression protein expressed by the expression vector by determining the presence of a fusion protein comprising a marker, co-expressed with the expression protein translated by the nucleotide sequence;

identifying the antigenic protein; and preferably determining the nucleotide sequence of the antigenic protein gene encoded by the expression vector.

Identification of an antigenic protein may include identifying and preferably isolating a fusion protein having a polyHis tag and determining whether the fusion protein can elicit an immune response which is not generated by virtue of the polyHis tag. Determination of an immune response may be conducted by standard in vitro immunological tests using antisera from immune animals conducting ELISA's or antibody/antigen reactions. They may also be tested in vivo in protection trials in animals against further challenge.

In another aspect of the invention there is provided a method of screening a library of nucleotide sequences, said method including the steps of:

providing a source of nucleotide sequences;

providing an expression vector including a marker, preferably a polyHis tag;

creating a library by introducing a nucleotide sequence into the expression vector;

identifying an expression protein expressed by the expression vector by determining the presence of a fusion protein comprising a marker co-expressed with the expression protein translated by the nucleotide sequence; and determining the nucleotide sequence of the expression protein gene.

In another aspect, there is provided a method of screening to identify expression clones in a library wherein said method includes:

providing a source of nucleotide sequences;

providing an expression vector including a marker, preferably a polyHis tag;

introducing a nucleotide sequence into the expression vector;

transforming the expression vector into a host to create an expression library; and locating an expression clone by detecting the expression of a fusion protein, comprising a marker, preferably a polyHis tag co-expressed with an expression protein.

Identification of the expression proteins having a polyHis tag transcribed by the expression clones further identifies those clones (host cells) which express an open reading frame (ORF).

Accordingly, the method identifies ORF's in a mixture of nucleotide sequences. This effectively speeds up the process of identifying useful nucleotide sequences encoding proteins which are potentially useful as antigens. It quickly identifies a clone which can be immediately expanded to provide sufficient sample of nucleotide sequence or plasmid DNA or recombinant protein for any use such as in genetic vaccines or for developing antibodies against a recombinant protein.

In a further aspect of the present invention there is provided a method of identifying a therapeutic antigenic gene sequence encoding a therapeutic antigenic protein of a disease, from a sample of nucleotide sequences, said method comprising the steps of:

providing an expression vector including a marker;

introducing a nucleotide sequence from the sample into the expression vector;

identifying an antigenic expression protein expressed by the expression vector by determining the presence of a fusion protein comprising a marker, co-expressed with the expression protein translated by the nucleotide sequence;

inoculating an animal with the expression vector which expresses the antigenic expression protein;

challenging the animal with the disease;

identifying an expression vector and expression protein that provides a therapeutic effect induced by vaccination; and determining the gene sequence of the antigenic expression protein encoded by the expression vector.

It is an advantage of the invention that it provides an efficient means of screening a library of nucleotide sequences and using identified clones for DNA vaccination trials to immediately assess the vaccine potential of clones. This aspect of easily using the identified clones to do vaccine trials far improves methods presently available.

In a further preferred embodiment of the invention, there is provided a method of screening a library of a nucleotide sequence for a nucleotide sequence encoding polypeptides of Mycoplasma, preferably *Mycoplasma hyopneumoniae*, said method comprising the steps of:

providing a source of nucleotide sequences from a sample of Mycoplasma;

providing an expression vector including a marker, preferably a polyHis tag;

introducing a nucleotide sequence into the expression vector;

identifying a Mycoplasma expression protein expressed by the expression vector by determining the presence of a fusion protein comprising a marker, preferably a polyHis tag, co-expressed with the expression protein translated by a nucleotide sequence; and determining the nucleotide sequence of the expression protein gene of Mycoplasma, preferably *Mycoplasma hyopneumoniae*.

The source of nucleotide sequence from a sample of Mycoplasma may be of genomic, mitochondrial, recombinant or mRNA origin. Where the source is genomic, genomic DNA may be isolated from Mycoplasma by any means known to the skilled addressee.

The Mycoplasma is preferably *Mycoplasma hyopneumoniae*. The methods of identification of the polyHis tag-Mycoplasma fusion protein are as described above.

Preferably, the nucleotide sequence encodes an antigenic protein. Accordingly, there is a further step of determining whether the protein elicits an immune response. Preferably, the antigenic protein is a Mycoplasma antigenic protein. More preferably a *Mycoplasma hyopneumoniae* antigenic protein.

The term "immune response" means a selective response mounted by the immune system in which specific antibodies and/or cytotoxic cells are produced against invading of foreign components such as microorganisms, parasites, transplanted tissue, proteins or antigens in general.

The term "immune system" includes any cells and tissues which enable the mounting of a specific protective response to invading of foreign components such as microorganisms, parasites, transplanted tissue, proteins or antigens in general aimed at protecting the body from infection and in some cases setting up a long lasting specific immunity to re-infection.

In yet another aspect of the present invention, there is provided a nucleotide sequence mutant, analogue, derivative or functionally active fragments thereof encoding a polypeptide of Mycoplasma, preferably *Mycoplasma hyopneumoniae*, said nucleotide sequence identified by the methods described above. Preferably the nucleotide sequence comprises a sequence according to any one of FIGS. 1 to 42, and mutants, analogues derivatives or functionally active fragments thereof. More specifically it comprises SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

In another embodiment there is provided a recombinant vector including a nucleotide sequence described above, mutant analogue derivative or functionally active fragment thereof. Preferably the nucleotide sequence is according to any one of FIGS. 1 to 42, mutant analogue derivative or functionally active fragment thereof. More specifically it comprises SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 7, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

The term "mutant, analogue, or derivative" refers to those sequences that may contain deletions, additions or substitutions of their sequences. Where these terms relate to a protein, the changes do not substantially change the activity of the protein. Where it relates to a changed nucleic acid molecule, the change does not result in a change in the reading frame of a protein coding region and preferably encodes a protein having no change, only a minor reduction or an increase in biological function.

The term "fragments" relates to a portion of an amino acid or nucleic acid sequence that is less than full length but is capable of hybridizing to a full length sequence and being recognised as being part of a nucleic acid sequence capable of encoding an amino acid sequence which is a portion of the full length sequence.

Due to the degeneracy of the genetic code, other nucleic acid sequences which encode the same or functionally equivalent amino acid sequence are included within the scope of the current invention. Such alterations of the nucleotide sequence may include substitutions of different nucleotides resulting in the same or a functionally equivalent gene product. Also included within the scope of this invention are nucleic acid sequences having deletions and/or additions and which result in a functionally equivalent gene product. In addition the gene product may include deletions, additions or substitutions of amino acid residues within the sequence which result in changes that still produce a functionally active product.

In a further embodiment, there is provided a host cell including a recombinant vector described above. The host cell may be any cell competent to receive the recombinant vector. Preferably the host cell is prokaryotic, more preferably it is *E. coli.*

In another aspect of the invention there is provided an amino acid sequence which encodes a polypeptide identified by the methods described above. The polypeptide may be a product of the expression vector or is an expression protein identified as a protein co-expressed with a marker preferably a polyHis marker. Preferably, the amino acid sequence is translated from a nucleotide sequence identified by the methods described above.

In a preferred aspect, the amino acid sequence encodes a polypeptide of Mycoplasma, preferably *Mycoplasma hyopneumoniae*. More preferably, the amino acid sequence comprises a sequence according to any one of FIGS. 1 to 42 or a mutant, analogue, derivative, or functionally active fragment thereof. More specifically it comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO 62, SEQ ID NO: 64, SEQ ID NO: 66, SEQ ID NO: 68, SEQ ID NO: 70, SEQ ID NO: 72, SEQ ID NO 74, SEQ ID NO: 76, SEQ ID NO: 78, SEQ ID NO: 80, SEQ ID NO: 82 or SEQ ID NO: 84 or a mutant, analogue, derivatives or functionally active fragments thereof.

In an even further aspect of the present invention, there is provided a polypeptide encoded by the amino acid sequence mutant, analogue, derivative or functionally active fragment thereof as described above. Preferably the sequence encodes a polypeptide of Mycoplasma, preferably *Mycoplasma hyopneumoniae*, said amino acid sequence being identified by the methods described above. Preferably the polypeptide is encoded by an amino acid sequence according to any one of FIGS. 1 to 42, mutant, analogues, derivatives or functionally active fragment thereof. More specifically it comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36. SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO 62, SEQ ID NO: 64, SEQ ID NO: 66, SEQ ID NO: 68, SEQ ID NO: 70, SEQ ID NO: 72, SEQ ID NO 74, SEQ ID NO: 76, SEQ ID NO: 78, SEQ ID NO: 80, SEQ ID NO: 82 or SEQ ID NO: 84 or a mutant, analogue, derivatives or functionally active fragments thereof.

The polypeptide may be isolated and purified by any methods known to the skilled addressee. Preferably, the methods of isolation utilise the polyHis tag which was used to identify expression protein or expression clones from a library of nucleotide sequences.

In a further embodiment, there is provided a composition comprising the polypeptide or nucleotide sequence as described above. The composition may be a pharmaceutical composition comprising at least one polypeptide or nucleotide sequence as described above and a pharmaceutically acceptable carrier. The composition may also be a vaccine composition comprising at least one polypeptide or nucleotide sequence described above. The vaccine composition may be capable of eliciting an immune response wherein the polypeptide is an antigenic protein or a nucleotide sequence preferably of Mycoplasma, more preferably of *Mycoplasma hyopneumoniae.*

In another aspect of the present invention, there is provided an antibody against a polypeptide described or identified according to the methods described above. Preferably the antibody is a monoclonal antibody.

Various procedures are known in the art which may be used for the production of antibodies to epitopes of the polypeptides described above. Various host animals may be used in the production of these antibodies following immunisation with the polypeptides including but not restricted to rabbits, mice, goats etc. Adjuvants may be used to increase the immunological response, depending on the host species, and may include but are not restricted to Freunds (complete and incomplete). Monoclonal antibodies may be prepared by using techniques which enable the continuous production of antibody molecules by cell lines in vitro. These may include, but are not limited to, the hybridoma technique (Kohler and Milstein, Nature 256, 495, (1975)). Antibodies to the polypeptides may find use in the detection of antigenic polypeptides in various tissues, body fluids and cell lines, for example in screening assays for the antigen, and in the affinity purification of polypeptides, preferably antigenic polypeptides.

The vaccine composition includes purified plasmid DNA including nucleotide sequences described above.

In yet another aspect of the present invention, there is provided a method of treating an infection, said method including administering an effective amount of an antigenic polypeptide encoded by an amino acid sequence said polypeptide being identified by the methods described above. Preferably the infection is a Mycoplasma infection. More preferably, the infection is a *Mycoplasma hyopneumoniae* infection.

Also it is preferred that the polypeptide is encoded by an amino acid sequence encoded by a nucleotide sequence according to any one of FIGS. 1 to 42, mutant, analogue, derivative or functionally active fragment thereof. More specifically the sequence comprises SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

It is also preferred that the polypeptide has an amino acid sequence according to any one of FIGS. 1 to 42, mutant, analogue, derivative or functionally active fragment thereof. More specifically it comprises SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO 62, SEQ ID NO: 64, SEQ ID NO: 66, SEQ ID NO: 68, SEQ ID NO: 70, SEQ ID NO: 72, SEQ ID NO 74, SEQ ID NO: 76, SEQ ID NO: 78, SEQ ID NO: 80, SEQ ID NO: 82 or SEQ ID NO: 84 or a mutant, analogue, derivatives or functionally active fragments thereof.

In yet another aspect of the present invention, there is provided a method of treating an infection, said method including administering to an animal in need, an effective amount of a DNA molecule including a nucleotide sequence identified by the methods described above. Preferably the infection is a Mycoplasma infection. More preferably, the infection is a *Mycoplasma hyopneumoniae* infection.

Preferably, the nucleotide sequence is according to any one of FIGS. 1 to 42, mutant, analogue, derivative or functionally active fragment thereof or more specifically, SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81 or SEQ ID NO: 83 or a mutant, analogue, derivatives or functionally active fragments thereof.

The DNA may be administered by injection which allows for cells to take up DNA or it may be applied topically. Preferably, the DNA is injected into the skin layer subcutaneously, or intramuscularly.

In another aspect of the present invention, there is provided a method of treating an infection, said method including administering an effective amount of an antibody specific to a polypeptide which has been identified by a method described above.

Preferably the infection is a Mycoplasma infection. More preferably, the infection is a *Mycoplasma hyopneumoniae* infection.

Preferably the polypeptide is encoded by an amino acid sequence according to any one of FIGS. 1 to 42, a mutant, analogue, derivative or functionally active fragment thereof or more specifically SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO 62, SEQ ID NO: 64, SEQ ID NO: 66, SEQ ID NO: 68, SEQ ID NO: 70, SEQ ID NO: 72, SEQ ID NO 74, SEQ ID NO: 76, SEQ ID NO: 78, SEQ ID NO: 80, SEQ ID NO: 82 or SEQ ID NO: 84 or a mutant, analogue, derivatives or functionally active fragments thereof.

The present invention will now be more fully described with reference to the accompanying Examples and Figures. It should be understood, however, that the description following is illustrative only and should not be taken in any way as a restriction on the generality of the invention described.

EXAMPLES

EXAMPLE 1

Construction of genomic libraries in pCl30, pCl31 and pCl32

Genomic DNA isolated from *Mycoplasma hyopneumoniae* was broken down into suitably sized fragments by sonication or partial restriction enzyme digestion. The DNA was then run on an agarose gel and size selected fractions cut from the gel and recovered. Vector DNA (pCl30, pCl31, and pCl32) was digested with an appropriate restriction enzyme (Sma I or BamHl) treated with shrimp alkaline phosphatase to remove the terminal phosphates, then run on an agarose gel. The linearized band was cut out and the DNA recovered. Genomic DNA fragments and cut vector DNA were mixed at molar ratios of between 1:1 and 5:1 and ligated using standard ligation conditions. The ligation mixtures were used to transform competent *E. coli* cells and thus produce a number of distinct genomic libraries.

EXAMPLE 2

Screening of the genomic libraries

The genomic libraries were plated onto Luria-Bertoni (LB) broth agar containing ampicillin (100 μg/ml) and grown overnight at 37° C. Filter lift replicas of the plates were made by placing dry, sterile nitrocellulose membranes on top of the colonies then immediately removing it and placing it colony side up onto an LB plate containing ampicillin and IPTG (1 mM) and incubating for 4 hours at 37° C. The membranes were then processed by standard methods to lyse the bacteria, neutralise the membranes and bind protein to the membranes. The dry membranes were then probed either with anti-polyHis antibodies or with conjugated nickel resin and the polyHis signals developed by addition of chromogenic substrate. The developed membranes were keyed back to the original plates and the positive colonies picked in to 96 well, deep well plates containing rich growth media supplemented with ampicillin. The clones were then grown at 37° C. Replicas of these plates were taken and held at −70° C. for long term storage.

EXAMPLE 3

Sequence analysis of selected clones

A collection of polyHis positive clones from each library was selected. Plasmid DNA was prepared and DNA sequence information from the inserted fragment was generated by automated dideoxy sequencing using a primer homologous to a region just upstream of the site of insertion into the vector. The sequence data generated was compared with the publicly available GenBank database. Homologies between our positive sequences and database entries were noted and in many instances this information gave some indication of the possible function of the gene fragments which had been cloned. On the basis of this homology information a subgroup of the positive clones was selected which were likely to represent genes which encoded proteins that may be easily accessible to the host immune system during *Mycoplasma hyopneumoniae* infection or that for other reasons were regarded as likely to offer some level of protection. These selected positive clones encode candidate protective antigens.

Some of the clones chosen for further study represent different sections of the same gene.

EXAMPLE 4

Screening of candidate protective antigens

A series of animal trials were conducted to investigate the therapeutic application of the identified genes. All the trials followed a similar protocol. Pigs from a *M. hyopneumoniae* free herd were vaccinated 3 times, at 2 week intervals, starting from 6 weeks of age. Each vaccination was with 500 μg of plasmid DNA, divided evenly between 2 shots, 1 shot into the tissue at the base of the back of each ear, delivered using a Biojector 2000 needless injection device with a No. 2 syringe. 1–2 weeks after the third vaccination the pigs were challenged by intratracheal instillation of a 5 ml dose of 0.45 μM filtered lung homogenate derived from a pig with an active *M. hyopneumoniae* infection. 3–4 weeks after challenge the pigs were euthanased and the lungs removed for scoring of pneumonic lesions. The pneumonic lesions were scored by counting the number of lung lobes that were affected and by estimating the percentage of each lung lobe that was affected by disease. This scoring system gives two measures of disease status, a lobe score and a lesion score. For each trial the average results across each group are presented. The trial results of those groups of clones which had a positive therapeutic effect are presented. Other groups of clones did not give a positive therapeutic effect and these results are not presented.

Trial 1

Vaccinated with a group of clones that included clones pAD612–789.

| Treatment | Lobe score | Lesion score |
|---|---|---|
| Unvaccinated, unchallenged | 0 | 0 |
| Unvaccinated, challenged | 4.4 | 120 |
| Vaccinated, challenged | 3.25 | 72.5 |

The vaccine containing clones pAD612–789 had a therapeutic effect. The lobe score in the vaccinated pigs was 26% lower than in the controls and the lesion score was 40% lower.

Trial 2

Two different groups of clones tested as vaccines.

Group 1: pAD's 662, 774, 784, 922, and 964

Group 2: pAD's 612, 633, 639, 640, 641, 653, 657, 659, 681, 700, 711, 721, 727, 742, 760, 789, 908, 910, 911, 913, 920, 923, 925, 950, 951, 966, 967, 977, 981, 983, 984, 994, 1001, 1005, 1013, 1016, 1020, 1027, 1033, 1037, 1038, 1040, and 1049.

| Treatment | Lobe score | Lesion score |
|---|---|---|
| Unvaccinated, unchallenged | 0 | 0 |
| Vector vaccinated, challenged | 3.4 | 67 |
| Group 1 vaccinated, challenged | 1.6 | 38 |
| Group 2 vaccinated, challenged | 2.2 | 51 |

The overall severity of disease induced in trial 2 was less than in trial 1 indicating a milder challenge. Both groups of clones had a therapeutic effect.

The Group 1 vaccine reduced the lobe score by 53% and the lesion score by 43%. The Group 2 vaccine reduced the lobe score by 35% and the lesion score by 24%, compared with the group vaccinated with the empty vector plasmid DNA.

Trial 3

Group 1: Same clones as Group 1 in trial 2.

The DNA was delivered in the standard way as detailed for the biojector or by genegun. For genegun delivery 1.6 micron gold particles were used with each pig receiving 4 shots, each of 1.25 μg DNA, at each of the 3 vaccination time points. Vaccination was behind each ear and the inside of each hind leg. The delivery pressure was 500 psi.

| Treatment | Lobe score | Lesion score |
|---|---|---|
| Unvaccinated, unchallenged | 0 | 0 |
| Vector vaccinated, challenged | 4.2 | 109 |
| Group 1 biojector vaccinated, challenged | 2.5 | 67 |
| Group 1 genegun vaccinated, challenged | 2.2 | 48.5 |

This trial again demonstrated that the five clones in Group 1 produce a therapeutic effect when delivered as naked DNA. The biojector delivered vaccine gave a 40% reduction in lobe score and a 39% reduction in lesion score. The same collection of clones delivered by genegun gave a 48% reduction in lobe score and a 56% reduction in lesion score.

Trial 4

Other combinations of the clones used in trial 2 were used in this trial.

Group 3: pAD's 653, 711, 727, 920, 951, and 965
Group 4: pAD's 612, 639, 640, 1005, 1020, and 1038
Group 5: pAD's 742, 760, 923, 925, 994, 984, and 1037

A group of 5 other clones that had not previously been used in trials was also included.

Group 6: pAD's 702, 763, 766, 957, and 996

| Treatment | Lobe score | Lesion score |
|---|---|---|
| Unvaccinated, unchallenged | 0 | 0 |
| Vector vaccinated, challenged | 5.0 | 106 |
| Group 3 vaccinated, challenged | 2.8 | 54 |
| Group 3 genegun vaccinated, challenged | 2.6 | 87 |
| Group 4 vaccinated, challenged | 3.0 | 79 |
| Group 5 vaccinated, challenged | 3.6 | 74 |
| Group 6 vaccinated, challenged | 2.75 | 42.5 |

All of these groups of clones produced a therapeutic effect in that they reduced the severity of pneumonic lesions. The group 3 clones reduced the lobe score by 44% when delivered by biojector and by 48% when delivered by genegun, and the lesion score by 49% when delivered by biojector and 18% when delivered by genegun. The other three experimental vaccines were delivered only by biojector. The group 4 vaccine reduced the lobe score by 40% and the lesion score by 25%. The group 5 vaccine reduced the lobe score by 28% and the lesion score by 30%. The group 6 vaccine reduced the lobe score by 45% and the lesion score by 60%.

This series of trials demonstrates that compared with unvaccinated or empty vector vaccinated pigs the collection of cloned genes detailed in this patent can produce a therapeutic effect by lowering the severity of lung lesions in the groups vaccinated with various combinations of the recombinant plasmids. On the basis of this demonstration of therapeutic effect a collection of 42 genes are claimed in the present invention.

EXAMPLE 5

Screening of genomic libraries to recover the complete genes

The clones listed in example 4 contain only partial gene sequences. It is desirable to identify the nucleotide sequence of the complete genes, as these are likely to encode further epitopes that will be useful in vaccine design. The complete coding regions of the genes represented by the clones in example 4 were recovered by screening two genomic libraries. The genomic libraries were constructed by ligating fragments created by digestion with the restriction enzymes EcoRl and BgIII into pUC18 vector digested with EcoRl and BamHI respectively. Ligation products were recovered by transformation of the ligation mix into XL2-BlueMRF' competent cells (Stratagene) and plating onto Luria-Bertoni agar plates containing 100 μg/ml ampicillin. Colonies were picked into 96 well plates containing rich growth media, grown overnight and then plasmid DNA was prepared for each. Plasmid DNA from each was denatured and spotted on to nylon membranes. Representative membranes were then probed with digoxigenin labelled PCR products generated from the inserted DNA present in each of the clones listed in example 4. Hybridizing clones were identified and analysed by restriction enzyme digestion, PCR using gene specific primers and by nucleotide sequencing The resulting gene sequences are detailed in FIGS. 1–42. A number of these sequences represent the complete coding sequence of the genes but for many of the genes only a partial sequence is available.

Finally it is to, be understood that various other modifications and/or alterations may be made without departing from the spirit of the present invention as outlined herein.

What is claimed is:

1. An isolated amino acid sequence of Mycoplasma comprising a sequence according to SEQ ID NO: 14.

2. An isolated or purified polypeptide comprising an amino acid sequence of claim 1.

3. A method of vaccinating against a *Mycoplasma hypopneumoniae* infection, said method including administering an effective amount of an antigenic polypeptide according to claim 2.

4. An amino acid sequence of claim 1 consisting of SEQ ID NO:14.

5. A method of vaccinating against *Mycoplasma hypopneumoniae* which comprises administering an effective amount of an antigenic amino acid sequence of claim 1.

6. A method of vaccinating against *Mycoplasma hypopneumoniae* which comprises administering an effective amount of an antigenic amino acid sequence of claim 4.

* * * * *